United States Patent
Bates et al.

(10) Patent No.: US 9,834,556 B2
(45) Date of Patent: *Dec. 5, 2017

(54) PROCESS OF PREPARING 3-(3-(4-AMINOCYCLOBUTYL)PHENYL)-5-PHENYL-3H-IMIDAZO[4,5-B]PYRIDIN-2-YL)PYRIDIN-2-AMINE

(71) Applicant: ARQULE, INC., Burlington, MA (US)

(72) Inventors: Craig Bates, Pelham, NH (US); Jian-Xie Chen, Guilderland, NY (US); Jianmin Mao, Winchester, MA (US); David P. Reed, Pelham, NH (US)

(73) Assignee: ArQule, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/258,104

(22) Filed: Sep. 7, 2016

(65) Prior Publication Data

US 2016/0376270 A1 Dec. 29, 2016

Related U.S. Application Data

(62) Division of application No. 14/666,694, filed on Mar. 24, 2015, now Pat. No. 9,464,083.

(60) Provisional application No. 61/969,546, filed on Mar. 24, 2014.

(51) Int. Cl.
C07D 471/04 (2006.01)
C07D 213/74 (2006.01)

(52) U.S. Cl.
CPC ......... *C07D 471/04* (2013.01); *C07D 213/74* (2013.01)

(58) Field of Classification Search
CPC .................................................. C07D 471/04
See application file for complete search history.

(56) References Cited

U.S. PATENT DOCUMENTS

| | | |
|---|---|---|
| 8,501,770 B2 | 8/2013 | Ashwell et al. |
| 8,609,688 B2 | 12/2013 | Ashwell et al. |
| 8,815,854 B2 | 8/2014 | Ashwell et al. |
| 8,962,619 B2 | 2/2015 | Ashwell et al. |
| 2002/0151549 A1 | 10/2002 | Hayakawa et al. |
| 2006/0035921 A1 | 2/2006 | Castelhano et al. |

FOREIGN PATENT DOCUMENTS

| | | |
|---|---|---|
| WO | WO 2007/111904 | 10/2007 |
| WO | WO 2011/082270 | 7/2011 |
| WO | WO 2013/078254 A1 | 5/2013 |

OTHER PUBLICATIONS

BASF "GPS Safety Summary Sodium dithionite" Online: "http://www.safety-summaries.basf.com/group/corporate/safety-summaries/en/literature-document:/GPS+Safety+Summaries--Sodium+dithionite-English.pdf " Mar. 2012.
Bukhryakov "Synthetic Approaches to Imidazo[4,5-b]pyridine Derivatives (Review)" Chemistry of Heterocyclic Compounds, vol. 47, No. 5, Aug. 2011 (Russian original vol. 47, No. 5, May 2011).
Yuan "New Strategy for the Synthesis of 2-Phenylbenzimidazole Derivatives with Sodium Perborate (SPB) as Oxidant" Tetrahedron, 2013, 69, p. 7026-7030.
Singh "Synthetic Utility of Catalytic Fe(III)/Fe(II) Redox Cycling Towards Fused Heterocycles: A Facile Access to Substituted Benzimidazole, Bisbenzimidazole and Imidazopyridine Derivatives" Synthesis, 2000, p. 1380 (abstract only).
Lacasse "Textile Chemicals: Environmental Data and Facts"Springer: 2004, p. 560.

*Primary Examiner* — David K O'Dell
(74) *Attorney, Agent, or Firm* — Cooley LLP; Matthew Pavao; Chen Chen

(57) ABSTRACT

The present invention is directed to a processes for the synthesis of 3-(3-(4-(1-aminocyclobutyl)phenyl)-5-phenyl-3H-imidazo[4,5-b]pyridin-2-yl)pyridin-2-amine:

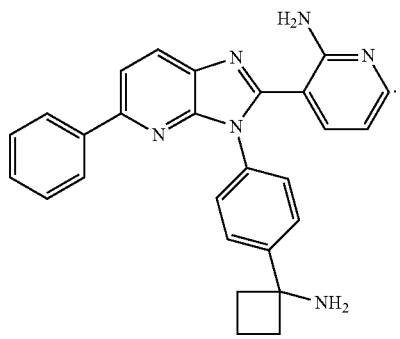

8 Claims, No Drawings

PROCESS OF PREPARING 3-(3-(4-AMINOCYCLOBUTYL)PHENYL)-5-PHENYL-3H-IMIDAZO[4,5-B]PYRIDIN-2-YL) PYRIDIN-2-AMINE

CROSS-REFERENCE TO RELATED APPLICATION

This application is a division of U.S. Ser. No. 14/666,694, filed Mar. 24, 2015 (now allowed), which claims priority to, and the benefit of, U.S. Ser. No. 61/969,546, filed Mar. 24, 2014, the contents of each of which are incorporated herein by reference in their entirety.

FIELD OF THE INVENTION

The present invention is directed to processes for the synthesis of 3-(3-(4-(1-aminocyclobutyl)phenyl)-5-phenyl-3H-imidazo[4,5-b]pyridin-2-yl)pyridin-2-amine.

BACKGROUND OF THE INVENTION

Cancer is the second leading cause of death in the United States, exceeded only by heart disease (*Cancer Facts and Figures* 2004, American Cancer Society, Inc.). Despite recent advances in cancer diagnosis and treatment, surgery and radiotherapy may be curative if a cancer is found early, but current drug therapies for metastatic disease are mostly palliative and seldom offer a long-term cure.

The AKT family regulates cellular survival and metabolism by binding and regulating many downstream effectors, e.g., Nuclear Factor-KB, Bcl-2 family proteins and murine double minute 2 (MDM2). Akt1 is known to play a role in the cell cycle. Moreover, activated Akt1 may enable proliferation and survival of cells that have sustained a potentially mutagenic impact and, therefore, may contribute to acquisition of mutations in other genes. Akt1 has also been implicated in angiogenesis and tumor development. Studies have shown that deficiency of Akt1 enhanced pathological angiogenesis and tumor growth associated with matrix abnormalities in skin and blood vessels. Since it can block apoptosis, and thereby promote cell survival, Akt1 is a major factor in many types of cancer.

Compound 3-(3-(4-(1-aminocyclobutyl)phenyl)-5-phenyl-3H-imidazo[4,5-b]pyridin-2-yl)pyridin-2-amine (also known as compound 7) has been shown to modulate AKT genes and treat proliferation disorders, including cancer (US 2011/0172203 A1, herein after referred to as the '203 application). A small-scale synthesis of 3-(3-(4-(1-aminocyclobutyl)phenyl)-5-phenyl-3H-imidazo[4,5-b]pyridin-2-yl)pyridin-2-amine (compound 7) has recently been published in the '203 application. The synthesis of the '203 application is impractical for producing large quantities of the compound and has several drawbacks.

Accordingly, there is a need for an improved synthetic route to 3-(3-(4-(1-aminocyclobutyl)phenyl)-5-phenyl-3H-imidazo[4,5-b]pyridin-2-yl)pyridin-2-amine (compound 7) that is amenable to commercial production that is safe and simple.

SUMMARY OF THE INVENTION

The present invention relates to a process of preparing 3-(3-(4-(1-aminocyclobutyl)phenyl)-5-phenyl-3H-imidazo[4,5-b]pyridin-2-yl)pyridin-2-amine:

(compound 7)

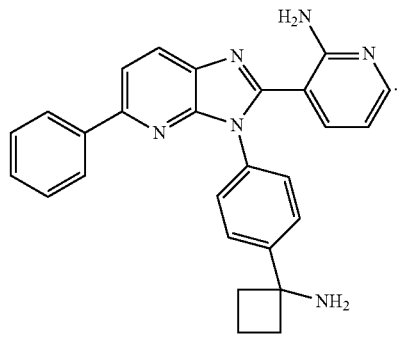 [SMILES: Nc1ncccc1-c1nc2ccc(-c3ccccc3)nc2n1-c1ccc(C2(N)CCC2)cc1]

In one aspect, the present invention relates to a process of preparing compound 7 comprising a four-step synthesis. In one aspect, the present invention relates to a process of preparing compound 7 comprising a three-step synthesis.

DETAILED DESCRIPTION OF THE INVENTION

The present invention is directed to a process of preparing 3-(3-(4-(1-aminocyclobutyl)phenyl)-5-phenyl-3H-imidazo[4,5-b]pyridin-2-yl)pyridin-2-amine (compound 7). The process of the invention is depicted in the representative Schemes below.

Scheme 1

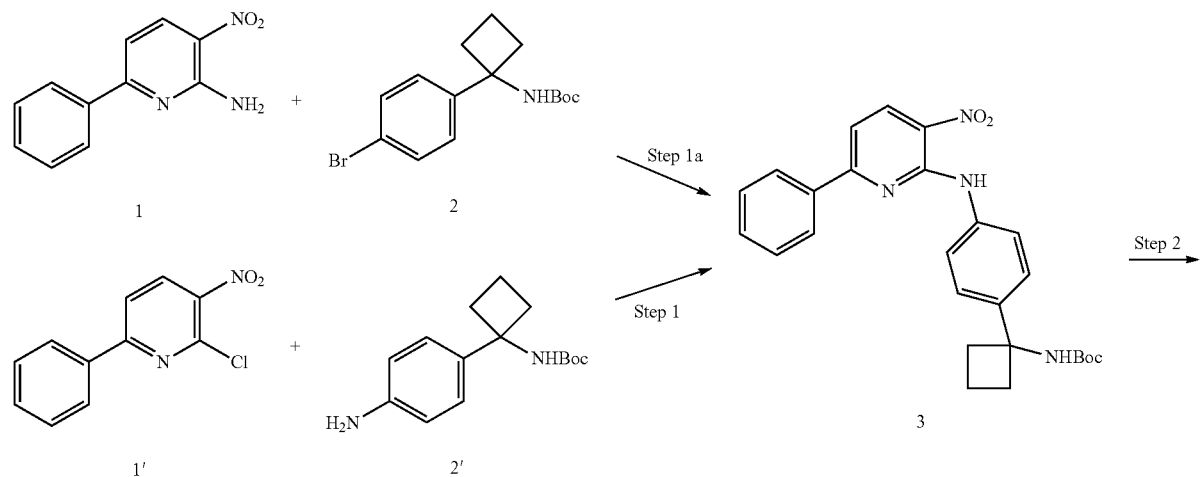

-continued
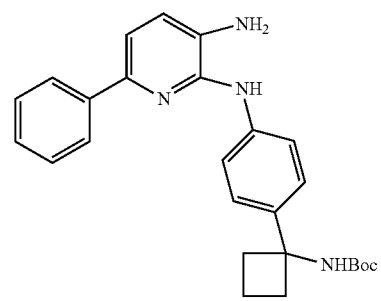
4
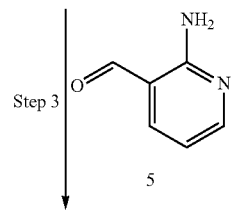
Step 3
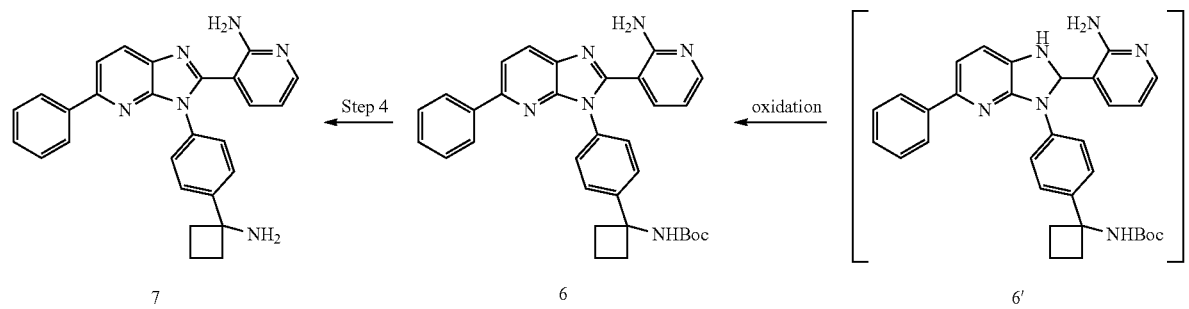
Scheme 1'
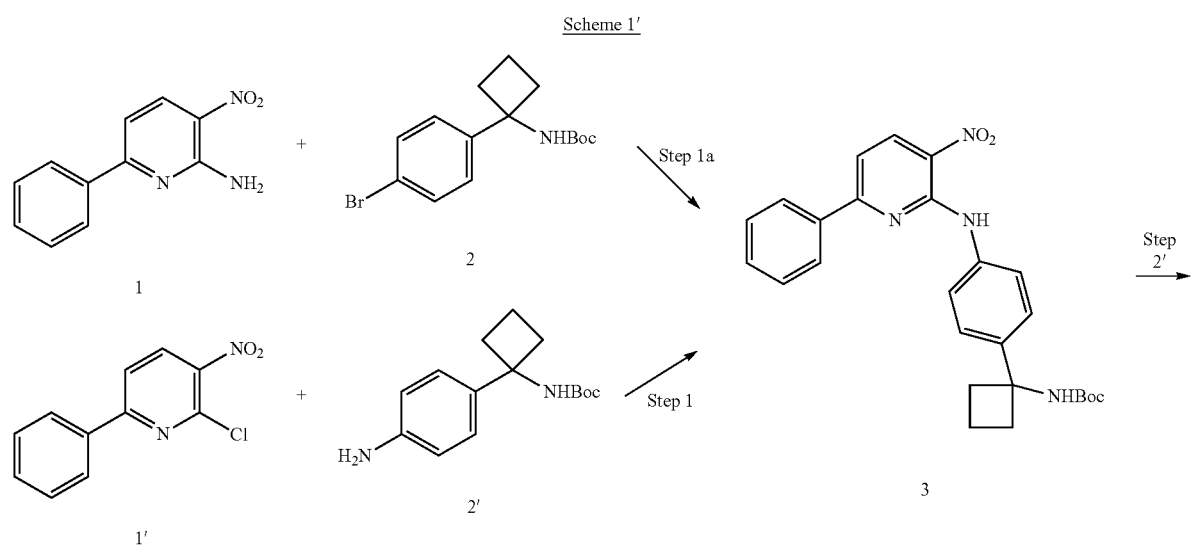

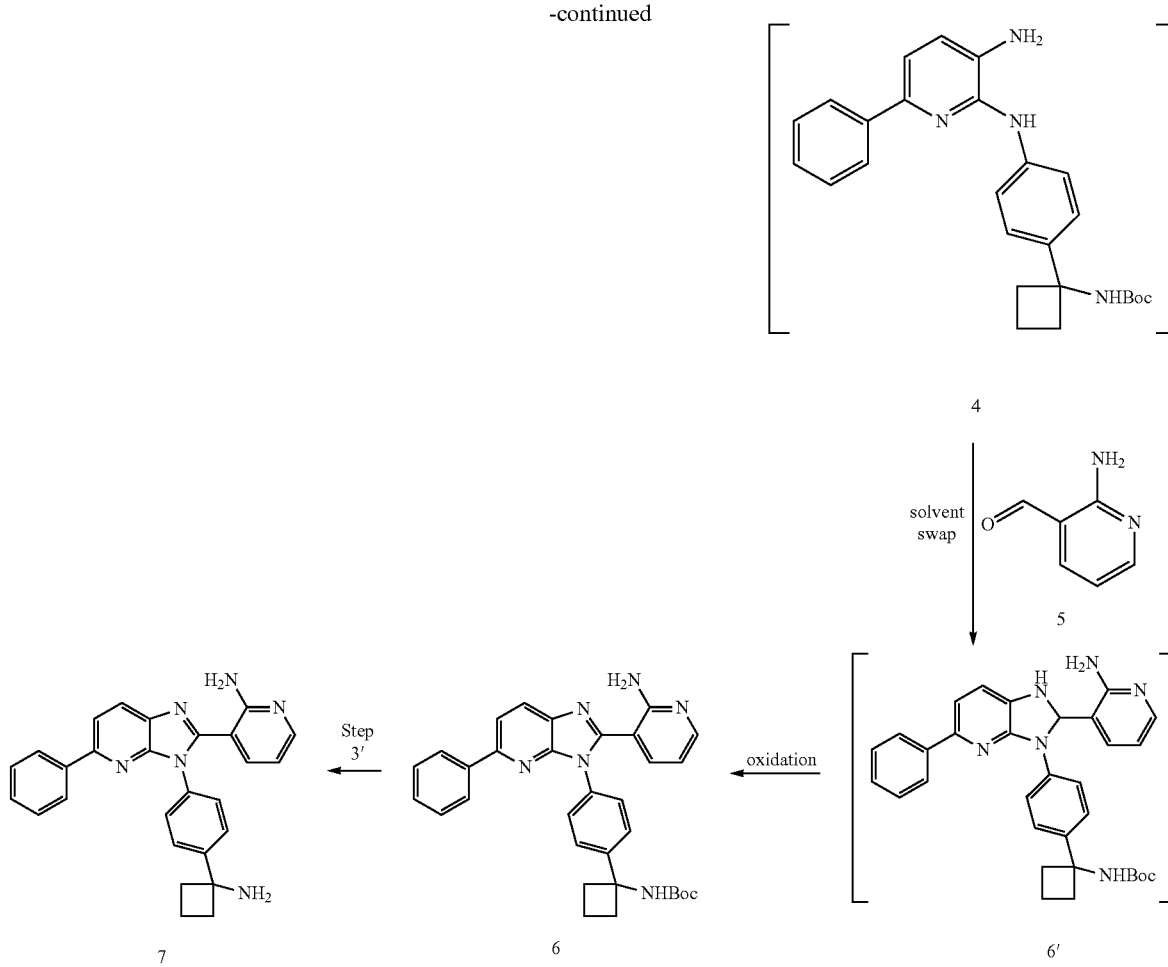

The processes of the invention have never been reported in the art.

In one embodiment, the process of the invention involves four steps (Scheme 1). The first step is a displacement reaction of 1' and 2' to afford compound 3 (Step 1) or alternatively, a cross coupling reaction of 1 and 2 to generate compound 3 (Step 1a). The second step is the reduction of compound 3 to form the aniline compound 4. The third step is the cyclization of compounds 4 and compound 5 (2-amino nicotinaldehyde) to afford the cyclized intermediate compound 6', which oxidizes in situ to form compound 6. The fourth step is the deprotection of compound 6 to afford 3-(3-(4-(1-aminocyclobutyl)phenyl)-5-phenyl-3H-imidazo[4,5-b]pyridin-2-yl)pyridin-2-amine (compound 7).

In one embodiment, the process of the invention involves three steps (Scheme 1'). In one embodiment, the second and third steps described in Scheme 1 are combined in a streamlined process (Step 2'). The first step is a displacement reaction of 1' and 2' to afford compound 3 (Step 1) or alternatively, a cross coupling reaction of 1 and 2 to generate compound 3 (Step 1a). The second step includes the reduction of compound 3 to form the intermediate aniline compound 4, which, after replacing the polar aprotic solvent with a polar protic solvent, are reacted with compound 5 to form compound 6', which is oxidized in situ to provide compound 6 (Step 2'). The third step is the deprotection of compound 6 to afford 3-(3-(4-(1-aminocyclobutyl)phenyl)-5-phenyl-3H-imidazo[4,5-b]pyridin-2-yl)pyridin-2-amine (compound 7) (Step 3').

In one embodiment, the present invention relates to a process of preparing 3-(3-(4-(1-aminocyclobutyl)phenyl)-5-phenyl-3H-imidazo[4,5-b]pyridin-2-yl)pyridin-2-amine (compound 7) comprising the step of Step 3, reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine (compound 7) comprising the steps of Step 2, treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4); and Step 3, reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine (compound 7) comprising the steps of Step 1, reacting 2-chloro-3-nitro-6-phenylpyridine (compound 1') with tert-butyl (1-(4-aminophenyl)cyclobutyl)carbamate (compound 2') in the presence of a base in a polar aprotic solvent to form tert-butyl (1-(4-((3-nitro-6-phenylpyridin-2-yl)amino)phenyl)cyclobutyl)carbamate (compound 3);

Step 2, treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4); and Step 3, reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine (compound 7) comprising the steps of Step 1a, coupling 3-nitro-6-phenylpyridin-2-amine (compound 1) with tert-butyl (1-(4-bromophenyl)cyclobutyl)carbamate (compound 2) in the presence of a palladium catalyst and a phosphorus ligand in a polar aprotic solvent to form tert-butyl (1-(4-((3-nitro-6-phenylpyridin-2-yl)amino)phenyl)cyclobutyl)carbamate (compound 3);

Step 2, treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4); and Step 3, reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine comprising the steps of Step 1, reacting 2-chloro-3-nitro-6-phenylpyridine (compound 1') with tert-butyl (1-(4-aminophenyl)cyclobutyl)carbamate (compound 2') in the presence of a base in a polar aprotic solvent to form tert-butyl (1-(4-((3-nitro-6-phenylpyridin-2-yl)amino)phenyl)cyclobutyl)carbamate (compound 3);

Step 2, treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4);

Step 3, reacting tert-butyl (1-(4-((3-amino-6-phenylpyridin-2-yl)amino)phenyl)cyclobutyl)carbamate (compound 4) with 2-amino nicotinaldehyde (5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6); and Step 4, treating tert-butyl (1-(4-(2-(2-aminopyridin-3-yl)-5-phenyl-3H-imidazo[4,5-b]pyridin-3-yl)phenyl)cyclobutyl)carbamate (compound 6) with an acid in a polar aprotic solvent to form 3-(3-(4-(1-aminocyclobutyl)phenyl)-5-phenyl-3H-imidazo[4,5-b]pyridin-2-yl)pyridin-2-amine (compound 7).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine comprising the steps of Step 1a, coupling 3-nitro-6-phenylpyridin-2-amine (compound 1) with tert-butyl (1-(4-bromophenyl)cyclobutyl)carbamate (compound 2) in the presence of a palladium catalyst and a phosphorus ligand in a polar aprotic solvent to form tert-butyl (1-(4-((3-nitro-6-phenylpyridin-2-yl)amino)phenyl)cyclobutyl)carbamate (compound 3);

Step 2, treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4);

Step 3, reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6); and Step 4, treating tert-butyl (1-(4-(2-(2-aminopyridin-3-yl)-5-phenyl-3H-imidazo[4,5-b]pyridin-3-yl)phenyl)cyclobutyl)carbamate (compound 6) with an acid in a polar aprotic solvent to form 3-(3-(4-(1-aminocyclobutyl)phenyl)-5-phenyl-3H-imidazo[4,5-b]pyridin-2-yl)pyridin-2-amine (compound 7).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine (compound 7) comprising the step of Step 2', treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4), replacing the polar aprotic solvent with a polar protic solvent, and reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine (compound 7) comprising the steps of Step 1, reacting 2-chloro-3-nitro-6-phenylpyridine (compound 1') with tert-butyl (1-(4-aminophenyl)cyclobutyl)carbamate (compound 2') in the presence of a base in a polar aprotic solvent to form tert-butyl (1-(4-((3-nitro-6-phenylpyridin-2-yl)amino)phenyl)cyclobutyl)carbamate (compound 3); and Step 2', treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4), replacing the polar aprotic solvent with a polar protic solvent, and reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine (compound 7) comprising the steps of Step 1a, coupling 3-nitro-6-phenylpyridin-2-amine (compound 1) with tert-butyl (1-(4-bromophenyl)cyclobutyl)carbamate (compound 2) in the presence of a palladium catalyst and a phosphorus ligand in a polar aprotic solvent to form tert-butyl (1-(4-((3-nitro-6-phenylpyridin-2-yl)amino)phenyl)cyclobutyl)carbamate (compound 3); and Step 2', treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4), replacing the polar aprotic solvent with a polar protic solvent, and reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine comprising the steps of Step 2', treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4), replacing the polar aprotic solvent with a polar protic solvent, and reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6); and Step 3', treating tert-butyl (1-(4-(2-(2-aminopyridin-3-yl)-5-phenyl-3H-imidazo[4,5-b]pyridin-3-yl)phenyl)cyclobutyl)carbamate (compound 6) with an acid in a polar aprotic solvent to form 3-(3-(4-(1-aminocyclobutyl)phenyl)-5-phenyl-3H-imidazo[4,5-b]pyridin-2-yl)pyridin-2-amine (compound 7).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine comprising the steps of Step 1, reacting 2-chloro-3-nitro-6-phenylpyridine (compound 1') with tert-butyl (1-(4-aminophenyl)cyclobutyl)carbamate (compound 2') in the presence of a base in a polar aprotic solvent to form tert-butyl (1-(4-((3-nitro-6-phenylpyridin-2-yl)amino)phenyl)cyclobutyl)carbamate (compound 3);

Step 2', treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4), replacing the polar aprotic solvent with a polar protic solvent, and reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6); and Step 3', treating tert-butyl (1-(4-(2-(2-aminopyridin-3-yl)-5-phenyl-3H-imidazo[4,5-b]pyridin-3-yl)phenyl)cyclobutyl)carbamate (compound 6) with an acid in a polar aprotic solvent to form 3-(3-(4-(1-aminocyclobutyl)phenyl)-5-phenyl-3H-imidazo[4,5-b]pyridin-2-yl)pyridin-2-amine (compound 7).

In one embodiment, the process of the invention relates to the preparation of 3-(3-(4-(1-aminocyclobutyl)phenyl)-5-phenyl-3H-imidazo[4,5-b]pyridin-2-yl)pyridin-2-amine comprising the steps of Step 1a, coupling 3-nitro-6-phenylpyridin-2-amine (compound 1) with tert-butyl (1-(4-bromophenyl)cyclobutyl)carbamate (compound 2) in the presence of a palladium catalyst and a phosphorus ligand in a polar aprotic solvent to form tert-butyl (1-(4-((3-nitro-6-phenylpyridin-2-yl)amino)phenyl)cyclobutyl)carbamate (compound 3);

Step 2', treating tert-butyl (1-(4-((3-nitro-6-phenylpyridin-2-yl)amino)phenyl)cyclobutyl)carbamate (compound 3) with a reducing agent in a polar aprotic solvent to form tert-butyl (1-(4-((3-amino-6-phenylpyridin-2-yl)amino)phenyl)cyclobutyl)carbamate (compound 4), replacing the polar aprotic solvent with a polar protic solvent, and reacting tert-butyl (1-(4-((3-amino-6-phenylpyridin-2-yl)amino)phenyl)cyclobutyl)carbamate (compound 4) with 2-amino nicotinaldehyde (compound 5) in the presence of an oxidant and an acid in a polar protic solvent to form tert-butyl (1-(4-(2-(2-aminopyridin-3-yl)-5-phenyl-3H-imidazo[4,5-b]pyridin-3-yl)phenyl)cyclobutyl)carbamate (compound 6); and Step 3', treating tert-butyl (1-(4-(2-(2-aminopyridin-3-yl)-5-phenyl-3H-imidazo[4,5-b]pyridin-3-yl)phenyl)cyclobutyl)carbamate (compound 6) with an acid in a polar aprotic solvent to form 3-(3-(4-(1-aminocyclobutyl)phenyl)-5-phenyl-3H-imidazo[4,5-b]pyridin-2-yl)pyridin-2-amine (compound 7).

In one embodiment, the process of the invention comprises of Step 3. Step 3 is the cyclization of compound 4 and compound 5 (2-amino nicotinaldehyde) to afford intermediate compound 6', which oxidizes to form compound 6:

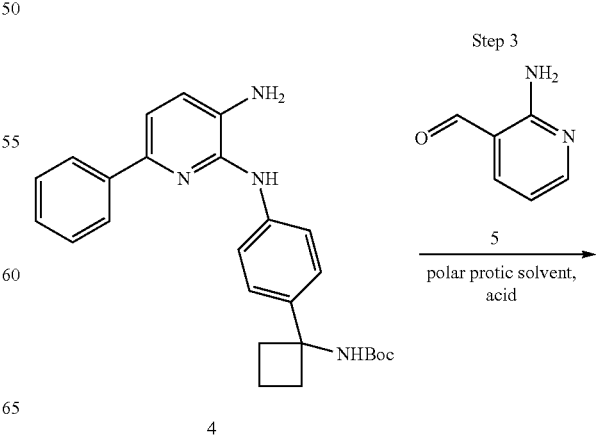

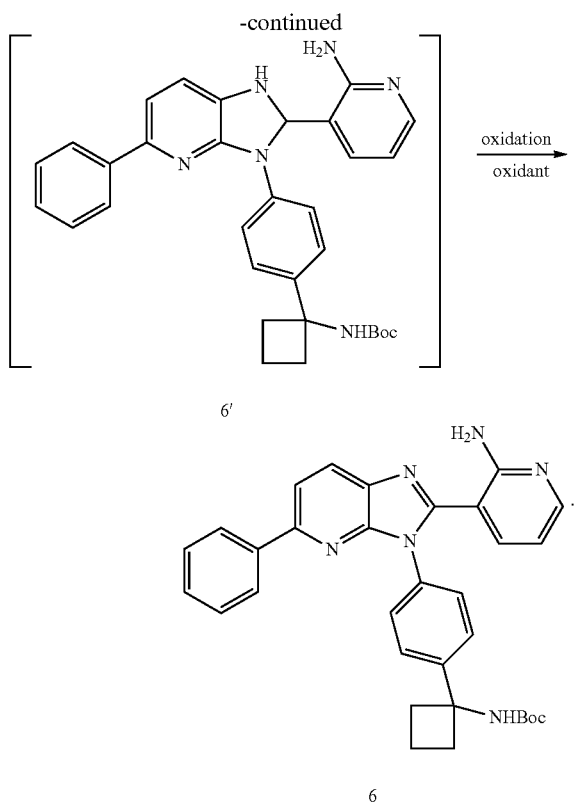

In one embodiment, the polar protic solvent is a $C_{1-4}$ alcohol. In a further embodiment, the polar protic solvent is selected from the group consisting of methanol, ethanol, n-propanol, isopropanol, n-butanol, s-butanol, and t-butanol. In a further embodiment, the polar protic solvent is methanol.

In one embodiment, the acid is an organic acid. In a further embodiment, the acid is selected from the group consisting of formic acid, acetic acid, and propanoic acid. In a further embodiment, the acid is acetic acid. In one embodiment, the ratio of the acid to the solvent is in the range of about 1:25 to about 25:1, about 1:20 to about 20:1, about 1:15 to about 15:1, about 1:1 to about 15:1, about 3:1 to about 12:1, or about 5:1 to about 10:1. In a further embodiment, the ratio of the acid to the solvent is about 9:1. In a further embodiment, the ratio of acetic acid to methanol is about 9:1.

In one embodiment, the oxidant is air. In another embodiment the oxidant is a metal or non-metal based salt or catalyst. In a further embodiment, the oxidant is selected from the group consisting of metal acetate, metal perborate, metal chloride, palladium based catalyst, and hydrates thereof. In a further embodiment, the oxidant is selected from the group consisting of alkali metal perborate and hydrates thereof. In a further embodiment, the oxidant is selected from the group consisting of copper acetate, sodium perborate, ferric chloride, palladium on carbon, and hydrates thereof. In a further embodiment, the oxidant is selected from the group consisting of $Cu(OAc)_2.H_2O$, $NaBO_3.4H_2O$, $FeCl_3.6H_2O$, and 10% Pd/C. In a further embodiment, the oxidant is $NaBO_3.4H_2O$.

In one embodiment, the temperature of the reaction mixture is about 10° C. to about 30° C. In a further embodiment, the temperature is about 15° C. to about 25° C. In a further embodiment, the temperature is about 20° C. In another embodiment, the temperature of the reaction mixture is about 10° C. to about 60° C. In a further embodiment, the temperature is about 30° C. to about 50° C. In a further embodiment, the temperature is about 40° C.

In one embodiment, the reaction mixture is stirred for about 40 hours to about 50 hours. In a further embodiment, the reaction mixture is stirred for about 43 hours to about 46 hours. In a further embodiment, the reaction mixture is stirred for about 45 hours. In another embodiment, the reaction mixture is stirred for about 10 hours to about 18 hours. In a further embodiment, the reaction mixture is stirred for about 12 hours to about 16 hours. In one embodiment, the reaction mixture is stirred for about 12 hours, about 13 hours, about 14 hours, or about 15 hours.

In one embodiment, the oxidation is completed in about 40 hours to about 50 hours. In a further embodiment, the oxidation is completed in about 43 hours to about 46 hours. In a further embodiment, the oxidation is completed in about 45 hours. In another embodiment, the oxidation is completed in for about 10 hours to about 18 hours. In a further embodiment, the oxidation is completed in about 12 hours to about 16 hours. In one embodiment, the oxidation is completed in about 12 hours, about 13 hours, about 14 hours, or about 15 hours.

In one embodiment, the oxidation is completed before a significant amount of the over-oxidized impurity (M+16) N-oxide of compound 6 is produced. In a further embodiment, the amount of the over-oxidized impurity (M+16) N-oxide is below 10% AUC, 9% AUC, 8% AUC, 7% AUC, 6% AUC, 5% AUC, 4% AUC, 3% AUC, 2% AUC, 1% AUC, 0.9% AUC, 0.8% AUC, 0.7% AUC, 0.6% AUC, 0.5% AUC, 0.4% AUC, 0.3% AUC, 0.2% AUC, 0.1% AUC, 0.09% AUC, 0.08% AUC, 0.07% AUC, 0.06% AUC, 0.05% AUC, 0.04% AUC, 0.03% AUC, 0.02% AUC, or 0.01% AUC when oxidation is completed. In a further embodiment, the amount of the over-oxidized impurity (M+16) N-oxide is below 3% AUC, 2% AUC, 1% AUC, 0.9% AUC, 0.8% AUC, 0.7% AUC, 0.6% AUC, 0.5% AUC, 0.4% AUC, 0.3% AUC, 0.2% AUC, 0.1% AUC, 0.09% AUC, 0.08% AUC, 0.07% AUC, 0.06% AUC, 0.05% AUC, 0.04% AUC, 0.03% AUC, 0.02% AUC, or 0.01% AUC when oxidation is completed.

In one embodiment, isolation of compound 6 comprises concentrating the reaction mixture containing compound 6. In one embodiment, isolation of compound 6 comprises adding a base. In one embodiment, isolation of compound 6 comprises adding a base after the concentration of compound 6. In one embodiment, the base is hydroxide (e.g., NaOH, KOH). In one embodiment, the hydroxide is KOH. In one embodiment, compound 6 is isolated from 2-methyl tetrahydrofuran and isopropylacetate. In one embodiment, isolation of compound 6 comprises washing the mixture containing compound 6 with 2-MeTHF. In one embodiment, isolation of compound 6 comprises removing the aqueous layer after the washing to obtain an organic layer. In one embodiment, isolation of compound 6 comprises washing the organic layer with brine and removing the resulting aqueous layer. In one embodiment, the steps of washing with brine and removing the resulting aqueous layer is repeated once, twice or three times. In one embodiment, isolation of compound 6 comprises adding IPAc to the organic layer after the washing step. In one embodiment, the IPAc is mixed with 2-MeTHF. In one embodiment, adding IPAc to the organic layer results in the formation of a slurry. In one embodiment, the compound 6 is washed with isopropylacetate, isopropylacetate/heptane mixture, and heptane. In one embodiment, the isopropyl/heptane mixture is in a ratio of 1:1.

In one embodiment, compound 6 is purified, comprising dissolving compound 6 in DCM and eluting the dissolved compound 6 through DCM silica gel. In one embodiment, the gel is flushed with EtOAc.

In one embodiment, the process of the invention comprises Step 2. Step 2 is the reduction of compound 3 to form the aniline compound 4:

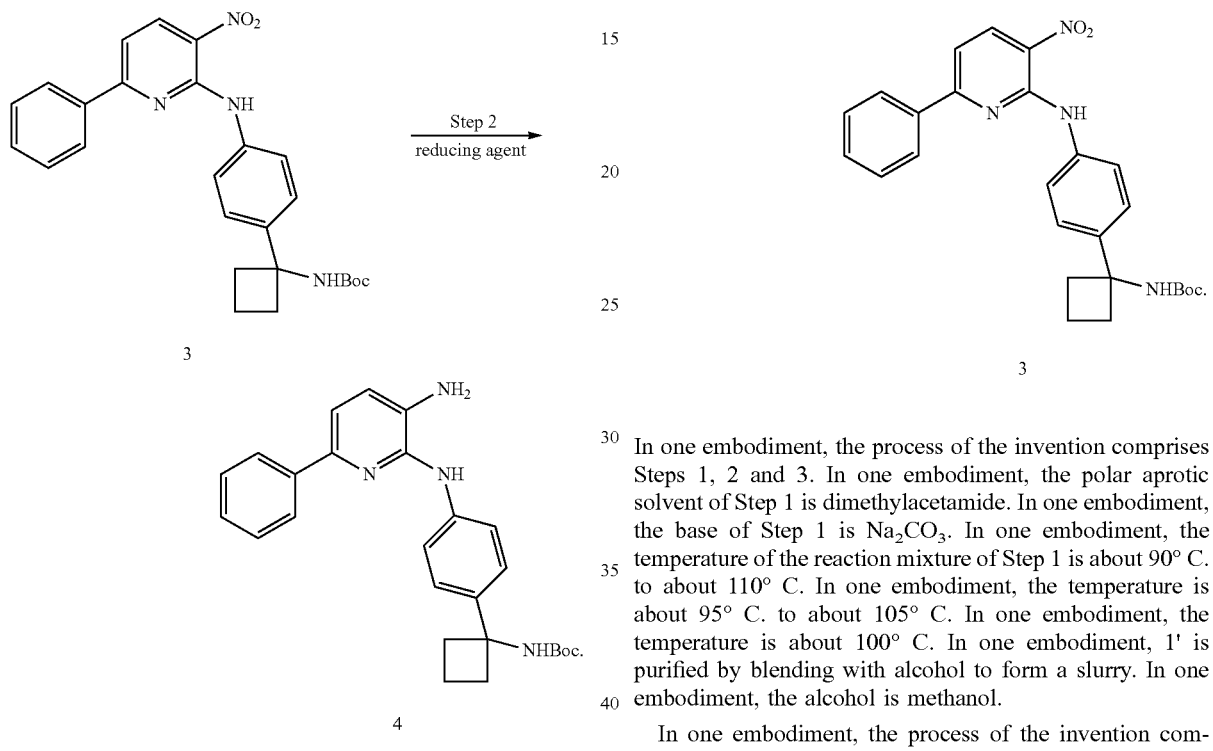

In one embodiment, the process of the invention comprises Steps 2 and 3. In one embodiment, the reducing agent of step 2 is hydrogen gas over catalytic Pd/C. In one embodiment, the polar aprotic solvent of Step 2 is, EtOAc, tetrahydrofuran, or 2-methyltetrahydrofuran. In one embodiment, the isolation compound 4 of Step 2 comprises filtering the reaction mixture through Celite®. In one embodiment, the isolation further comprises adding methanol and concentrating the reaction to dryness.

In one embodiment, the process of the invention comprises Step 1. Step 1 is a displacement reaction of 1' and 2' to afford compound 3:

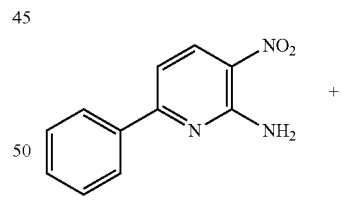

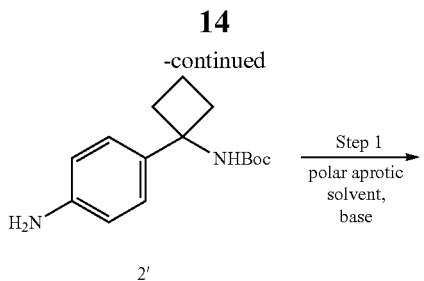

In one embodiment, the process of the invention comprises Steps 1, 2 and 3. In one embodiment, the polar aprotic solvent of Step 1 is dimethylacetamide. In one embodiment, the base of Step 1 is $Na_2CO_3$. In one embodiment, the temperature of the reaction mixture of Step 1 is about 90° C. to about 110° C. In one embodiment, the temperature is about 95° C. to about 105° C. In one embodiment, the temperature is about 100° C. In one embodiment, 1' is purified by blending with alcohol to form a slurry. In one embodiment, the alcohol is methanol.

In one embodiment, the process of the invention comprises Step 1a. Step 1a is a cross coupling reaction of 1 and 2 to generate compound 3:

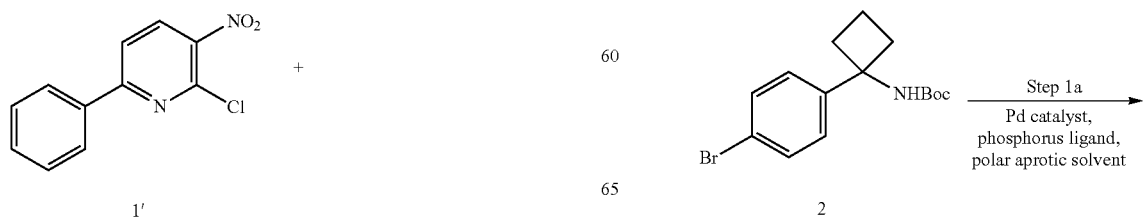

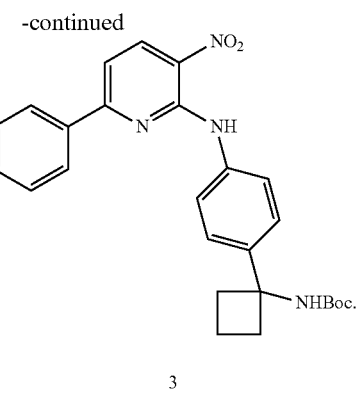

3

In one embodiment, the process of the invention comprises Steps 1a, 2 and 3. In one embodiment, the palladium catalyst of Step 1a is a Pd(II) catalyst. In one embodiment, the Pd(II) catalyst is $Pd_2(dba)_3$. In one embodiment, the phosphorus ligand of Step 1a is 4,5-bis(diphenylphosphino)-9,9-dimethylxanthene. In one embodiment, the polar aprotic solvent of Step 1a is tetrahydrofuran. In one embodiment, the temperature of the reaction mixture of Step 1a is about 60° C. to about 80° C. In one embodiment, the temperature of the reaction mixture is about 65° C. to about 75° C. In one embodiment, the temperature of the reaction mixture is about 70° C.

In one embodiment, the process of the invention comprises Step 4. Step 4 is the deprotection of compound 6 to afford compound 7:

ment, the polar aprotic solvent of Step 4 is dichloromethane. In one embodiment, the acid of Step 4 is methanesulfonic acid. In one embodiment, the ratio of acid to compound 6 of Step 4 is about 5:1. In one embodiment, the reaction mixture of Step 4 is complete in about 1.5 h to about 3 h. In one embodiment, the reaction mixture is complete in about 2 h to about 2.5 h. In one embodiment, the reaction mixture is complete in about 2 h.

In one embodiment, a slurry forms in Step 4. In one embodiment, isolation of compound 7 comprises adding water to the slurry and removing the resulting aqueous layer and retaining the DCM layer. In one embodiment, isolation of compound 7 comprises adding water to the DCM layer and removing the aqueous layer. In one embodiment, isolation of compound 7 comprises combining the aqueous layer and washing the layer with DCM. In one embodiment, isolation of compound 7 comprises adding a base. In one embodiment, the base is hydroxide (e.g., NaOH, KOH). In one embodiment, the hydroxide is NaOH. In one embodiment, isolation of compound 7 comprises drying the organic layer after addition of a base to obtain solid compound 7. In one embodiment, isolation of compound 7 comprises concentrating the solution after addition of a base and adding IPAc.

In one embodiment, the process of the invention comprises Step 2'. Step 2' is the reduction of compound 3 to form the intermediate aniline compound 4, which, after replacing the polar aprotic solvent with a polar protic solvent, are reacted with compound 5 to form compound 6', which is oxidized in situ to provide compound 6:

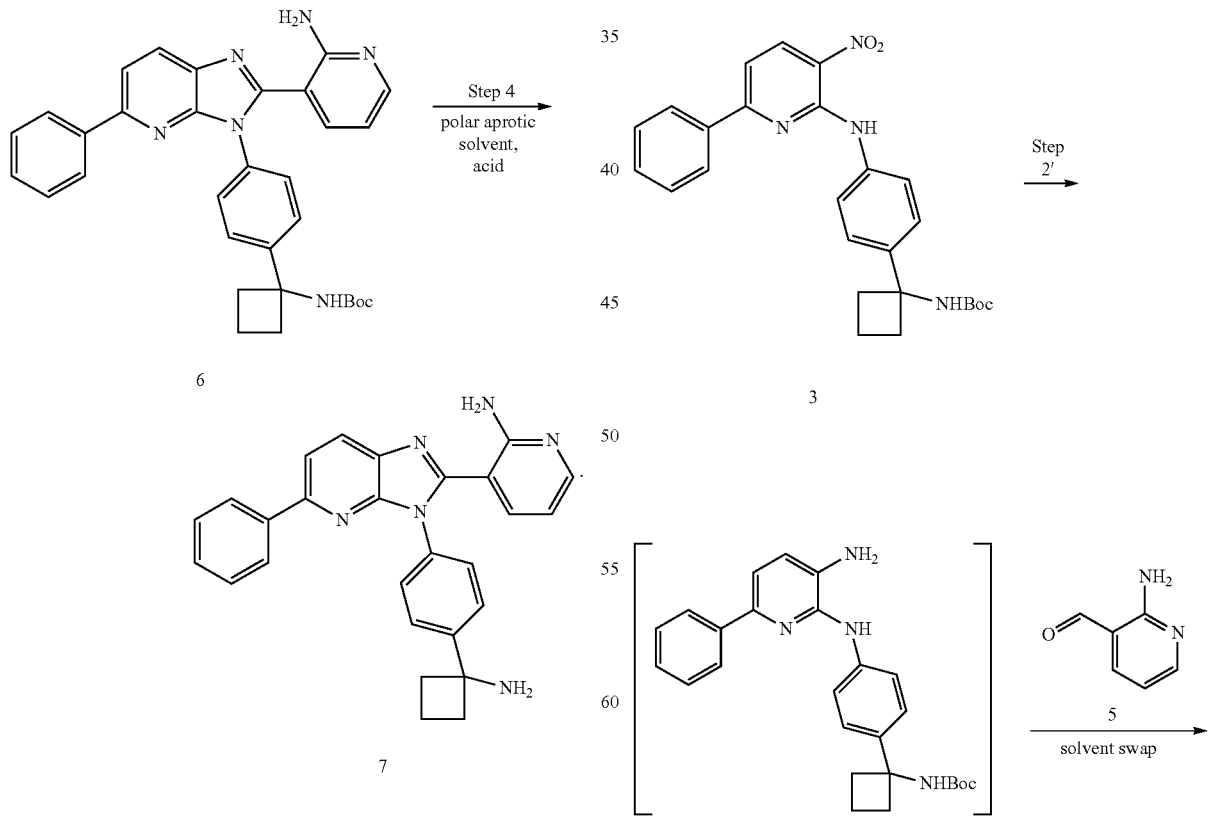

In one embodiment, the process of the invention comprises Steps 1, 2, 3 and 4. In one embodiment, the process of the invention comprises Steps 1a, 2, 3 and 4. In one embodi- -continued

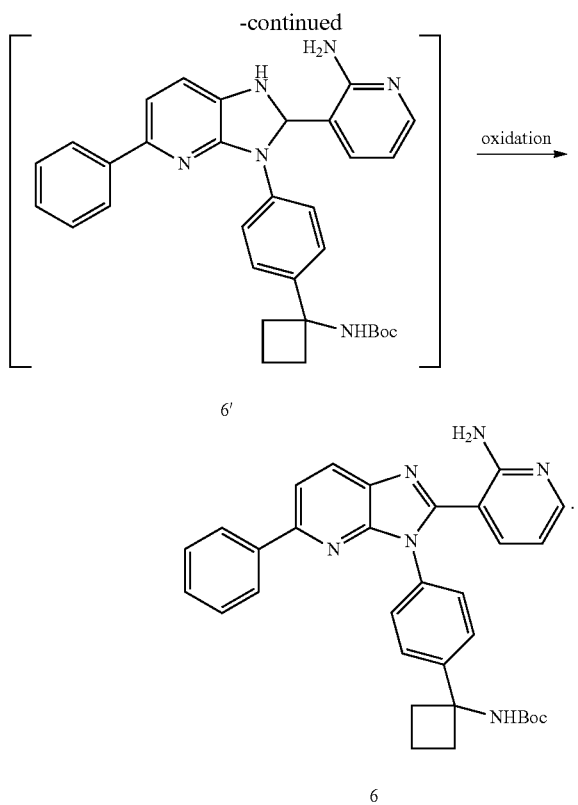

6'

6

In one embodiment, the process of the invention comprises Steps 1 and 2'. In one embodiment, Step 2' comprises replacing the polar aprotic solvent such as THF with a polar protic solvent such as MeOH. In one embodiment, the polar aprotic solvent used in the reduction of compound 3 to form aniline compound 4 in Step 2' is ethyl acetate, THF, or 2-MeTHF. In one embodiment, the solvent is THF. In one embodiment, the reducing agent of Step 2' is hydrogen gas over catalytic Pd/C. In one embodiment, the hydrogen gas is at moderate pressures of about 20 to about 50 psi. In one embodiment, the isolation of compound 4 comprises filtering the reaction mixture through Celite®. In one embodiment, the isolation further comprises adding methanol and concentrating the reaction to dryness.

In one embodiment, the polar protic solvent used in the reaction of compound 4 and compound 5 in Step 2' is a $C_{1-4}$ alcohol. In a further embodiment, the polar protic solvent is selected from the group consisting of methanol, ethanol, n-propanol, isopropanol, n-butanol, s-butanol, and t-butanol. In another embodiment, the polar protic solvent is methanol. In another embodiment, the acid used in the reaction of compound 4 and compound 5 in Step 2' is an organic acid. In a further embodiment, the acid is selected from the group consisting of formic acid, acetic acid, and propanoic acid. In another embodiment, the acid is acetic acid. In one embodiment, the ratio of acid to solvent used in Step 2' is in the range of about 1:25 to about 25:1, 1:20 to about 20:1, 1:15 to about 15:1, about 1:1 to about 15:1, about 3:1 to about 12:1, or about 5:1 to about 10:1. In a further embodiment, the ratio of acid to solvent is about 9:1. In a further embodiment, the ratio of acetic acid to methanol is about 9:1.

In one embodiment, the oxidant employed in Step 2' is a metal or non-metal based salt or catalyst. In a further embodiment, the oxidant is selected from the group consisting of metal acetate, metal perborate, metal chloride, palladium based catalyst, and hydrates thereof. In a further embodiment, the oxidant is selected from the group consisting of alkali metal perborate and hydrates thereof. In a further embodiment, the oxidant is selected from the group consisting of copper acetate, sodium perborate, ferric chloride, palladium on carbon, and hydrates thereof. In a further embodiment, the oxidant is selected from the group consisting of $Cu(OAc)_2.H_2O$, $NaBO_3.4H_2O$, $FeCl_3.6H_2O$, and 10% Pd/C. In a further embodiment, the oxidant is $NaBO^3.4H_2O$.

In one embodiment, the temperature of the reaction mixture in the reaction of compound 4 and compound 5 in Step 2' is about 10° C. to about 30° C. In a further embodiment, the temperature is about 15° C. to about 25° C. In a further embodiment, the temperature is about 20° C. In another embodiment, the temperature of the reaction mixture is about 10° C. to about 60° C. In a further embodiment, the temperature is about 30° C. to about 50° C. In a further embodiment, the temperature is about 40° C. In one embodiment, the reaction mixture is stirred for about 40 hours to about 50 hours. In a further embodiment, the reaction mixture is stirred for about 43 hours to about 46 hours. In a further embodiment, the reaction mixture is stirred for about 45 hours. In another embodiment, the reaction mixture is stirred for about 10 hours to about 18 hours. In a further embodiment, the reaction mixture is stirred for about 12 hours to about 16 hours. In one embodiment, the reaction mixture is stirred for about 12 hours, about 13 hours, about 14 hours, or about 15 hours.

In one embodiment, the oxidation is completed in about 40 hours to about 50 hours. In a further embodiment, the oxidation is completed in about 43 hours to about 46 hours. In a further embodiment, the oxidation is completed in about 45 hours. In another embodiment, the oxidation is completed in for about 10 hours to about 18 hours. In a further embodiment, the oxidation is completed in about 12 hours to about 16 hours. In one embodiment, the oxidation is completed in about 12 hours, about 13 hours, about 14 hours, or about 15 hours. In one embodiment, the oxidation is completed before a significant amount of the over-oxidized impurity (M+16) N-oxide of compound 6 is produced. In a further embodiment, the amount of the over-oxidized impurity (M+16) N-oxide is below 10% AUC, 9% AUC, 8% AUC, 7% AUC, 6% AUC, 5% AUC, 4% AUC, 3% AUC, 2% AUC, 1% AUC, 0.9% AUC, 0.8% AUC, 0.7% AUC, 0.6% AUC, 0.5% AUC, 0.4% AUC, 0.3% AUC, 0.2% AUC, 0.1% AUC, 0.09% AUC, 0.08% AUC, 0.07% AUC, 0.06% AUC, 0.05% AUC, 0.04% AUC, 0.03% AUC, 0.02% AUC, or 0.01% AUC when oxidation is completed. In a further embodiment, the amount of the over-oxidized impurity (M+16) N-oxide is below 3% AUC, 2% AUC, 1% AUC, 0.9% AUC, 0.8% AUC, 0.7% AUC, 0.6% AUC, 0.5% AUC, 0.4% AUC, 0.3% AUC, 0.2% AUC, 0.1% AUC, 0.09% AUC, 0.08% AUC, 0.07% AUC, 0.06% AUC, 0.05% AUC, 0.04% AUC, 0.03% AUC, 0.02% AUC, or 0.01% AUC when oxidation is completed.

In one embodiment, isolation of compound 6 comprises concentrating the reaction mixture containing compound 6. In one embodiment, isolation of compound 6 comprises adding a base. In one embodiment, isolation of compound 6 comprises adding a base after the concentration of compound 6. In one embodiment, the base is hydroxide (e.g., NaOH, KOH). In one embodiment, the hydroxide is KOH. In one embodiment, compound 6 is isolated from 2-methyl tetrahydrofuran and isopropylacetate. In one embodiment, isolation of compound 6 comprises washing the mixture containing compound 6 with 2-MeTHF. In one embodiment, isolation of compound 6 comprises removing the aqueous layer after the washing to obtain an organic layer. In one embodiment, isolation of compound 6 comprises washing the organic layer with brine and removing the resulting aqueous layer. In one embodiment, the steps of washing with brine and removing the resulting aqueous layer is repeated once, twice or three times. In one embodiment, isolation of compound 6 comprises adding IPAc to the organic layer after the washing step. In one embodiment, the IPAc is mixed with 2-MeTHF. In one embodiment, adding IPAc to the organic layer results in the formation of a slurry. In one embodiment, the compound 6 is washed with isopropylacetate, isopropylacetate/heptane mixture, and heptane. In one embodiment, the isopropyl/heptane mixture is in a ratio of 1:1.

In one embodiment, compound 6 is purified, comprising dissolving compound 6 in DCM and eluting the dissolved compound 6 through DCM silica gel. In one embodiment, the gel is flushed with EtOAc.

In one embodiment, the process of the invention comprises of Step 3'. Step 3' is the deprotection of compound 6 to afford compound 7:

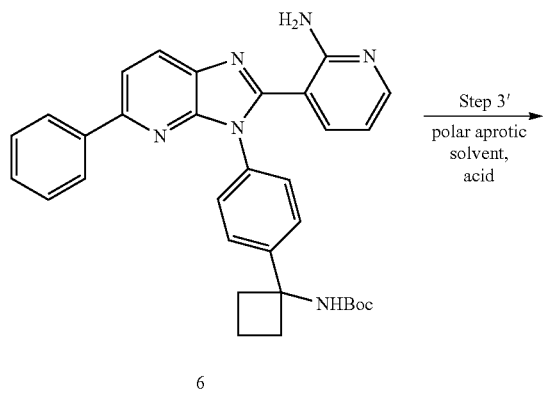

6

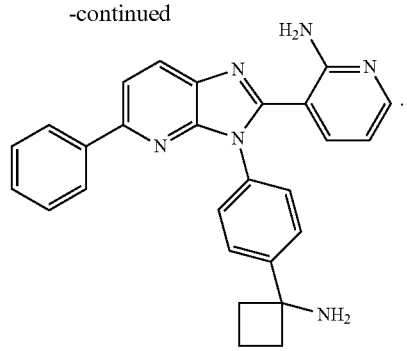

7

In one embodiment, the process of the invention comprises Steps 1, 2' and 3'. In one embodiment, the polar aprotic solvent of Step 3' is dichloromethane. In one embodiment, the acid of Step 3' is methanesulfonic acid. In one embodiment, the ratio of acid to compound 6 is about 5:1. In one embodiment, the reaction mixture of Step 3' is complete in about 1.5 h to about 3 h. In one embodiment, the reaction mixture of Step 3' is complete in about 2 h to about 2.5 h. In one embodiment, the reaction mixture of Step 3' is complete in about 2 h.

In one embodiment, a slurry forms in Step 3'. In one embodiment, isolation of compound 7 comprises adding water to the slurry and removing the resulting aqueous layer and retaining the DCM layer. In one embodiment, isolation of compound 7 comprises adding water to the DCM layer and removing the aqueous layer. In one embodiment, isolation of compound 7 comprises combining the aqueous layer and washing the layer with DCM. In one embodiment, isolation of compound 7 comprises adding a base. In one embodiment, the base is hydroxide (e.g., NaOH, KOH). In one embodiment, the hydroxide is NaOH. In one embodiment, isolation of compound 7 comprises drying the organic layer after addition of a base to obtain solid compound 7. In one embodiment, isolation of compound 7 comprises concentrating the solution after addition of a base and adding IPAc.

Drawbacks of the Previous Process

The process of the present application is an improvement over the process disclosed in the prior '203 application. The process to prepare compound 7 hydrochloride in the '203 patent is depicted in Scheme 2:

Scheme 2

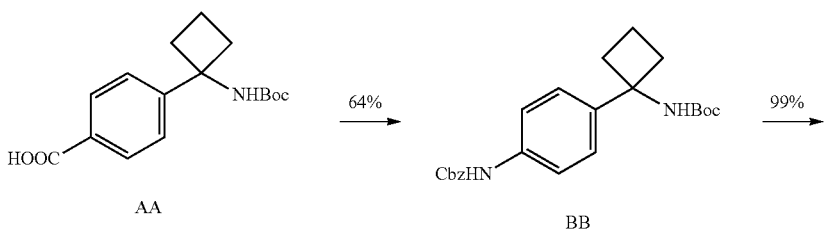

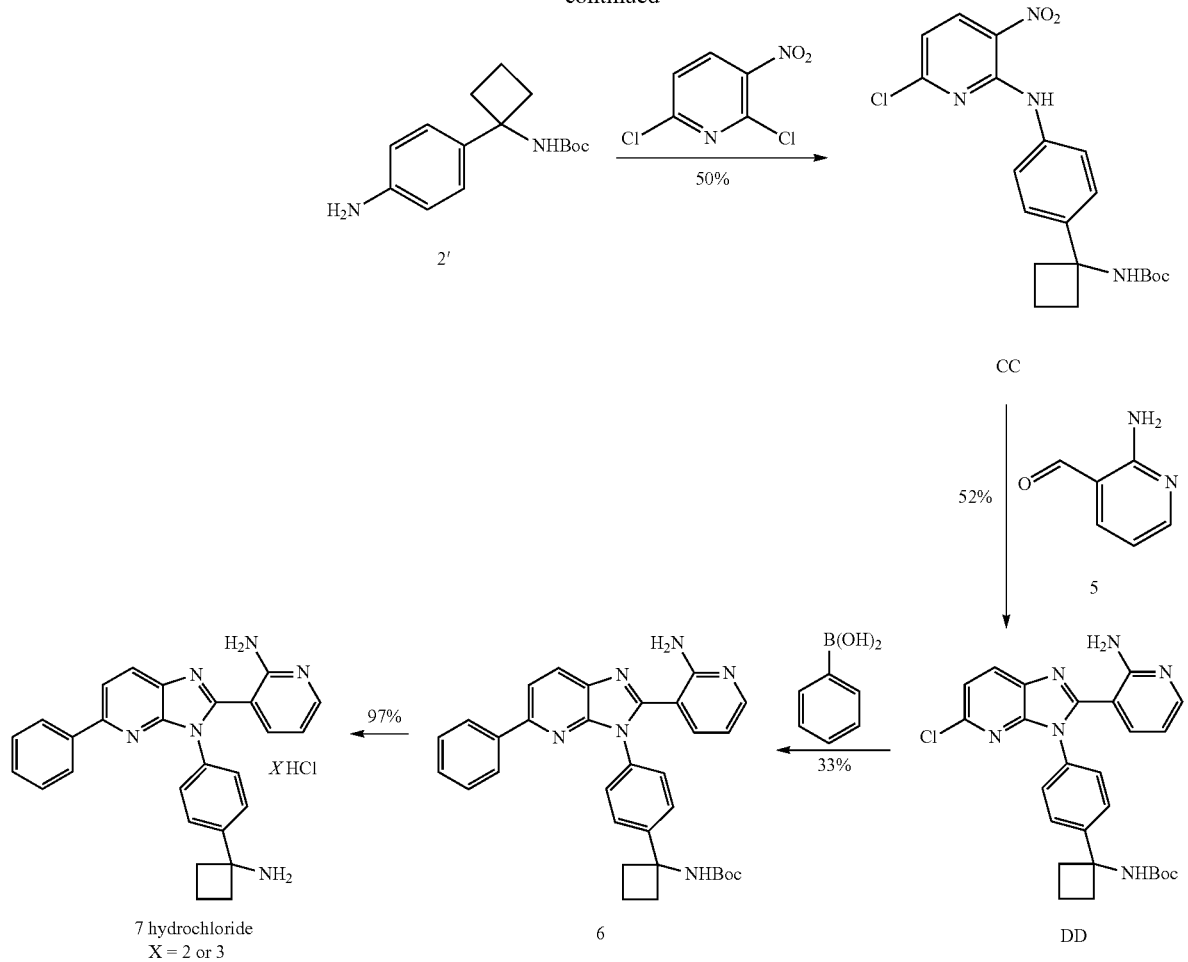

The process of the '203 application as in Scheme 2 starts with carboxylic acid AA which is subjected to a Curtius rearrangement using diphenylphosphoryl azide (DPPA) followed by trapping the isocyanate with benzyl alcohol, which generates the Cbz protected intermediate BB. Deprotection under hydrogenolysis conditions provides the aniline 2'. Addition of aniline 2' to 2,6-dichloro-3-nitropyridine proceeds to give crude CC. After purification by column chromatography, CC is subjected to reductive conditions and cyclized with 2-amino nicotinealdehyde (5) to afford the cyclized compound DD. Suzuki coupling of the cyclized product to benzene boronic acid affords compound 6. Following deprotection of 6 with HCl in dioxane, the desired compound 7 hydrochloride salt is isolated as a non-crystalline solid.

The process of the '203 application is difficult to scale up, expensive to carry out, and not suitable for commercial scale production. The drawbacks of the process of the '203 application are, at least, as follows:
1. follows a linear route with an overall yield of 5%,
2. employs potentially explosive azide chemistry,
3. requires expensive column chromatography purification,
4. utilizes palladium chemistry to prepare the penultimate intermediate 6, which leads to an unacceptable level of palladium impurity in 7,
5. introduces expensive materials at the beginning of the synthesis, and
6. utilizes complicated redox chemistry using $Na_2S_2O_4$.

The process of the present invention is a superior route for the production of 7 and overcomes the above-listed drawbacks. For example, the process of the invention places the steps which employ palladium earlier in the route, which decreases the amount of palladium impurity, if any, in the end product, compound 7. For example, the reaction to generate compound 1 (Scheme 1 or Scheme 1') and the cross coupling reaction to generate 3 (Scheme 1 or Scheme 1') involving palladium are placed earlier in process of the invention. On the contrary, the '203 process employs palladium chemistry to prepare the penultimate intermediate 6, which leads to impurity problems in the final product, compound 7.

The process of the invention is also convergent with a reduced number of steps and eliminates the need for azide chemistry and $Na_2S_2O_4$ (see Scheme 2, preparation of compound DD). Azides are known to be dangerous and toxic. $Na_2S_2O_4$ is a flammable solid and may ignite in the presence of moisture and air. Therefore, eliminating the need for azide chemistry and $Na_2S_2O_4$ makes the process of the invention safer and more practical.

The process of the invention can be carried out on a large scale whereas the process of the '203 application is expensive and difficult to scale up. For example, the preparation of compound 2' using the process of the '203 process involves subjecting compound BB to a Curtius rearrangement using DPPA followed by trapping the isocyanate with excess benzyl alcohol (see Scheme 2, preparation of compound BB). Although this chemistry is amenable to small scale, it is difficult and challenging to carry out on a large scale. On the small scale, the Cbz protected compound BB is prepared only in a modest yield of 62% in two crops with both precipitation and column purification, which is labor intensive and prohibitively expensive to carry out on a large scale.

The process of the invention uses compound 3 as a synthetic intermediate (Scheme 1 or Scheme 1'), which is analogous to the preparation of compound CC (Scheme 2) in the '203 synthesis. The preparation of compound CC of the '203 process typically affords only a 50% yield, whereas compound 3 using the process of the invention affords 86% yield. Specifically, compound 3 is obtained in the reaction of 1' and 2' in DMA in the presence of $Na_2CO_3$.

Another example of the drawback of the '203 process involves the deprotection of 6 by treatment with anhydrous HCl in dioxane directly to give 7 hydrochloride salt as a non-crystalline solid (Scheme 2). A large excess of HCl (10 equiv.) in dioxane is required. During the deprotection, the salt of 6 immediately precipitates out of solution making the reaction slow and a challenge to monitor due to the heterogeneous nature. The product, as isolated, is likely a mixture of bis and tris-salts (HCl) since ion chromatographic analysis reported a value which was in between the theoretical values of bis and tris salts.

Attempts to apply some of reagents and the conditions of the '203 process to the present route also failed. For example, applying the methodology of the '203 application to prepare compound 6 starting from compound 3 has many complications. Specifically, utilizing the conditions to generate compound DD from CC of Scheme 2 to convert 3 to 6 of the present invention has many drawbacks (Scheme 3).

Scheme 3

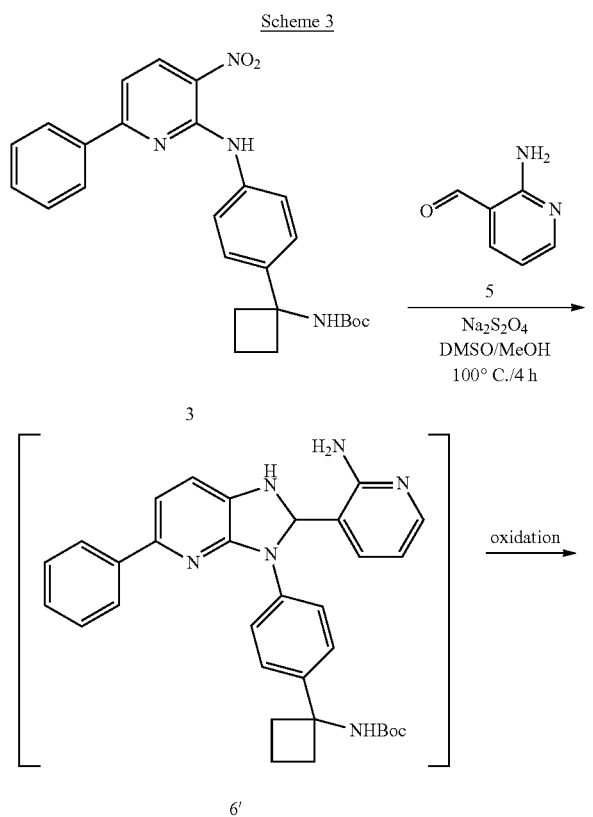

The '203 process to convert CC to DD is complicated and carried out as a one pot reaction (Scheme 2). Applying the conditions of the '203 process, the nitro moiety of 3 (of the present invention) is reduced to the aniline derivative which then reacts with aldehyde 5 to form the presumed imine intermediate. An intramolecular addition gives the cyclized intermediate 6' which is surprisingly stable and can be observed by LCMS analysis throughout the progress of the reaction. Oxidation of 6' affords 6. A number of problems are realized for the reaction as performed. The most difficult problem is a significant amount of the deprotected 6 under these conditions. During the work-up, it is determined that the pH of the quenched aqueous phases is quite acidic (e.g., pH=3), likely contributing to the large amount of deprotected product. Precipitation of 6 complicates the manipulation of the work-up and makes scale-up less plausible. These conditions as employed are not favorable for future development opportunities. Due to the complications in applying the conditions of the '203 process to the present synthetic route, new conditions were developed to overcome the above described complication.

Alternatively, instead of applying the '203 methodology to convert 3 to 6, which resulted in deprotection of 6 and complications with the work-up, the claimed process is a new approach that employs a two step method to synthesize 6 from 4 (Scheme 4).

Scheme 4

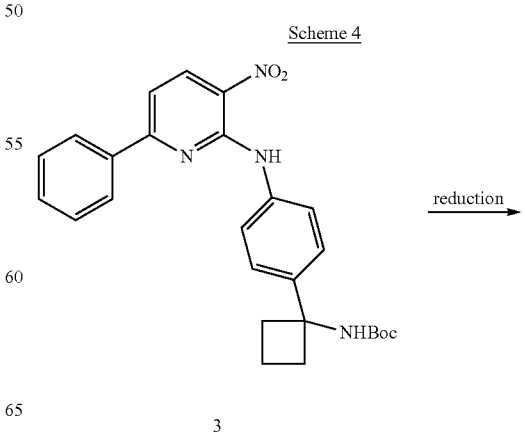

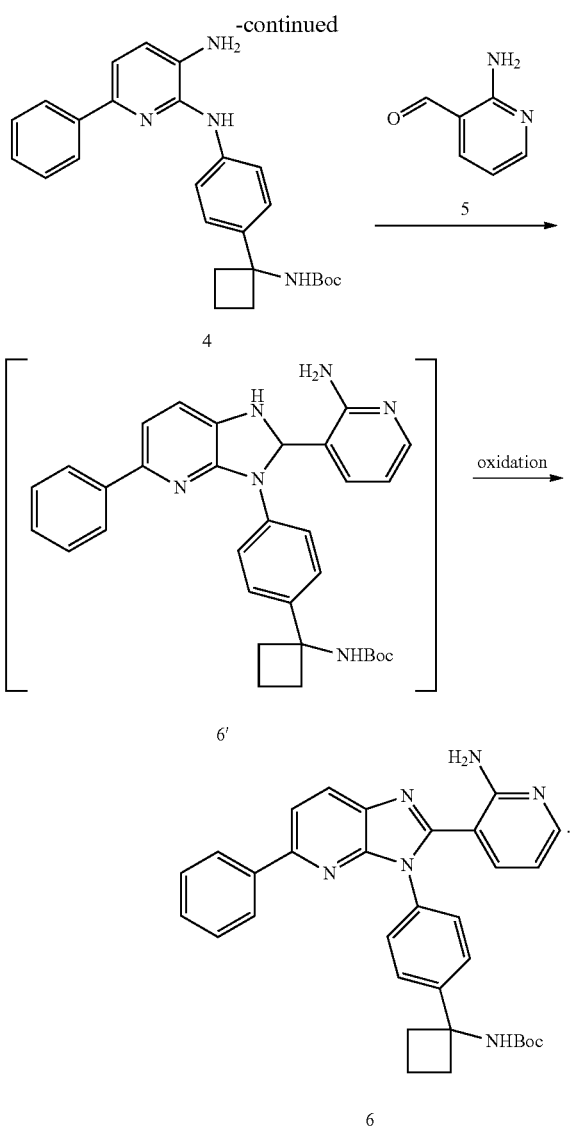

The first step is a discrete reduction of 3 to the aniline 4 followed by imine formation, cyclization and then oxidation. Hydrogenolysis of 3 with Pd/C (e.g., 10%) affords compound 4 in high yield (e.g., quantitative yield). A series of reactions was then performed using a variety of reaction conditions to determine the feasibility of the cyclization (see Table 4) of Example 2. Compound 4 is readily converted to compound 6; and on a large scale, compound 6 is isolated in about 86% yield.

The process of the invention overcomes the drawbacks of the '203 process to produce a synthetic method that is safe for large scale preparation.

Development and Optimization of the Process of the Invention

The development and optimization of the process of the invention comprises of the synthesis of compounds 1, 1', 2, 2', 3, 4, 6 and 7. The steps are discussed in the order of Step 1 (synthesis of compound 3), Step 2 in Scheme 1 (synthesis of compound 4), Step 3 in Scheme 1 (synthesis of compound 6), Step 2' in Scheme 1' (synthesis of intermediate compound 4 and then compound 6), Step 4 in Scheme 1 or Step 3' in Scheme 1' (synthesis of compound 7) and then the synthesis of the starting compounds, 1, 1', 2, and 2'. Lastly, purification of 6 and 7 with high Pd level is discussed.

Step 1: Synthesis of Compound 3

In one embodiment, compound 3 can be synthesized by using a displacement reaction and/or cross-coupling reaction (Scheme 5).

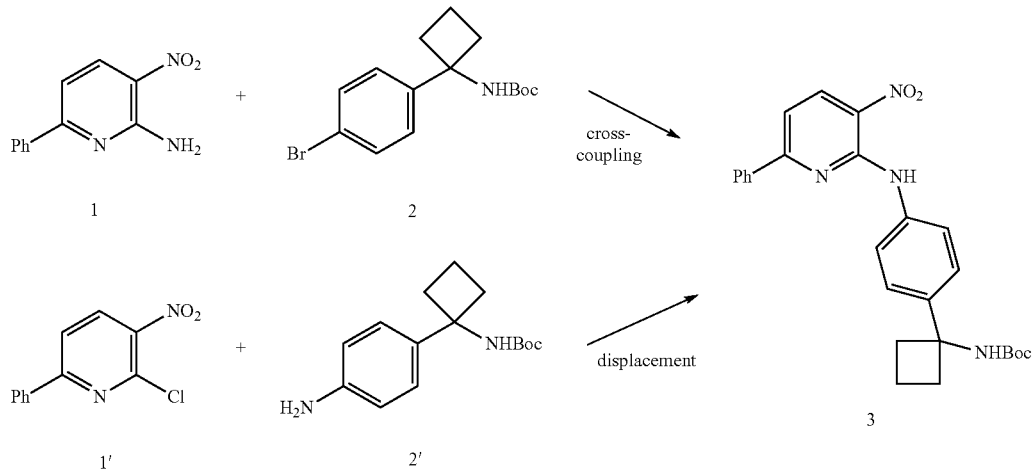

In one embodiment, using a displacement reaction, the preparation of compound 3 is carried out by heating compound 1' and compound 2' in a polar aprotic solvent (e.g., DMA) with a base (e.g., Na₂CO₃, 2 equiv.) to about 100° C. overnight. Once the reaction is complete, the reaction mixture is generally cooled to ambient temperature and about 3% aqueous NaCl solution and EtOAc are added. In one embodiment, the EtOAc layer is dried with Na₂SO₄ and concentrated to an oil. The crude compound 3 can be re-dissolved in EtOAc and washed with additional water to remove the residual DMA. In one embodiment, the reaction is performed on a larger scale (e.g., 30 g), and compound 3 is typically precipitated out of solution during the workup. Compound 3 can be isolated in about 64% yield. In one embodiment, the extraction solvent is 2-MeTHF. In one embodiment, heptane can be added as an anti-solvent to increase the isolated yield with no decrease in purity. In one embodiment, compound 3 is crystallized from a 2-MeTHF/heptane (e.g., 50/50 2-MeTHF/heptane (18 vol.) solution) in about 85% yield. Table 6 in Example 3 provides a detailed discussion of the solubility analysis of compound 3 in 2-MeTHF and heptane.

In another embodiment, a cross coupling reaction of compound 1 and compound 2 is carried out to form compound 3. In one embodiment, the amount of catalyst used is about 5 mol % and the amount of phosphorus ligand used is about 5 mol %. In one embodiment, compound 3 is typically obtained as a crystalline solid in about 81% yield in excellent purity (>99% AUC). In one embodiment, when the amount of catalyst used is less than about 2.5 mol % and the amount of phosphorus ligand used is less than about 2.5 mol %, reaction can be stalled 73% (AUC) after about 23 hours. In one embodiment, the addition of about 1 mol % Pd₂(dba)₃ and about 2 mol % Xantphos results in complete conversion to compound 3 after about 47 hours, which leads to about 75% yield of compound 3 (98.98% AUC) as a deep-red crystalline solid. Example 4 provides a detailed discussion of the initial experiments directed to the cross-coupling reaction.

The displacement reaction and the cross-coupling reaction both produces compound 3 (full details are in Example 1). However, a few drawbacks were identified with the cross-coupling reaction. These drawbacks are (1) the reaction kinetics are slow in THF;

(2) recharging catalyst and ligand is often required to complete the reaction;

(3) a solvent swap from THF to EtOAc is required during work-up and isolation;

(4) a charcoal treatment is necessary to remove impurities;

(5) the starting material compound 2 is used as excess and yet, there is a significant amount of compound 2 remaining after the reaction was complete.

In one embodiment, the reaction solvent is switched from THF to 2-MeTHF to try to solve the problems listed above. This allows the reaction to be conducted at a higher temperature and also simplifies the work-up since 2-Me-THF is water immiscible, and a solvent swap to EtOAc is not needed. However, this modification did not solve all of the problems listed above. Example 5 provides full details of optimizing the cross-coupling reaction.

Overall, the cross coupling reaction is slow and recharge of the catalyst and ligand is needed to complete the reaction; the isolation procedure is laborious; the removal of impurities related to 2A is challenging (see Example 9); and elevated levels of residual Palladium are present in compound 3 when prepared using the cross-coupling approach.

Purification of 7 using a Pd scavenger was required in order to meet acceptable levels of Pd in the final active pharmaceutical ingredient (see Example 10). Therefore, in the process of the invention, the displacement reaction of 1' and 2' to generate compound 3 is pursued.

Step 2: Synthesis of Compound 4

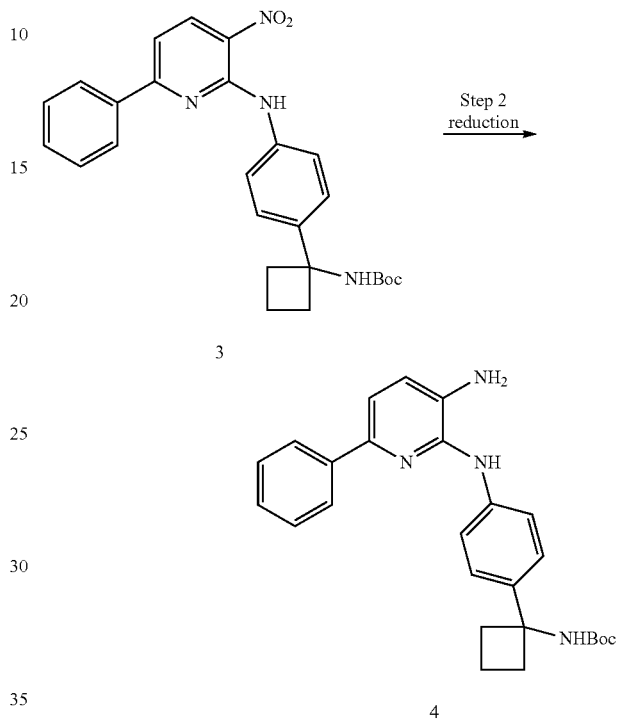

In one embodiment, the synthesis of compound 4 is via catalytic hydrogenation of compound 3 with hydrogen gas at moderate pressure. Catalytic hydrogenation of compound 3 can be carried out in a polar aprotic solvent (e.g., EtOAc, THF, 2-MeTHF) with Pd/C (e.g., 10%, 10 wt %) under typically 40 psi of hydrogen gas. Typically, after about 3 hours, the reaction is complete by HPLC analysis. In one embodiment, compound 4 can be isolated in quantitative yield as a foam by concentrating the filtrate to dryness after the catalyst is removed by filtration through Celite®. The reaction using hydrogen gas under a moderate pressure is typically high yielding. Example 6 provides other reaction conditions that were explored.

Step 3: Synthesis of Compound 6

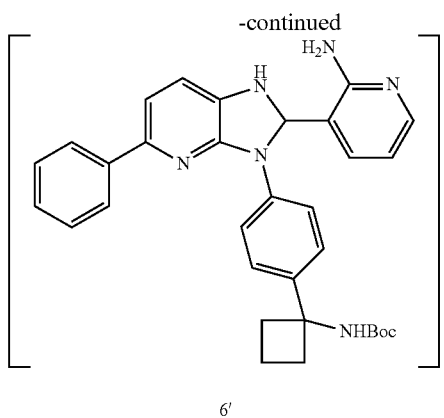

6'

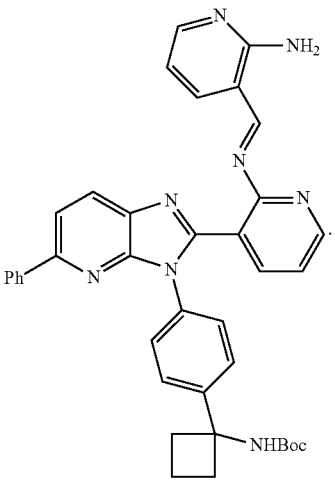

Impurity 7

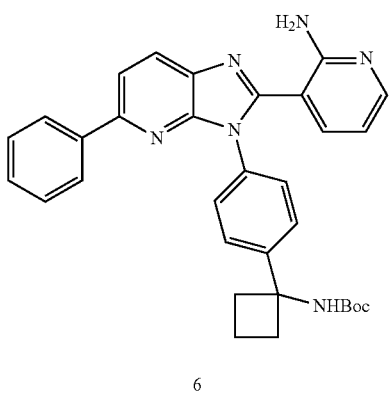

6

In one embodiment, the synthesis of compound 6 is carried out by reacting compound 4 with compound 5 (2-amino nicotinaldehyde) in the presence of an oxidant and an acid (e.g., acetic acid) in a polar protic solvent (e.g., methanol). Many optimization reactions were investigated to arrive at the conditions used in the process of the invention. See Example 7. For example, solvent such EtOH, PrOH, toluene and DMSO were investigated, but the reactions were slow. Mixtures of HOAc/MeOH at varying ratios and temperatures were explored to determine a suitable reaction condition. In one embodiment, the acid to solvent ratio of about 9:1 (v/v) afforded compound 6 in good yield. In one embodiment, the acetic acid to methanol ratio is about 9:1 (v/v). If the temperature of the reaction is elevated to about 50° C., impurity 7 can be observed:

In one embodiment, 10 volumes of AcOH/MeOH (about 9:1) at ambient temperature is employed. In another embodiment, stirring compound 4 (1.0 equiv.) and compound 5 (1.05 equiv.) in AcOH/MeOH (10 vol.) overnight at ambient temperature open to an air atmosphere affords near complete conversion to compound 6. In one embodiment, compound 4 and compound 5 are reacted in the presence of oxidant selected from the group consisting of metal acetate, metal perborate, metal chloride, palladium based catalyst, and hydrates thereof. In a further embodiment, compound 4 and compound 5 are reacted in the presence of alkali metal perborate and hydrates thereof. In a further embodiment, compound 4 and compound 5 are reacted in the presence of oxidant selected from the group consisting of copper acetate, sodium perborate, ferric chloride, palladium on carbon, and hydrates thereof. In a further embodiment, compound 4 and compound 5 are reacted in the presence of oxidant selected from the group consisting of $Cu(OAc)_2 \cdot H_2O$, $NaBO_3 \cdot 4H_2O$, $FeCl_3 \cdot 6H_2O$, and 10% Pd/C. In a further embodiment, compound 4 and compound 5 are reacted in the presence of $NaBO_3 \cdot 4H_2O$.

The isolation of compound 6 is not trivial and it required extensive studies to determine the suitable condition to isolate 6. See Example 7. In one embodiment, once the reaction mixture is complete, the reaction mixture is then concentrated (55° C.) until distillation is stopped. In one embodiment, 2-MeTHF is added followed by addition of 20% KOH to pH>13. In one embodiment, the aqueous layer is removed and the organic layer is washed with a 5% brine solution. In one embodiment, the aqueous layer after the first wash is removed and a second 5% brine wash is performed. In one embodiment, the aqueous layer after the second wash is removed. In one embodiment, IPAc (0.5 wt % 2-MeTHF) is added to the organic solution resulting in a slurry formation. In one embodiment, crude compound 6 is then filtered and washed with IPAc, IPAc/n-heptane (1/1), and then n-heptane. In one embodiment, after compound 6 is dried on the filter for 2 hours, compound 6 is transferred to a vacuum oven and dried overnight at about 40° C. In one embodiment, compound 6 is isolated in about 86% yield (accounting for solvent content), 97.3% (AUC) as a light yellow solid. In one embodiment, $^1$H NMR ($CDCl_3$) shows that the isolated compound 6 contains 0.8 wt % IPAc, 0.7 wt % 2-MeTHF, and no heptane. In another embodiment, the major impurity is the N-oxide (M+16) that is present at 2.3%.

In one embodiment, the purification of compound 6 is accomplished by dissolving 6 in DCM and eluting the dissolved 6 through a pre-packed (DCM) silica gel plug. In one embodiment, the column is then flushed with EtOAc. Two fractions are generally collected and analyzed by HPLC. In one embodiment, no N-oxide impurity is observed. In one embodiment, the fractions are combined and partially concentrated resulting in a thick slurry. In one embodiment, n-Heptane is added and the mixture is stirred for about 15 minutes. Purified compound 6 is filtered and washed with heptane and dried in a vacuum oven at about 45° C. In one embodiment, compound 6 [about 89% recovery, about 100% (AUC)] is obtained as an off-white solid after about 15 hours of drying. Typically, $^1$H NMR shows only a trace of EtOAc and no n-heptane present.

Step 2' in Scheme 1': Synthesis of Intermediate Compound 4 and then Compound 6

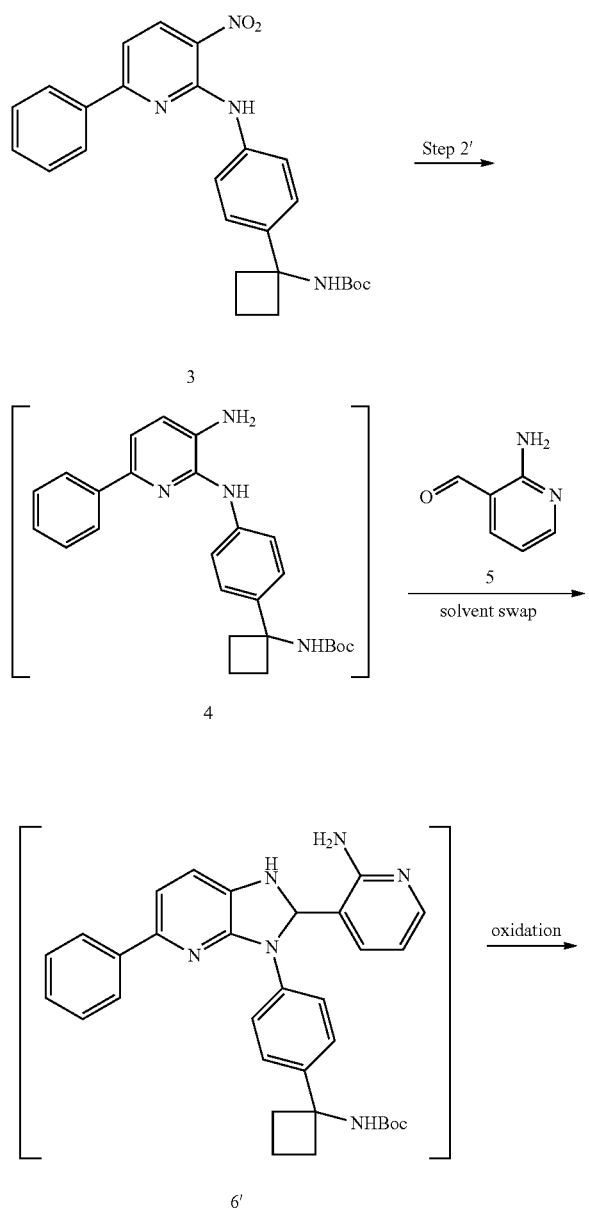

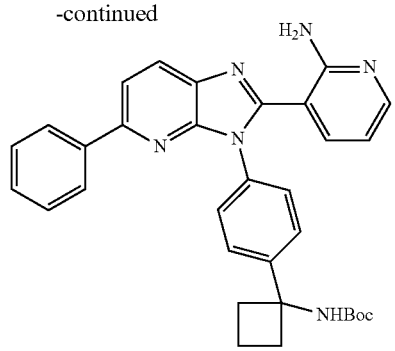

In one embodiment, the synthesis of intermediate compound 4 is via catalytic hydrogenation of compound 3 with hydrogen gas at moderate pressure. Catalytic hydrogenation of compound 3 can be carried out in a polar aprotic solvent (e.g., EtOAc, THF, 2-MeTHF) with Pd/C (e.g., 10%, 10 wt %) under typically 40 psi of hydrogen gas. Typically, after about 3 hours, the reaction is complete by HPLC analysis. In one embodiment, intermediate compound 4 is not isolated before reaction with compound 5. The reaction using hydrogen gas under a moderate pressure is typically high yielding. In one embodiment, the polar aprotic solvent is replaced with a polar protic solvent.

In one embodiment, the synthesis of compound 6 is carried out by reacting compound 4 with compound 5 (2-amino nicotinaldehyde) in the presence of an oxidant and an acid (e.g., acetic acid) in a polar protic solvent (e.g., methanol). Many optimization reactions were investigated to arrive at the conditions used in the process of the invention. See Example 7. For example, solvent such EtOH, PrOH, toluene and DMSO were investigated, but the reactions were slow. Mixtures of HOAc/MeOH at varying ratios and temperatures were explored to determine a suitable reaction condition. In one embodiment, the acid to solvent ratio of about 9:1 (v/v) afforded compound 6 in good yield. In one embodiment, the acetic acid to methanol ratio is about 9:1 (v/v). If the temperature of the reaction is elevated to about 50° C., impurity 7 can be observed:

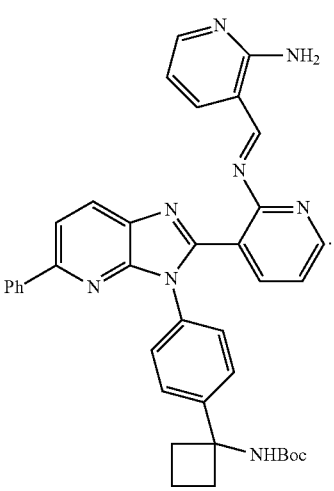

Impurity 7

In one embodiment, 10 volumes of AcOH/MeOH (about 9:1) at ambient temperature is employed. In another embodiment, stirring compound 4 (1.0 equiv.) and compound 5 (1.05 equiv.) in AcOH/MeOH (10 vol.) overnight at ambient temperature open to an air atmosphere affords near complete conversion to compound 6. In one embodiment, compound 4 and compound 5 are reacted in the presence of oxidant selected from the group consisting of metal acetate, metal perborate, metal chloride, palladium based catalyst, and hydrates thereof. In a further embodiment, compound 4 and compound 5 are reacted in the presence of alkali metal perborate and hydrates thereof. In a further embodiment, compound 4 and compound 5 are reacted in the presence of oxidant selected from the group consisting of copper acetate, sodium perborate, ferric chloride, palladium on carbon, and hydrates thereof. In a further embodiment, compound 4 and compound 5 are reacted in the presence of oxidant selected from the group consisting of $Cu(OAc)_2 \cdot H_2O$, $NaBO_3 \cdot 4H_2O$, $FeCl_3 \cdot 6H_2O$, and 10% Pd/C. In a further embodiment, compound 4 and compound 5 are reacted in the presence of $NaBO_3 \cdot 4H_2O$.

The isolation of compound 6 is not trivial and it required extensive studies to determine the suitable condition to isolate 6. See Example 7. In one embodiment, once the reaction mixture is complete, the reaction mixture is then concentrated (55° C.) until distillation is stopped. In one embodiment, 2-MeTHF is added followed by addition of 20% KOH to pH>13. In one embodiment, the aqueous layer is removed and the organic layer is washed with a 5% brine solution. In one embodiment, the aqueous layer after the first wash is removed and a second 5% brine wash is performed. In one embodiment, the aqueous layer after the second wash is removed. In one embodiment, IPAc (0.5 wt % 2-MeTHF) is added to the organic solution resulting in a slurry formation. In one embodiment, crude compound 6 is then filtered and washed with IPAc, IPAc/n-heptane (1/1), and then n-heptane. In one embodiment, after compound 6 is dried on the filter for 2 hours, compound 6 is transferred to a vacuum oven and dried overnight at about 40° C. In one embodiment, compound 6 is isolated in about 86% yield (accounting for solvent content), 97.3% (AUC) as a light yellow solid. In one embodiment, $^1$H NMR (CDCl$_3$) shows that the isolated compound 6 contains 0.8 wt % IPAc, 0.7 wt % 2-MeTHF, and no heptane. In another embodiment, the major impurity is the N-oxide (M+16) that is present at 2.3%.

In one embodiment, the purification of compound 6 is accomplished by dissolving 6 in DCM and eluting the dissolved 6 through a pre-packed (DCM) silica gel plug. In one embodiment, the column is then flushed with EtOAc. Two fractions are generally collected and analyzed by HPLC. In one embodiment, no N-oxide impurity is observed. In one embodiment, the fractions are combined and partially concentrated resulting in a thick slurry. In one embodiment, n-Heptane is added and the mixture is stirred for about 15 minutes. Purified compound 6 is filtered and washed with heptane and dried in a vacuum oven at about 45° C. In one embodiment, compound 6 [about 89% recovery, about 100% (AUC)] is obtained as an off-white solid after about 15 hours of drying. Typically, $^1$H NMR shows only a trace of EtOAc and no n-heptane present.

Step 4 in Scheme 1 or Step 3' in Scheme 1': Synthesis of Compound 7

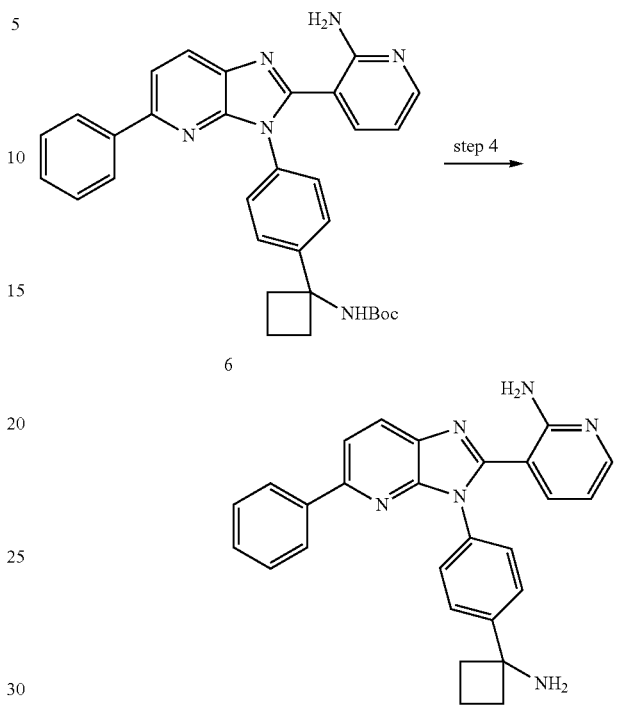

The conversion of compound 6 to compound 7 was investigated using different acids such as TFA and in different solvent such as DCE, anisole, and IPA. (See Example 8). The optimization studies in Example 8 indicate that dichloromethane (DCM) and methanesulfonic (MSA) acid are suitable for conversion of compound 6 to compound 7.

In one embodiment, the synthesis of compound 7 is carried out by dissolving compound 6 in DCM and MSA was added over about 15 minutes (e.g., $T_{max}$=29° C.). In another embodiment, the ratio of MSA to compound 6 is about 5:1. In one embodiment, after about 2 hours, a thick slurry is present and water is added and the mixture is stirred for about 40 minutes. The aqueous layer is removed and water is added to extract the DCM layer. The aqueous layers are combined and then washed with DCM. In one embodiment, DCM is added to the aqueous layer and the mixture is made basic (e.g., with 6 N NaOH) to pH=13. The layers are separated and the aqueous layer is reextracted with DCM. The organic layer is typically dried over Na$_2$SO$_4$ and then concentrated down, resulting in the precipitation of solids. In one embodiment, the mixture is concentrated further and IPAc is added. In one embodiment, the mixture is reduced again and IPAc is added. Additional IPAc is added and the slurry is stirred overnight. In one embodiment, compound 7 is filtered, washed with IPAc, and dried in a vacuum oven (e.g., >28 in Hg) at about 45° C. for about 2 days. Compound 7 (about 87% yield, about 99.8% AUC) is obtained as a light yellow solid. In one embodiment, $^1$H NMR (CDCl$_3$) shows that isolated 7 contains IPAc (0.5 wt %) and DCM (<0.1 wt %).

Synthesis of the Starting Compounds 1, 1', 2 and 2'

The preparations of compounds 1, 1', 2 and 2' required extensive screening and optimization to arrive at a safe and high yielding procedure. Details of the studies to prepare these starting compounds are provided in Example 9.

Purification of 6 and 7 with High Pd Level

In one embodiment, compound 3 is prepared via the cross-coupling route has a high level of residual palladium (e.g., 1888 ppm). If this batch of compound 3 is carried through the subsequent steps to compound 6, the level of residual palladium for compound 6 in this batch is still typically high (e.g., 281 ppm). Therefore, in order to afford compound 7 having less than 20 ppm residual palladium, experiments on purification of the palladium from compound 6 and 7 free base were initiated to identify a method to remove the residual palladium. See Example 10.

In one embodiment, the scavengers are more efficient in the case of compound 7 free base over compound 6. In another embodiment, the scavenger is QuadraSil MP. In another embodiment, QuadraSil MP is used as a scavenger to remove palladium from a sample of compound 7.

Definitions

For convenience, certain terms used in the specification, examples and appended claims are collected here.

The process of the invention refers to any of the process of described in this application.

HPLC is High Performance Liquid Chromatography.
ACN or MeCN is acetonitrile.
DMA is dimethylacetamide.
MTBE is methyl tert-butyl ether.
EtOH is ethanol.
DMSO is methylsulfoxide.
DPPA is diphenylphosphoryl azide
NMR is Nuclear Magnetic Resonance
MS is Mass Spectrometry.
RB is round bottom.
DI is deionized water.
DCM is dichloromethane.
DCE is 1,2-dichloroethane.
TFA trifluoroacetic acid.
MSA is methanesulfonic acid.
THF is tetrahydrofuran.
2-MeTHF is 2-methyltetrahydrofuran.
EtOAc is ethyl acetate.
IPAc isopropyl acetate.
IPA is isopropyl alcohol
Xantphos 4,5-Bis(diphenylphosphino)-9,9-dimethylxanthene.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1: Preparation of Compounds 1, 1', 2, 2', 3, 4, 6 and 7

Preparation of 1

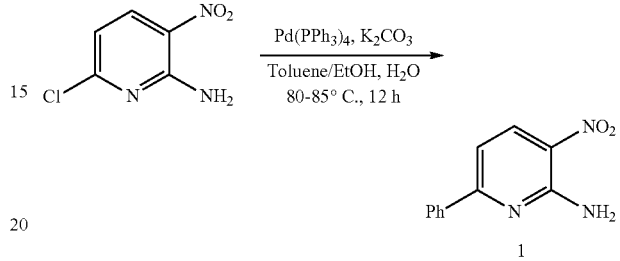

A 100 L jacketed reactor equipped with temperature probe, argon inlet and reflux condenser was charged with toluene (30 L, 30 vol.), EtOH (6 L, 6 vol.), 2-amino-3-nitro-6-chloro-pyridine (1.0 kg, 5.76 mol.), phenylboronic acid (772 g, 6.34 mol.) followed by a solution of $K_2CO_3$ (1.75 kg, 12.67 mol) in DI water (6.0 L, 6 vol.). The resulting mixture was stirred at room temperature for 10 minutes. The reaction mixture was degassed with argon for 30 minutes before $Pd(PPh_3)_4$ (67.1 g, 1 mol) was added to the reaction mixture and then resulting mixture was degassed for additional 10 minutes. The reaction was then heated to 80-85° C. The reaction was deemed complete by HPLC in 12 hours. The reaction was cooled to room temperature and diluted with water (10 L, 10 vol.). The organic layer was removed and the aqueous layer was extracted with MTBE (2×10 L, 20 vol.). Combined organic layers were treated with charcoal and heated to 50° C. for 1 hour. The hot solution was filtered through a Celite® bed and washed the bed with hot (~50° C.) MTBE (2 L, 2 vol.) and dried the filtrate over sodium sulfate. The organic layer was concentrated under reduced pressure at below 50° C. to give dark brown solid (1.094 kg, 88.9%). The crude compound was triturated in heptanes (3.5 L, 3.5 vol.) for 3 hours, filtered off the solids, washed with heptanes (1.5 L, 1.5 vol.) and dried to afford 1 (980.0 g, 79.6%, 89.6% purity) and compound was characterized by $^1$H NMR (CDCl$_3$) and MS.

Preparation of 1'

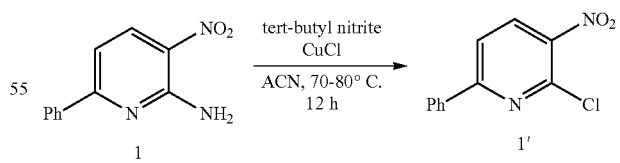

A 3 L, three-neck RB flask equipped with a stirrer, argon inlet, reflux condenser and thermometer was charged with acetonitrile (1500 mL), Cu(I)Cl (59.7 g, 604.0 mmol) and tert-butyl nitrite (112.2 mL, 929 mmol). The mixture was heated to 40-50° C. and 1 (100.0 g, 467.3 mmol) was then added in portions. The resulting mixture was stirred at 40-50° C. for one hour and the reaction was deemed complete by HPLC. The reaction was quenched with aqueous ammonium chloride solution (2.0 L, 20 vol.) and diluted with MTBE (2.0 L, 20 vol.). The organic layer was removed and the aqueous layer was extracted with MTBE (2×1 L, 20 vol.). The combined organic layers were treated with charcoal and heated to 50° C. The hot solution was filtered through a pad of Celite® and the Celite® pad was washed with hot MTBE (1 L, 1 vol.), dried over sodium sulfate and concentrated to give crude 1' (61.1 g, 60.7%). The crude compound was triturated in methanol (183 mL, 3 vol. with respect to crude weight) for 15 minutes. The solids were filtered, washed with methanol (30 mL) and dried to obtain 1' (48.0 g, 43.4%). This was triturated with heptanes (100 mL, 1 vol.) at ambient temperature for one hour, filtered and washed with heptanes (25 mL) and dried to give 1' as yellow solid (42.02 g, 38.5%, 97.6% purity). The compound was characterized by $^1$H NMR (CDCl$_3$) and MS. Additional lots were prepared using this procedure and the results can be seen in Table 1.

TABLE 1

Preparation of 1' From 1

| entry | Input | Output | Purity by HPLC (AUC) | Conditions |
|---|---|---|---|---|
| 1 | 40.0 g | 14.8 g (33.0%) | 98.9% | ACN (25 vol.), tert-butyl nitrite (1.5 equiv), Cu(I)Cl (1.2 equiv) (55-60° C.). |
| 2 | 100.0 g | 42.02 g (38.5%) | 97.6% | ACN (15 vol.), tert-butyl nitrite (2.0 equiv), Cu(I)Cl (1.3 equiv) (55-60° C.). |
| 3 | 200.0 g | 61.5 g (28.2%) | 98.0% | ACN (15 vol.), tert-butyl nitrite (2.0 equiv), Cu(I)Cl (1.3 equiv) (55-60° C.). |

Preparation of 1a from 1

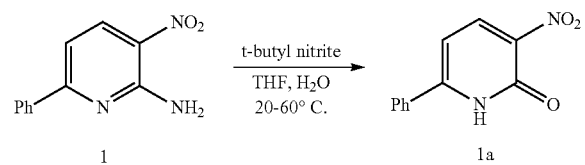

A 3 L, three neck round bottom flask equipped with a stirrer, argon inlet, reflux condenser and thermometer was charged with 1 (200.0 g, 929.3 mmol), THF (1600 mL, 8 vol.) and DI water (400 mL, 2 vol.). The resulting mixture was stirred for 10 minutes at room temperature, then tert-butyl nitrite (110.3 mL, 929.3 mmol, 1.0 equiv.) was added over a period of 10 minutes. The reaction mixture was heated to 55-60° C. and stirred for 14 hours (compound 1a was found to crash out of solution as a solid during the course of the reaction). After 14 hours, HPLC analysis showed the presence of ~18.7% of 1, then the reaction mixture was cooled to 40° C. and tert-butyl nitrite (110.3 mL, 929.3 mmol, 1.0 equiv.) was added, then heated to 60° C. and stirred for 20 hours. After 34 hours HPLC showed 5% of 1. To the reaction mixture was then added 0.1 equiv of tert-butyl nitrite (11.1 mL, 92.6 mmol, 0.1 equiv.) and stirred at 60° C. for 6 hours. After 40 hours, the HPLC showed still 5% of the staring material, then the reaction was cooled to room temperature and the solids were filtered, washed the solids with EtOAc (400 mL, 2 vol.) and dried to afford compound 1a (148.1 g; 73.8%, 95.7% purity) and was characterized by $^1$H NMR (DMSO-d$_6$) and MS.

Preparation of 1a from 1b and Phenylboronic Acid

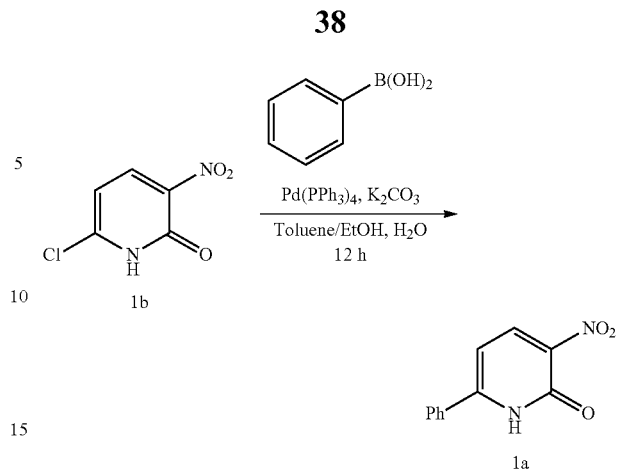

A 100 L jacketed reactor equipped with a temperature probe, nitrogen inlet and reflux condenser was charged with toluene (27.0 L, 30 vol.) and EtOH (5.4 L, 6 vol.) followed by 6-chloro-3-nitropyridin-2(1H)-one (900.0 g, 5.15 mol) and phenyl boronic acid (640.4 g, 5.253 mol). The mixture was stirred at ambient temperature for 15 minutes before a solution of K$_2$CO$_3$ (173.9 g, 11.33 mol) in DI water (5.4 L, 6 vol.) was added. The reaction mixture was degassed with argon for 30 minutes at room temperature. Tetrakis triphenylphosphine palladium (178.2 g, 3 mol %) was added and the solution was heated to 95-100° C. (internal temperature was 77-79° C.) and stirred for 3 hours. After 3 hours HPLC showed 2.8% of starting material and another single impurity (15.3%, 1.17 RRT). The reaction was maintained for 3 hours at same temperature. After 6 hours, there was no progress in the reaction and the mixture was cooled to room temperature, degassed for 30 minutes, and another 5.0 g of tetrakis triphenylphosphine palladium was added and the solution was heated to 95-100° C. Reaction was deemed complete after one hour by HPLC. The reaction mixture was cooled to room temperature, the reaction was diluted with DI water (11.7 L, 13 vol.) followed by EtOAc (18.0 L, 20 vol.) and stirred for 1 hour. The two layers were separated, leaving the solids in aqueous layer. The aqueous layer was extracted with EtOAc (13.5 L, 15 vol.). The combined aqueous layers were neutralized pH to 6.2-6.8 with 3N HCl, when more solids precipitated out, the solids were filtered off, washed with water (2×2.5 L, 5 vol.) and dried under vacuum at 45-50° C. for 48 hours, to furnish 1a (761.1 g, 68.9% yield, 78.0% purity) as yellow solid. The compound was characterized by $^1$H NMR (DMSO-d$_6$) and MS.

The combined organic (ethyl acetate) layers were extracted with 3N NaOH (15 L), when solids were formed. The organic layer was separated. The aqueous layer was then acidified pH to 5-6 with 3N HCl, when more solids were precipitated out, which were filtered off and washed with DI water (2.0 L) and dried to obtain compound 1a (140.0 g, 12.7%, 93.8% purity, 2$^{nd}$ crop).

Preparation of 1' from 1a

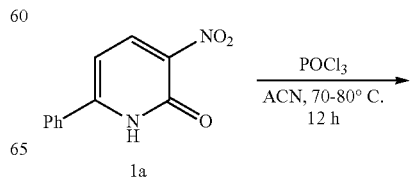

-continued

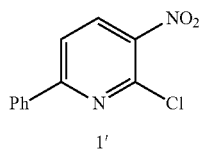

1'

A 20 L jacketed reactor equipped with temperature probe, nitrogen inlet and reflux condenser was charged with acetonitrile (6.0 L, 5 vol.) followed by 1a (1.2 kg, 5.5 mol.) and then POCl₃ (1.2 L, 1 vol.) was added over a period of 5 minutes. The reaction mixture was slowly heated to 70-80° C. for 12-15 hours before the reaction was deemed complete by HPLC. The reaction mixture was cooled to room temperature and quenched into ice water (24 L) below 10° C. and basified to pH: 8-9 with 6 N NaOH solution (~7.2 L) below 15° C. The precipitated solids were filtered off and washed with DI water (3.6 L, 3 vol.) and dried to obtain 1' as a dark brown solid (786 g, 60.8%). The crude 1' was dissolved in EtOAc (12 L, 10 vol.) [Note: some insoluble solids were observed] and stirred for 30 minutes. The solution was filtered through Celite® bed and washed with EtOAc (3 L, 3 vol.). The organic solution was treated with charcoal, filtered off through a pad of Celite® and the Celite® pad was washed with ethyl acetate (3 L, 3 vol.). The resulting filtrate was concentrated to dryness to furnish 1' (688.3 g, 52.9%, 98.07% purity). The compound was characterized by $^1$H NMR (CDCl₃) and MS. The batch summary for the preparation of 1' from 1a can be seen in Table 2 and 3.

TABLE 2

1' Produced Using 1a and POCl₃

| Batch # | Input | Output | Purity (AUC) | Conditions |
|---|---|---|---|---|
| 1 | 78.0 g | 51.3 g (60.4%) | 99.1% | a) Acetonitrile (5 vol.)/POCl₃ (1 vol.) b) During the reaction the impurity at 1.17 RRT was not observed. |
| 2 | 900.0 g | 475.1 g (48.1%) | 98.7% | a) Acetonitrile (5 vol.)/POCl₃ (1 vol.) |
| 3 | 1.2 kg | 688.3 g (52.9%) | 98.07% | a) Acetonitrile (5 vol.)/POCl₃ (1 vol.) |
| 4 | 1.2 kg | 618.0 g (47.3%) | 98.5% | a) Acetonitrile (5 vol.)/POCl₃ (1 vol.) |

Slurry Blend of 1' in Methanol

Compound 1' [1.78 kg (475.0 g, Batch 2; 688.0 g, Batch 3; 617.0 g, Batch 4)] was blended with methanol (1.8 L, 1 vol.) slurry at 20° C. The slurry was stirred for 30 minutes at 20° C. before being filtered. The filtered solids were washed with methanol to afford 1' (1.71 kg, 96% yield, 99.5% AUC)

TABLE 3

Results of the Slurry Blend of 1'

| Input | Output | Purity by (HPLC % AUC) | Remarks |
|---|---|---|---|
| 1.78 kg (475 g, Batch 2) (688 g, Batch 3) (617 g, Batch 4) | 1.71 kg (Recovery 96%) | 99.5% | a) The purity of the compound was increased to 99.5% (AUC) from ~98.0%. |

Preparation of B

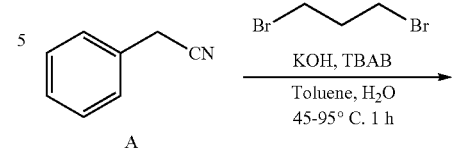

A

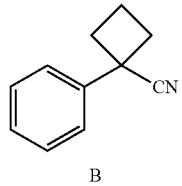

B

A suspension of powdered potassium hydroxide (536 g, 9.56 mol, 5.6 equiv.) in toluene (1.54 L) and water (154 mL) was warmed to 45° C. Tetrabutylammonium bromide (28 g, 0.85 mol, 0.05 equiv.), and 1,3-dibromopropane (379 g, 1.88 mol, 1.1 equiv.) were then added, followed by the drop wise addition of a solution of A (200 g, 1.7 mol, 1.0 equiv.) in toluene (500 mL) over 42 minutes. During the addition the temperature rose to 95° C. and the mixture was then heated to reflux when the addition of A was complete. The resulting pink slurry was stirred at this temperature for 1 hour at which time the reaction was deemed complete by HPLC analysis. The mixture was then cooled to 20-25° C. and filtered over a pad of Celite®. The solids were washed with toluene (1.0 L) and the resulting filtrate was washed with water (2×300 mL), brine (150 mL), dried over MgSO₄, filtered, and concentrated to afford crude B (263 g) as an orange oil. The product was then purified by vacuum distillation (b.p. 105° C./750 millitorr) to afford B [140 g, 52%, 97.7% (AUC)] as a colorless liquid. The main impurity present was identified as B2 (2.3% AUC) (See Example 9, synthesis of B for details).

Preparation of C

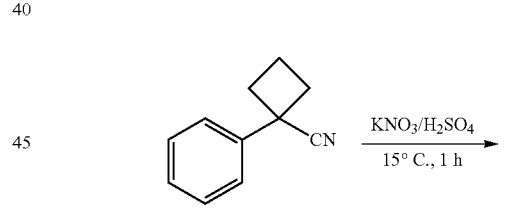

B

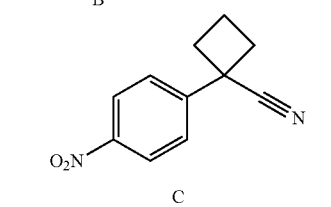

C

Solid KNO₃ (17.0 g, 0.17 mol, 1.06 equiv.) was added in portions to H₂SO₄ (100 mL) keeping the temperature <15° C. After stirring for 15 minutes, B (25.0 g, 0.16 mol, 1.0 equiv.) was added keeping the temperature <15° C. After one hour, the mixture was sampled and analyzed by HPLC showing the reaction to be complete. The mixture was then poured over ice and extracted with DCM (200 mL). The organic layer was washed with 1 M NaOH, brine, and then dried over MgSO₄. After concentration, C [32.1 g, 99%, 95.5% (AUC)] was isolated as an orange/brown solid. $^1$H NMR (CDCl$_3$) suggested that the material was slightly less pure than what was determined by HPLC.

Preparation of D

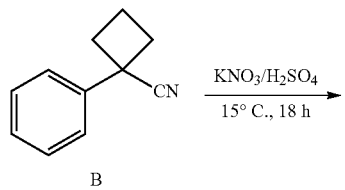

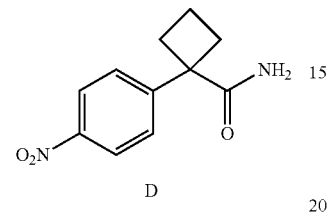

Solid KNO$_3$ (318.1 g, 3.18 mol, 1.06 equiv.) was added in portions to H$_2$SO$_4$ (1.9 L) keeping the temperature <15° C. After stirring for 15 minutes, compound B (471.3 g, 3.0 mol, 1.0 equiv.) was added over 75 minutes keeping the temperature <20° C. After 2 hours, the mixture was analyzed by HPLC showing the reaction to be complete (70% of C, 30% of D). This reaction was then stirred at ambient temperature overnight at which point no C remained by HPLC analysis. The mixture was then poured onto ice (3 kg) with DCM (3 L) present. The organic layer was washed with 1 M NaOH (1.0 L), brine (500 mL), and then dried over MgSO$_4$. After concentration, heptane (1.5 L) and EtOAc (500 mL) were added and the mixture was stirred at ambient temperature for 4 hours. The solids were then filtered and dried to provide D [365.5 g, 55% over two steps, ~99% (AUC)] as a light yellow solid.

Preparation of D from C

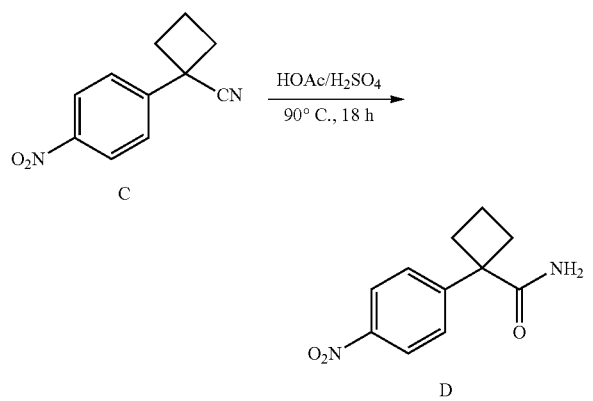

To a solution of C (40 g, 0.19 mol, 1.0 equiv.) in AcOH (520 mL) was slowly added H$_2$SO$_4$ (280 mL) resulting in a significant exotherm (25→65° C.). This mixture was then heated to 90° C. overnight at which time the reaction was deemed complete by HPLC analysis. The mixture was cooled to ambient temperature, poured onto ice and extracted with DCM. The organic layer was washed with saturated aqueous NaHCO$_3$, water, and then brine. After drying with MgSO$_4$, the solution was partially concentrated and heptane was added. Further concentration led to the precipitation of D. Filtration and washing with heptane afforded D [30.0 g, 69%, 99% (AUC)] as a light brown solid.

Preparation of E

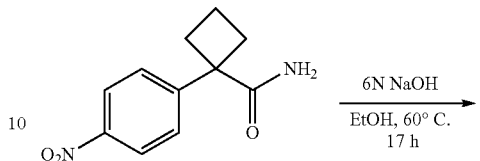

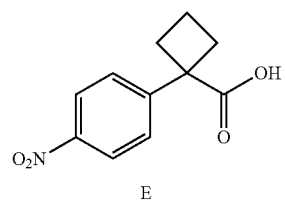

D (10.0 g, 45.4 mmol, 1.0 equiv.) was stirred in EtOH (50 mL) and 6 M NaOH (60.6 mL, 363.3 mmol, 8.0 equiv.) overnight at 60° C. After 17 hours, HPLC analysis showed the reaction was complete. The mixture was cooled to ambient temperature, diluted with water (60 mL), and partially concentrated to remove EtOH. After concentration, the mixture was washed with DCM (2×100 mL) and the aqueous layer was then acidified with aqueous 6 M HCl. The acidic aqueous layer was extracted with DCM (3×100 mL) and the combined organics were washed with brine and dried over MgSO$_4$. After concentration, E [10.2 g, 100%, 95% (AUC)] was isolated as a brown solid.

Preparation of H

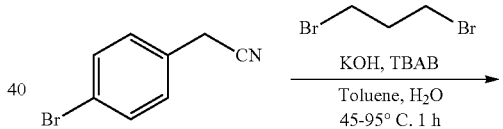

A suspension of powdered potassium hydroxide (801 g, 14.3 mol, 5.6 equiv.) in toluene (3.85 L, 7.7 vol.) and water (385 mL, 0.77 vol.) was warmed to 50° C. Tetrabutylammonium bromide (41.1 g, 2.81 mol, 0.05 equiv.) and 1,3-dibromopropane (566 g, 2.81 mol, 1.1 equiv.) were then added. Next, a solution of G (500 g, 2.6 mol, 1.0 equiv.) in toluene (1.25 L, 2.2 vol.) was added slowly over 30 minutes while maintaining temperature at 50-85° C. The resulting purple slurry was heated to reflux (100° C.) and stirred at this temperature for 1 hour, at which time HPLC analysis indicated complete disappearance of G. The mixture was cooled to 70° C. and heptane (5.2 L) was added. The resulting slurry was then cooled to ambient temperature and filtered over a pad of Celite®. The solids (a significant amount) were washed with toluene (2.0 L) and the resulting filtrate was washed with water (3×500 mL), brine (500 mL), dried over MgSO₄, filtered, and concentrated. This provided crude product H [519 g, 86%, 86% (AUC)] as a red oil.

Preparation of I

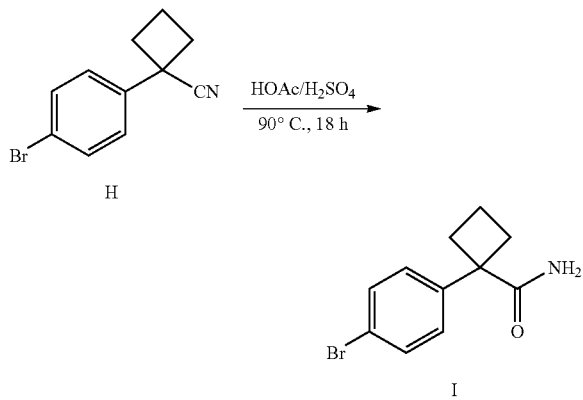

To a solution of H (200 g, 0.85 mol, 1.0 equiv.) in AcOH (800 mL) was slowly added H₂SO₄ (400 mL) resulting in a significant exotherm (25→40° C.). This mixture was heated to 90° C. overnight at which time HPLC analysis indicated that the reaction was complete. The mixture was cooled to ambient temperature and then slowly added into a mixture of ice water (3.0 L) and dichloromethane (2.0 L). The biphasic mixture was diluted with additional dichloromethane (3.0 L) and the acidic aqueous layer was separated. The organic layer was washed with water (2×2.5 L), aqueous 0.5 M NaOH (2×2.0 L), and then with brine (500 mL). The organic layer was dried over MgSO₄, filtered, and concentrated to provide crude I (195 g) as a brown oil. The crude I was purified by column chromatography on silica gel using 80% EtOAc/heptane to afford I [159 g, 74% from G, >99% (AUC)] as a white solid.

Preparation of 2

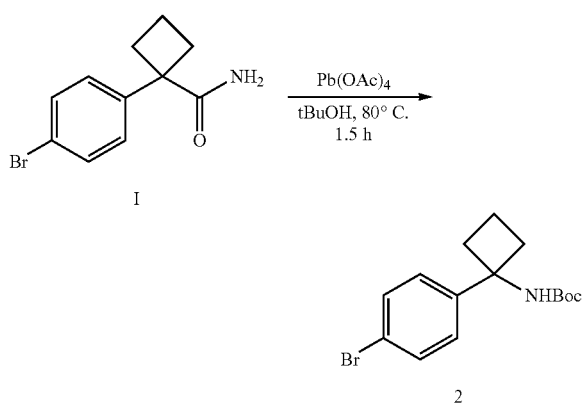

To a 3 L three-neck flask was added I (250 g, 0.98 mol, 1.0 equiv.) and t-BuOH (1250 mL, 5.0 vol.). The slurry was heated to 65° C. and stirred until all of the solids had dissolved (about 10 minutes). Pb(OAc)₄ (40.1 g, 1.13 mol, 1.15 equiv.) was added carefully in portions over 35 minutes while maintaining temperature <75° C. When the Pb(OAc)₄ addition was complete, the slurry was stirred at 80° C. for 80 minutes, at this point the reaction was complete by HPLC analysis. The slurry was then cooled to 25° C. and Na₂CO₃ (250 g, 1.0 weight equiv.) was added followed by MTBE (1.9 L). The slurry was stirred for 30 minutes and then the solids were removed by filtration through a pad of Celite®. The filtrate was washed with aqueous 10% NaHCO₃ (3×2.0 L), 10% brine (500 mL), dried over MgSO₄, filtered, and concentrated to give crude 2 [301 g, 94%, 89% (AUC)] as a lavender solid. The crude 2 was purified by re-slurry in 10/90 MTBE/heptane (5.0 vol.) to provide 2 [270 g, 84%, 94% (AUC)] as an off-white solid. 2 [270 g, 0.83 mol, 94% (AUC)] was then re-slurried in 1/1 acetonitrile/water (5.0 vol.) at ambient temperature for 22 hours. The solids were filtered and dried to yield compound 2 [240 g, 89% recovery, 95.2% (AUC)] as a white solid.

This material was then combined with other lots of 2 and purified by eluting through a plug of silica (packed and eluted using 1/99 MeOH/DCM). The rich fractions were then concentrated to dryness (525 g of 2) and blended by slurrying in MTBE (2.0 vol.) and heptane (6.0 vol.) at ambient temperature to obtain a uniform lot. This provided 2 [513 g, 97.2% (AUC)] as a white solid.

Preparation of D

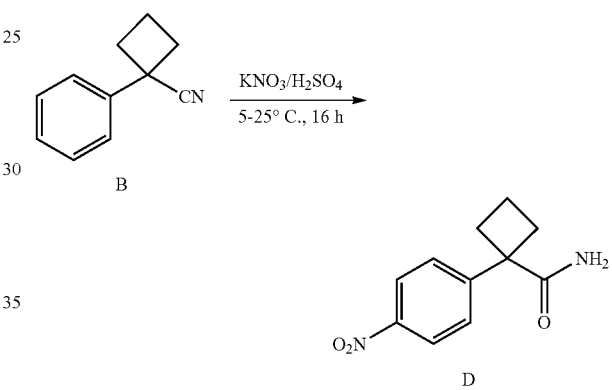

A 20-L jacketed reactor equipped with temperature probe, nitrogen inlet, reflux condenser and addition funnel was charged with concentrated H₂SO₄ (14 L, 4 vol.) and the mixture was cooled to 5-6° C. and KNO₃ (3.183 kg, 23.6 mol) was added in portions maintaining a temperature between 10-15° C. After stirring the resulting slurry for 15 minutes, B (3.5 kg, 22.27 mol) was added over a period of 90 minutes keeping the internal temperature between 10-20° C. The reaction mixture was then warmed to ambient temperature and stirred for 16 hours when the deemed complete by HPLC analysis. The reaction mixture was then poured into a mixture of chilled water (~5° C.) (35 L, 10 vol.) and DCM (35 L, 10 vol.) maintaining a temperature <15° C. The organic layer was separated and the aqueous layer was extracted twice with DCM [21 L (6 vol.) and 14 L (4 vol.)] The combined organic layers were washed with 1N NaOH (35 L, 10 vol.), brine (1.75 L, 0.5 vol.) and dried over anhydrous Na₂SO₄. The organic layer was concentrated to give D as an off-white solid (3.61 kg, 72.7% yield, 83.1% AUC).

Purification of D

Crude D (3.6 kg) was suspended in MTBE (7 L, 2 vol.) and stirred at ambient temperature for 30 minutes. The solids were then filtered, washed with MTBE (700 mL, 0.2 vol.) and dried under vacuum to afford D (2.65 kg, 54.2%, 98.3% purity) as an off-white solid.

Preparation of F from D

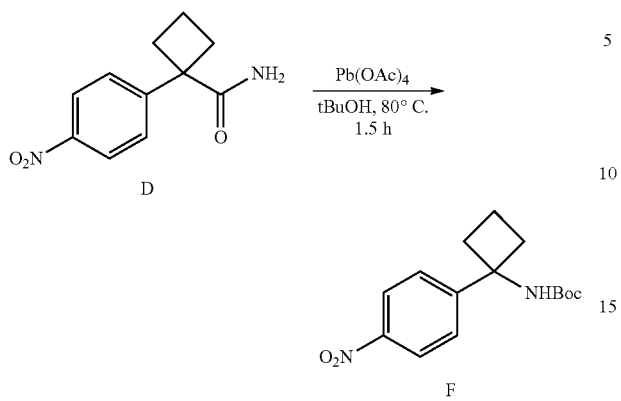

To a slurry of D (30 g, 136.2 mmol, 1.0 equiv.) in t-BuOH (230 mL, 6.0 vol.) at 75° C. was added Pb(OAc)$_4$ (69.5 g, 156.7 mmol, 1.15 equiv.) in four portions over 5 minutes. The slurry was then heated to 80° C. for 90 minutes, at which time HPLC analysis indicated that the reaction was complete (no D remained). The slurry was then cooled to 25° C. and Na$_2$CO$_3$ (30 g, 1.0 weight equivalent) was added followed by MTBE (200 mL). The slurry was stirred for 30 minutes and then the solids removed by filtration through a pad of Celite®. The filtrate was washed with aqueous 10% NaHCO$_3$ (3×200 mL), brine, dried over MgSO$_4$, filtered, and concentrated to give crude F [34.0 g, 86%, 92.5% (AUC)] as an off-white solid. $^1$H NMR (CDCl$_3$) was consistent with the desired product. This material was then used "as-is" in the next step without further purification.

Preparation of F from E

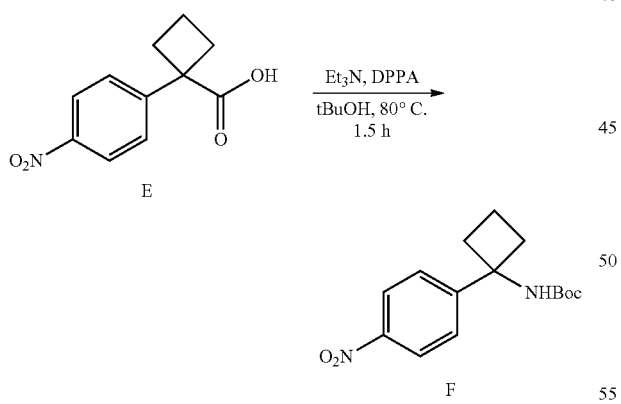

To a solution of E (2.0 g, 9.0 mmol, 1.0 equiv.) in t-BuOH (40 mL, 20 vol.) was added Et$_3$N (1.10 g, 10.9 mmol, 1.2 equiv.). This solution was heated to 75° C. at which time DPPA (2.71 g, 9.9 mmol, 1.09 equiv.) was added drop wise over 5 minutes. After stirring overnight at 81° C., the reaction was complete by HPLC analysis (no E remained) and then cooled to ambient temperature. The reaction was concentrated to dryness and analyzed by $^1$H NMR using an internal standard (dimethyl fumarate in CDCl$_3$). Based on this analysis, the overall yield of F was found to be 78%.

Preparation of F

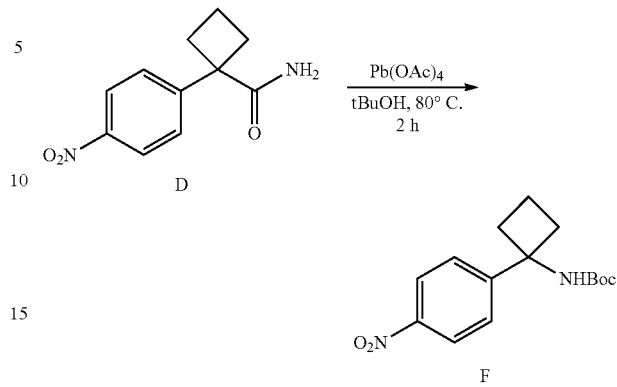

In to a 20-L clean and dry jacketed reactor equipped with reflux condenser, temperature probe and nitrogen inlet were charged with D (1.85 kg, 8.174 mol, 98.3% pure) in t-BuOH (9.25 L, 5 vol.) and the resulting mixture was heated to 50-55° C. and stirred for 45 minutes. To this mixture Pb(OAc)$_4$ (4.2 kg, 9.400 mol) was added in four equal portions and the resulting slurry was heated to 80° C. for two hours. After two hours the reaction was deemed complete by HPLC analysis. The reaction mixture was cooled to ~25° C. and Na$_2$CO$_3$ (1.85 kg, 17.002 mol) was added, followed by MTBE (10 L, 5.5 vol.). The mixture was stirred for 30 minutes, and then the solids were removed by filtration through a Celite® bed. The Celite® pad was washed with MTBE (5 L, 2.5 vol.). The filtrate was then washed with aqueous 10% NaHCO$_3$ solution (20.0 L, 10 vol.), brine (5 L, 2.5 vol.), dried over anhydrous Na$_2$SO$_4$ and concentrated under reduced pressure to give crude F (1.9 kg, 75.8% yield, 96.1% AUC) as an off-white solid.

Purification of F

Crude F (1.9 kg) was dissolved in EtOH (15.4 L, 8 vol.) at 45° C. and stirred for 15 minutes. DI water (11.2 L, 6 vol.) was slowly added in portions at a rate to maintain an internal temperature of 45° C. The resulting white suspension was stirred for two hours at ambient temperature. The slurry was then filtered, the solid was washed with 4:3 ethanol-water mixture (2 vol.) and dried under vacuum at 40° C. to afford F (1.61 kg, 65.6% yield, 99.4% AUC) as an off-white solid.

Preparation of 2'

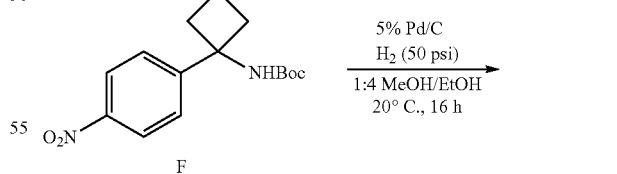

A solution of F (29 g, 99.2 mmol, 1.0 equiv.) in 20/80 MeOH/EtOH (290 mL, 10 vol.) was added to a glass pressure vessel containing 5% Pd/C (1.45 g, 5 wt % loading, 50% wet catalyst). This suspension was placed under H$_2$ (45 psi) and stirred at ambient temperature for 16 hours. After 16 hours, the reaction was complete by HPLC analysis and the mixture was filtered through a pad of Celite®. The filtrate was concentrated to give crude 2' (34 g) as a brown oil. The crude 2' was then purified by column chromatography (1:1 EtOAc/heptane on silica gel) to provide 2' [30.4 g, 100%, 97.7% (AUC)] as a viscous yellow oil. The sole impurity in this lot of compound 2' was the isopropylcarbamate derivative of 2' (2.3% AUC).

Preparation of 2'

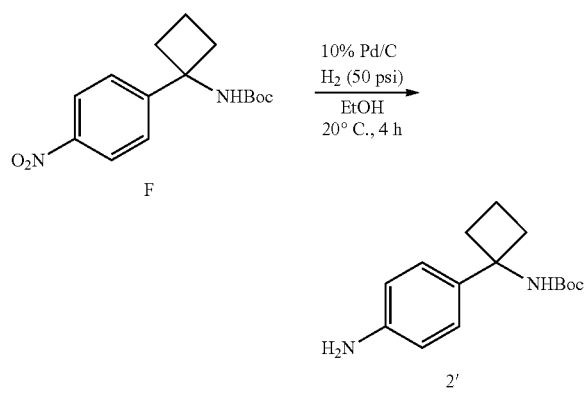

A 2-L stainless steel autoclave reactor equipped with temperature probe was charged with EtOH (5.0 L, 10 vol.) followed by F [500.0 g, 1.71 mol, 99.4% purity] and 10% Pd/C (25.0 g, 5 wt %). The reactor was flushed with nitrogen before hydrogen was filled to 45-50 psi and stirred at ambient temperature. After 4 hours reaction was deemed complete by HPLC. The reaction mixture was filtered through a pad of Celite® and the Celite® pas was washed with EtOH (2 L, 4 vol.). The filtrate was concentrated under reduced pressure to afford 2' (456.5 g, >100%) as an off-white semi solid.

Purification of 2'

Crude 2' was suspended in heptanes (1 L, 2 vol.) and stirred for two hours at ambient temperature. The slurry was filtered, the solids were washed with heptanes (250 mL, 0.5 vol.) and then dried under vacuum at 35-40° C. to afford 2' (405.0 g, 91.6% yield, 99.16% AUC) as an off-white solid.

Preparation of 3 Via Pd-Catalyzed Cross-Coupling Reaction

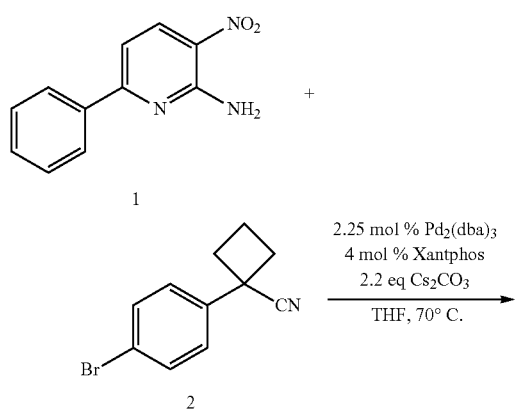

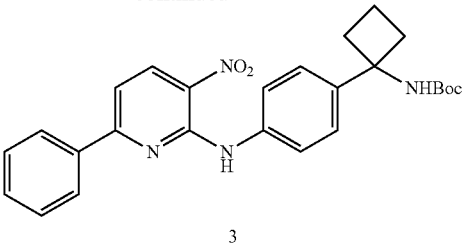

To a 1 L jacketed reactor under a positive stream of N$_2$ was added 1 (30.0 g, 139.4 mmol, 1.0 equiv.), 2 (47.75 g, 146.37 mmol, 1.05 equiv.), Cs$_2$CO$_3$ (99.92 g, 306.7 mmol, 2.2 equiv) followed by reagent grade THF (300 mL, 10 vol., KF=0.024% H$_2$O). The resulting suspension was stirred and purged with N$_2$ for 15 minutes. Pd$_2$(dba)$_3$ (1.60 g, 1.74 mmol, 1.25 mol %) and Xantphos (2.02 g, 3.49 mmol, 2.5 mol %) were then added and reaction was heated with an internal temperature of 60° C. under a positive pressure of N$_2$. At 3 hours the reaction was sampled and it was found that only 3% of product was observed. An additional amount of Pd$_2$(dba)$_3$ (1.60 g, 1.74 mmol, 1.25 mol %) and Xantphos (2.02 g, 3.49 mmol, 2.5 mol %) and were added the reaction was switched from a positive N$_2$ to a N$_2$ blanket. After 23.5 hours there was 73% of product observed by HPLC. An additional Pd$_2$(dba)$_3$ (1.40 g, 1.52 mmol, 1.0 mol %), Xantphos (1.80 g, 3.12 mmol, 2.0 mol %) and Cs$_2$CO$_3$ (50.0 g, 153.0 mmol, 1.1 equiv.) were added. HPLC at 30.5 hours shows 96% product and 3.1% of 1 remaining. The reaction was stirred for an additional 17 hours and after a total reaction time of 47 hours there was no 1 reaming. The reaction was cooled to 20° C. 500 mL of EtOAc was added followed by 250 mL of H$_2$O. After stirring the biphasic mixture for 15 minutes the organic layer was removed. The aqueous layer was extracted with 500 mL of EtOAc and the combined organics were washed with brine (500 mL) and dried over Na$_2$SO$_4$ and the filtered. The filtered solution was held at 4° C. for 45 hours until the work-up could be continued. To the dried solution was added 30.0 g of DARCO activated carbon (100 mesh) and the mixture was stirred at 45° C. for 1 hour. The mixture was filtered through a pad of Celite® and the Celite® was washed with 2×300 mL EtOAc and then concentrated in vacuo. The resulting red foam was dissolved in 275 mL of DCM and 1.0 L of heptanes was added via addition funnel over a period of 10 minutes. The resulting red solution was seeded with 3 (100 mg) and was then stirred at 20° C. for 1 hour. Heptanes (500 mL) was added over a period of 15 minutes and the resulting slurry was stirred at 20° C. for 18 hours. The concentration of 3 in solution was measured to be 5 mg/mL and the slurry was then filtered. The solid was washed with 200 mL of 5% DCM/heptanes followed by 2×400 mL heptanes. The solid was dried under vacuum at 20° C. for 16 hours to afford 38.34 g (60%, 96.5% AUC, SLI 1.1% —"M-14") of 3 as a mixture of fine and coarse crystalline orange solids. During the crystallization ~6 g of solid coated the flask. This isolation did not go as expected based on the 5 g trial experiment. The solid on the walls of the flask was dissolved in DCM as well as the 38 g that was isolated and this was combined with the mother liquors and concentrated to recover the entire amount of 3. During this failed crystallization attempt a new polymorph of 3 was discovered and allowed for a second recrystallization out of EtOAc.

Recrystallization of 3 from Cross-Coupling Reaction:

The crude solid (66.1 g) was transferred to a 500 mL flask and 250 mL (4 vol.). EtOAc was added and the mixture was heated to reflux for 30 minutes. The solution was then cooled to 50° C. and seeded with 3 and held at 50° C. for 15 minutes. The slurry was then cooled to 20° C. and stirred for 16 hours. The concentration of 3 was checked after 16 hours and found 15 mg/mL. The slurry was filtered, the filtrate was used to rinse out the flask and the rinse was added to the filter funnel. The solids were then washed with 50 mL EtOAc, 50 mL 50% EtOAc/hexanes and finally with 100 mL hexanes. The resulting dark red solid was dried under vacuum at 60° C. for 3 hours. This affords 48.4 g of 3 (75%, 98.9% AUC, SLI 1.0%—"M-14") as a dark red crystalline solid.

Preparation of 3 Via Displacement Reaction

1' (48.0 g, 1.0 equiv.), 2' (59.0 g, 1.1 equiv.), and $Na_2CO_3$ (43.4 g, 2.0 equiv.) were charged to a 2 L, 3-neck flask. DMA (310 mL, 6.5 vol.) was added and the reaction was heated to 100° C. After 18.5 hours, HPLC analysis showed the reaction to be complete. The reaction was cooled to 9° C. and 2-MeTHF (960 mL, 20 vol.) was added. 10% aqueous solution of NaCl (720 mL, 15 vol.) was added resulting in some solid formation. The mixture was stirred for one hour and then transferred to a separatory funnel (rinsed the solids forward with 100 mL water). The layers were separated and the aqueous layer ($V_{aq}$~1200 mL) was back extracted with 2-MeTHF (2×200 mL). The combined organics were then washed with 10% aqueous solution of NaCl (2×250 mL) and then analyzed by $^1$H NMR for DMA (0.3 wt %). After holding the solution overnight, an aliquot was taken out (6 mL) and was washed (3 mL) with water which resulted in a nice phase split (took >30 minutes). Water (650 mL, ½ batch size) was added and stirred for 10 minutes and then transferred to a separatory funnel and allowed to sit. After 90 minutes, a partial phase split was realized ($V_{aq}$=250 mL). Brine (250 mL) was added resulting in a phase split. The organic layer (1300 mL, 27 vol., $K_f$=3.45%) was split off and charged to a 3-L RB flask. The flask was heated (atmospheric) to distill off some of the 2-MeTHF. Once 15 volumes of 2-MeTHF (720 mL) remained (30 minutes), the solution was reanalyzed for water content ($K_f$=0.24%). The reaction was then cooled to 50-55° C. and polished filtered through filter paper (very little solids present). The solution was then recharged to the 3-L flask (after cleaning flask) and the solution was distilled down to 9 volumes (430 mL). The solution was then heated to 70° C. and heptane was added in portions over one hour. The heat was then turned off and the solution was allowed to slowly cool to room temperature (after one hour the temperature was 48° C.). After stirring for 70 hours, the mother liquor was checked by HPLC analysis for 3 (2.7 mg/mL) and then filtered. The solids were washed with a 25% 2-MeTHF/heptane solution (75 mL, slurry) followed by 2×240 mL displacement wash with the same solution. The cake was washed one more time with heptane (240 mL) and then dried in a vacuum oven for 20 hours at room temperature. 3 (81.1 g, 86% yield, 99.2% AUC) was isolated as a dark red solid. $^1$H NMR (CDCl$_3$) analysis showed no residual solvent present.

Preparation of 4

Compound 3 (80.0 g, 1.0 equiv.) and 10% Pd/C (4.0 g, 5 wt %, 50% water wet) were charged to a 1-L glass reactor. THF (400 mL, 5 vol.) was added and the reactor was purged with argon. The reaction mixture was then put under $H_2$ (30 psi) at ambient temperature and stirred. After 2 hours, the reaction mixture was heated to 30° C. and stirred. After an additional 4 hours, the pressure was increased to 40 psi and stirred overnight. After 16 hours, the reaction was deemed completed by HPLC analysis (3 undetected). The reaction mixture was then filtered through Celite® and the pad was rinsed with THF (3×160 mL). The organic solution was then concentrated down ($V_F$=90 mL) and MeOH (400 mL, 5 vol.) was added. The mixture was concentrated down to dryness giving a semi-solid/foam. Additional MeOH (400 mL, 5 vol.) was added (not all solids dissolve) and the mixture was concentrated to dryness yielding 4 [77.0 g, 98% yield (accounting for solvents), 98.9% (AUC)] as a grey solid. $^1$H NMR (CDCl$_3$) showed 4.3 wt % MeOH and 0.1 wt % THF.

Preparation of 6

Compound 4 (75.1 g, 1.0 equiv.) was charged to a 2-L RB flask equipped with a sparge tube and thermocouple. AcOH (675 mL, 9 vol.) was added followed by 5 (22.4 g, 1.05 equiv.) and MeOH (75 mL, 1 vol.). Air was then introduced to the reaction via the sparge tube. After stirring for 21 hours at ambient temperature, the reaction was analyzed by HPLC showing 1.7% of 4, 79.7% of 6, and 18.6% of 6' present. The reaction was stirred for an additional 24 hours at which time the reaction was deemed complete (0.3% of 4, 1.9% of 6'). The reaction mixture was then concentrated (55° C.) until distillation stopped (calculated residual AcOH=86.3 g). 2-MeTHF (960 mL, 12.8 vol.) was added followed by 20% KOH (392 g). An additional 210 mL of 20% KOH was needed to bring the pH>13. The mixture was stirred for 10 minutes and then allowed to settle. The aqueous layer (650 mL) was removed and the organics were washed with a 5% brine solution (375 mL, 5 vol.). The aqueous was removed (390 mL, pH=10) and a second 5% brine wash (375 mL, 5 vol.) was performed. The aqueous was removed (380 mL, pH=7). The third brine wash was omitted due to neutral pH being obtained after 2 washes. The 2-MeTHF was then solvent swapped into IPAc (7 vol., 0.5 wt % 2-MeTHF) resulting in a slurry formation. The mother liquor was sampled after stirring for 65 hours showing the concentration of 6 as 6.3 mg/mL. The solids were then filtered and washed with IPAc (90 mL, 1.2 vol.), IPAc/n-heptane (1/1, 180 mL, 2.4 vol.), and then n-heptane (90 mL, 1.2 vol.). After drying on the filter for 2 hours, the solids were transferred to a vacuum oven and dried overnight at 40° C. affording 6 [80.9 g, 86% yield (accounting for solvent content), 97.3% (AUC)] as a light yellow solid. $^1$H NMR (CDCl$_3$) showed 0.8 wt % IPAc, 0.7 wt % 2-MeTHF, and no heptane present. The major impurity was the N-oxide (M+16) that was present at 2.3%.

Purification of 6

Compound 6 (74.2 g) was dissolved (fines present) in DCM (560 mL) and eluted through a pre-packed (DCM) silica gel (330 g) plug. The column was then flushed with EtOAc (3.0 L). Two fractions were collected (2.5 L, 1.0 L) and analyzed by HPLC. In both fractions, no N-oxide impurity was observed. The fractions were combined and partially concentrated ($V_F$=620 mL, 8.3 vol.) resulting in a thick slurry. n-Heptane (620 mL, 8.3 vol.) was added and the mixture stirred for 15 minutes. A sample of the mother liquor showed the concentration of 6 to be 2.7 mg/mL. The solids were filtered and washed with heptane (150 mL, 2 vol.) and dried in a vacuum oven at 45° ° C. After 15 hours, 6 [65.9 g, 89% recovery, ~100% (AUC)] was obtained as an off-white solid. $^1$H NMR showed only a trace of EtOAc and no n-heptane present.

Preparation of 7

Compound 6 (65.4 g) was dissolved in DCM (650 mL, 10 vol.) and MSA (60.0 g, 5.0 equiv.) was added over 15 minutes ($T_{max}$=29° C.). After 2 hours, a thick slurry was present and the reaction was sampled (mother liquor) showing no 6 present by HPLC analysis. Water (460 mL, 7 vol.) was added and the mixture was stirred for 40 minutes. The aqueous layer was removed and water (200 mL, 3 vol.) was added to extract the DCM layer. The aqueous layers were combined and then washed with DCM (170 mL, 2.5 vol.). DCM (650 mL, 10 vol.) was added to the aqueous and the mixture was basified with 6 N NaOH (120 mL) to pH=13. During the addition, solids started to crash out of solution and stick to the sides of the flask. At that time, the rate of base addition was increased significantly, causing the solids to dissolve readily ($T_{max}$=25° C.). This was probably due to the fact that 7 precipitates out of solution before the mixture was basic enough for the solids to become soluble in the DCM. Due the lack of an exotherm at this point it seemed prudent to add the base quicker once solids were present. The layers were separated and the aqueous layer was reextracted with DCM (325 mL, 5 vol.). The organic layer was dried over $Na_2SO_4$ ($K_f$=0.17%) and then concentrated down to 360 mL (5.5 vol.) resulting in precipitation of solids. The mixture was concentrated further (150 mL, 2.3 vol.) and IPAc (900 mL, 13.8 vol.) was added. The solvent volume was reduced again ($V_F$=245 mL, 4 vol.) and IPAc (325 mL, 5 vol.) was added. Analysis for the solvent ratio indicated the DCM levels were below the targeted level (1.6 wt %). Additional IPAc (65 mL, 1 vol.) was added and the slurry was stirred overnight. Quantitation of the mother liquor showed the 7 concentration was below the targeted level (2.0 mg/mL). The solids were filtered, washed with IPAc (2×130 mL, 2×2 vol.), and dried in a vacuum oven (>28 in Hg) at 45° C. for 2 days. 7 (46.9 g, 87% yield, 99.8% AUC) was obtained as a light yellow solid. $^1$H NMR ($CDCl_3$) showed IPAc (0.5 wt %) and DCM (<0.1 wt %) present.

Example 2: Initial Optimization for the Formation of Compound 6

A list of the experiments performed is given in Table 4.

TABLE 4

Optimization for the Formation of Compound 6*

| Entry | Temp ° C.** | Time (h) | AcOH (equiv.) | Solvent (vol.) | 4 | 6' | 6 | 7 |
|---|---|---|---|---|---|---|---|---|
| 1 | 100 | 2 | 0 | 52 (DMSO) | 1.67 | 0 | 94.25 | |
| 2 | 100 | 16 | 0 | 38 (DMF) | 25.06 | 0.62 | 70.89 | |
| 3 | 100 | 16 | 0 | 51 (MeOEtOH) | 17.55 | 10.97 | 68.31 | |
| 4 | 100 | 1.5 | 5.5 | 38 (DMSO) | 1.03 | 0.27 | 87.40 | |
| 5 | 100 | 5 | 1.37 | 10 (DMSO) | 10.08 | 7.55 | 70.81 | |
| 6 | 100 | 2 | 2.74 | 10 (DMSO) | 4.04 | 2.94 | 83.64 | |
| 7 | 100 | 1 | 0 | 10 (DMSO) | 92.80 | 4.14 | 2.61 | |
| 8 | 100 | 1 | 2.75 | 19 (DMSO) | 22.57 | 26.27 | 49.71 | |
| 9 | 100 | 1.5 | 5.5 | 19 (DMSO) | 0.85 | 0.21 | 77.30 | 9.4 |
| 10 | 100 | 2 | 3.8 | 5 (DMSO) | 1.12 | 0.60 | 80.55 | 7.48 |
| 11 | 100 | 2 | 4.25 | 10 (DMSO) | 0.84 | 0.94 | 83.38 | 6.48 |

*All of the reactions were run in open vials in 30-70 mg scale.
**A representative vial temperature.

As can be surmised by the data in Table 4, DMSO was the best solvent (see entries 1-3) and the use of acetic acid accelerated the reaction (see entries 4-11). Addition of 3 to 4 equivalents of the acid showed the best reaction profile. This two step strategy also avoided the heterogeneous nature of the reaction observed in the one-pot approach. Facile oxidation in the presence of air was required to generate 6 once the cyclization to afford 6' was complete. Initially, two separate reactions were run using the conditions determined in Table 4 but unfortunately lower than expected yield were realized and column purification was required as well (Table 5).

TABLE 5

Synthesis of 6 Using the Two Step Strategy

| Temp ° C. | Time (h) | AcOH (equiv.) | DMSO (vol.) | yield, % | Purity (% AUC) |
|---|---|---|---|---|---|
| 100-110 | 4.5 | 3.5 | 5 | 66 | 99.21 |
| 100-125 | 20.5 | 4.0 | 10 | 49 | 93.20 |

Example 3: Solubility Analysis of 3 in 2-MeTHF and Heptane

A series of experiments were performed to test the solubility of 3 in a mixture of 2-MeTHF and heptane.

TABLE 6

Solubility of 3 in 2-MeTHF/heptane @ 25° C.

| | 2-MeTHF/heptane (v/v) | | | | | | | | |
|---|---|---|---|---|---|---|---|---|---|
| | 1/0 | 9/1 | 8/2 | 7/3 | 6/4 | 5/5 | 4/6 | 3/7 | 2/8 |
| Solubility (mg/mL) | 100 | 32 | 23 | 13 | 8.0 | 4.5 | 3.8 | 1.2 | 0.3 |

Example 4: Screening and Optimization Reactions Using 1 and 2s in a Cross-Coupling Reaction to Generate 3

A surrogate compound (2s) was used instead of 2 to screen conditions (employing $Pd_2(dba)_3$ and Xantphos) and to optimize the cross-coupling reaction. The initial experiments probing this reaction are summarized in Table 7. It can be seen that the combination of 5 mol % $Pd_2(dba)_3$ and Xantphos with $Cs_2CO_3$ in THF resulted in a 90% isolated yield. A 90% yield initially indicated this approach a viable option to access 3.

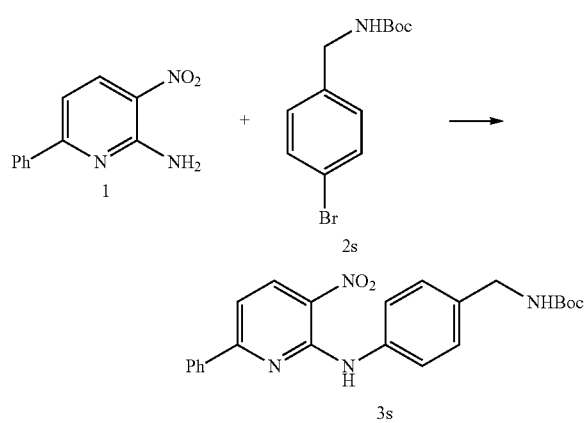

TABLE 7

Initial Results for the Feasibility of Cross-coupling 1 & 2s

| entry | Input 1 | Output | Purity | Conditions |
|---|---|---|---|---|
| 1 | 5 g | 7.60 g (77%) | N.D. | $Pd_2(dba)_3$ (5 mol %)/Xantphos (5 mol %)/dioxane/$Cs_2CO_3$ |
| 2 | 1 g | 1.20 g (62%) | 84% | $Pd_2(dba)_3$ (5 mol %)/Xantphos (5 mol %)/THF/$Cs_2CO_3$ |
| 3 | 10 g | 17.70 g (90%) | 91% | $Pd_2(dba)_3$ (5 mol %)/Xantphos (5 mol %)/THF/$Cs_2CO_3$ |

The catalytic loading of cross-coupling reaction was explored. As seen in Table 8, the amount of $Pd_2(dba)_3$ could be lowered to 1.25 mol % and Xantphos to 2.5 mol % with no observed decrease in isolated yield. A few of the reactions listed in Table 7 also examined the robustness of the reaction with respect to the tolerance of air. It was found that degassing the THF by bubbling argon through the reaction mixture prior to the addition of catalyst was not necessary and a blanket of argon was sufficient to prevent oxidation of the catalyst.

TABLE 8

Optimization of the Cross-coupling Reaction of 1 and 2s

| entry | Input (1) | Output | Time (h) | Purity (AUC) | Conditions |
|---|---|---|---|---|---|
| 1 | 5 g | 9.0 g (92%) | 17 | 98% | $Pd_2(dba)_3$ (2.5 mol %), Xantphos (5 mol %), with argon bubbling/THF/$Cs_2CO_3$. |
| 2 | 5 g | 9.0 g (92%) | 19 | 98% | $Pd_2(dba)_3$ (1.25 mol %), Xantphos (2.5 mol %), with argon bubbling/THF/$Cs_2CO_3$. |
| 3 | 5 g | 8.30 g (85%) | 16 | 97% | $Pd_2(dba)_3$ (1.25 mol %), Xantphos (2.5 mol %), without argon bubbling, with argon blanket/THF/$Cs_2CO_3$. |
| 4 | 5 g | 8.50 g (87%) | 16 | 97% | $Pd_2(dba)_3$ (2.5 mol %), Xantphos (1.25 mol %), without argon bubbling, with argon blanket/THF/$Cs_2CO_3$ |
| 5 | 5 g | N.R. | 19 | — | $Pd_2(dba)_3$ (1.25 mol %), Triphenyl phosphine (2.5 mol %), without Ar bubbling, with Ar blanket/THF/$Cs_2CO_3$. |

Example 5: Experiment on Cross-Coupling Reaction on 100 g of Compound 2 Using 2-MeTHF as Solvent An experiment on the cross-coupling reaction on 100 g of compound 2 using 2-MeTHF as the solvent was carried out. The reaction progress was slow following the addition of 1.25% of $Pd_2(dba)_3$ and 2.5% of Xantphos. Second charges of $Pd_2(dba)_3$ (1.25%) and Xantphos (2.5%) and $Cs_2CO_3$ (1.1 equiv.) were employed to push the reaction to completion (45 hours total). The phase splits were problematic during the work-up. Fine insoluble powders floating in the solution and the walls of the reactor being coated with a black residue led to the difficulties during the extractive work-up. The addition of brine or warming the reaction mixture did not improve the issue. Filtration of the batch (biphasic) to remove any particulates afforded a satisfactory phase split and the remainder of the extractive work-up proceeded without incident. The final product was isolated from 2-MeTHF with heptanes as an anti-solvent (yield: 72%, purity: 96.98%).

Example 6: Experiments on Hydrogenation Reaction to Produce Compound 4

Catalytic hydrogenation of 3 was initially carried out in EtOAc (15 vol.) with 10% Pd/C (10 wt %) under 40 psi of hydrogen gas. After 3 hours, the reaction was complete by HPLC analysis. Compound 4 was isolated in quantitative yield as a foam by concentrating the filtrate to dryness after the catalyst is removed by filtration through Celite®.

Although the reaction was high yielding, the amount of solvent required to perform the reaction limited the throughput due to the poor solubility of 3 in EtOAc. It was therefore desirable to find an alternate solvent for this reaction to prevent the risk of poor conversion while increasing the volume efficiency. To address this issue, the solubility of 3 was evaluated in HOAc and THF in addition to 2-MeTHF. These solvents were chosen since 6 and 7 free-base exhibited good solubility for these candidates and are used in other process steps. The solubility of 3 is 24.8 mg/mL in HOAc, 100 mg/mL in 2-MeTHF and 155 mg/mL in THF. These results suggest that it should be possible to perform the hydrogenation in less than 10 volumes of THF. In one embodiment, THF is used for the hydrogenation reaction. In another embodiment, 2-MeTHF is used for the hydrogenation reaction. When THF was used, complete dissolution of 3 was observed with 6 volumes of solvent and 2-MeTHF required 8 volumes. In one embodiment, when the hydrogenation reaction was run at 40 psi hydrogen pressure at 40° C., the reaction was typically complete in 2 to 3 hours. The final variable which was investigated was catalyst loading. The initial 10 wt % loading was reduced to 5 wt % without any decrease in reaction time, yield or purity.

An isolation procedure for 4 was developed as an alternative approach to concentration to dryness. When either THF or 2-MeTHF was used, partial concentration followed by solvent swapping into 2-PrOH (3-5 vol.) and adding heptane (10-15 vol.) as an anti-solvent gave a reasonable slurry which, when filtered, afforded 4 (95% yield) as a light grey solid with a high purity (>99% AUC).

Alternatively, since compound 4 was soluble in HOAc, the hydrogenation reaction can be performed in HOAc (10 vol.) and transferred directly into the cyclization/oxidation step to afford 6 directly. The hydrogenation reaction was complete in 4 hours when subjected to 40 psi hydrogen pressure at ambient temperature. Filtration of the catalyst afforded a clean solution of 4 that could be directly used for the conversion to compound 6.

The synthesis of compound 4 via catalytic hydrogenation of 3 without hydrogen gas was also explored. Compound 3, aldehyde 5 (1.05 equiv.), $NH_4COOH$ (5 equiv.) and 10% Pd/C (50 wt %) were combined in an alcohol (MeOH or EtOH) solvent and was heated to 65° C. Analysis by HPLC indicated conversion to compound 6 but reaction times were quite long in comparison to the standard hydrogenolysis conditions at 40 psi. The hydrogenation reaction without hydrogen gas was investigated in AcOH and AcOH/Dioxane with incomplete conversion to 6. The hydrogenation reaction without hydrogen gas was also explored in a stepwise manner, omitting aldehyde 5. Under these conditions, 3 was readily converted to 4 in MeOH in less than 4 hours at ambient temperature. The hydrogenation reaction was successful using 10% MeOH/AcOH solution. Employing AcOH as the solvent also gave 4, however the reaction stalled, which was the solvent previously demonstrated to be successful for the conversion of 4 to 6. In an attempt to optimize the reaction conditions, it was found that the reaction could be run using 10% MeOH/AcOH (10 vol.) with $NH_4COOH$ (5 equiv.) and a 30 wt % loading of catalyst to afford 4. The catalyst was then filtered off and the aldehyde 5 led directly to 6. Unfortunately, if the reaction was held for extended periods (>24 hours) additional impurities were generated. Since performing the conversion of 3 to 4 under 40 psi of hydrogen was not an issue, the efforts to optimize hydrogenolysis without the use of hydrogen gas were not pursued further.

Example 7: Screening and Optimization for the Conversion of 4 to 6

A set of screening reactions was performed to investigate the conversion of 4 to 6' which could then be oxidized to 6. The optimization began by evaluating the solvents EtOH, PrOH, toluene and DMSO with both 1.1 and 3.0 equivalents of aldehyde 5. These reactions were performed on 100 mg of 4. The results are summarized in Table 9.

TABLE 9

Solvent Screen for the Conversion of 4 to 6'

| | | | 6.5 hours | | | | 22.5 hours | | | |
|---|---|---|---|---|---|---|---|---|---|---|
| Entry | Solvent | 5 (equiv.) | %4 | %6 | %6' | %7 | %4 | %6 | %6' | %7 |
| 1A | EtOH | 1.0 | 12.5 | 10 | 72 | 2.5 | 4.0 | 21 | 63 | 10 |
| 1C | EtOH | 3.0 | 4.5 | 10 | 78 | 6.0 | 2.0 | 21 | 47 | 28 |
| 2A | PrOH | 1.0 | 8.0 | 10 | 75 | 3.0 | 7.0 | 23 | 59 | 6.0 |
| 2C | PrOH | 3.0 | 3.0 | 10 | 74 | 10 | 2.0 | 25 | 47 | 23 |
| 3A | Toluene | 1.0 | 4.5 | 17 | 76 | 0.5 | 2.0 | 31 | 63 | 3.0 |
| 3C | Toluene | 3.0 | 2.0 | 15 | 79 | 1.4 | 1.0 | 33 | 54 | 11 |
| 4A | DMSO | 1.0 | 12.0 | 26 | 41 | 20 | 12.0 | 39 | 30 | 18.5 |
| 4C | DMSO | 3.0 | 4.0 | 21 | 42 | 32 | 3.0 | 35 | 25 | 37 |

Compound 4 and 5 were also refluxed in toluene under nitrogen in the presence of fumaric acid with Dean-Stark trap to remove water. The reaction was very sluggish and the reaction purity profile was not promising (Table 10).

TABLE 10

Studies on the Synthesis of Compound 6'

| Time (h) | Temp ° C. | 4 (%) | 6' (%) | 6 (%) | (Vol.) |
|---|---|---|---|---|---|
| 19.5 | Reflux | 13.53 | 81.21 | 2.09 | 47 |
| 26 | Reflux | 9.72 | 75.63 | 1.59 | 47 |
| 44 | Reflux | 7.46 | 77.62 | 1.80 | 47 |

Based on the results in Table 9, it was difficult to prevent oxidation of 6' to 6. It was possible to convert 4 to 6 directly under mild conditions. The reaction was performed in an HOAc/MeOH (9/1, 47 vol.). As it can be seen from the data in Table 11, the purity profile was improved by using this solvent system compared to what was observed with other systems.

TABLE 11

Synthesis of 6 Directly From 4 in AcOH/MeOH

| Time (h) | Temp ° C. | 4 (%) | 6' | 6 | 7 | Note |
|---|---|---|---|---|---|---|
| 1 | 50 | 7.37% | 2.15% | 88.58% | 0.74% | 1.1 equiv. 5 |
| 2 | 50 | 4.23% | 0.42% | 92.53% | 0.88% | 1.1 equiv. 5 |
| 15.5 | 20 | 1.13% | 0.49% | 92.73% | 0.93% | 1.1 equiv. 5 |

Further optimization reactions were investigated with reduced reaction volume and only a slight excess (1.05-1.1 equiv.) of compound 5. At elevated temperature, the reactions were complete (or near complete) in 4 hours (Tables 12-14). However, a new impurity, Impurity 7, was generated and was more significant in the more concentrated reactions. At ambient temperature, the reaction was slow, but it gave a more favorable purity profile avoiding the formation of Impurity 7.

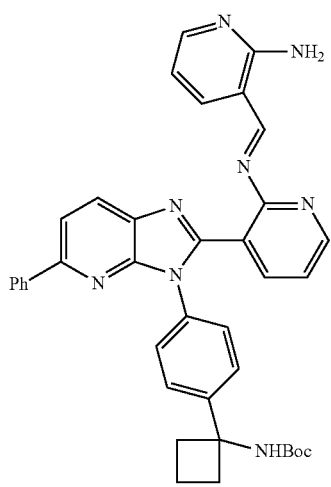

Impurity 7

From all the data collected, the solvent volume selected for further study was 10 volumes of AcOH/MeOH (9:1) at ambient temperature. Stirring compound 4 (1.0 equiv.) and compound 5 (1.05 equiv.) in AcOH/MeOH (10 vol.) overnight at ambient temperature open to an air atmosphere afforded near complete conversion to compound 6.

TABLE 12

Conversion of 4 to 6 in AcOH/MeOH (9:1, 20 volumes)

| Total Time (h) | Temp ° C. | 4 (%) | 6' (%) | 6 (%) | 7 (%) |
|---|---|---|---|---|---|
| 1 | 50 | 2.36 | 30.52 | 63.81 | 0.81 |
| 4 | 50 | 2.47 | 0.39 | 93.08 | 0.83 |
| 20 | ambient | 0.34 | 0.40 | 92.82 | 0.74 |

TABLE 13

Conversion of 4 to 6 in AcOH/MeOH (9:1, 10 volumes)

| Total Time (h) | Temp ° C. | 4 (%) | 6' (%) | 6 (%) | 7 (%) |
|---|---|---|---|---|---|
| 1 | 50 | 1.71 | 39.75 | 55.24 | 1.34 |
| 4 | 50 | 0.92 | 0.32 | 92.38 | 2.93 |
| 20 | ambient | 0.35 | 0.15 | 93.14 | 1.76 |

TABLE 14

Conversion of 4 to 6 in AcOH/MeOH (9:1, 5 volumes)

| Total Time (h) | Temp ° C. | 4 (%) | 6' (%) | 6 (%) | 7 (%) |
|---|---|---|---|---|---|
| 1 | 50 | 0.98 | 38.67 | 57.24 | 1.92 |
| 4 | 50 | 0.34 | 0.74 | 91.03 | 4.47 |
| 20 | ambient | 0.40 | 0.18 | 88.73 | 4.91 |

More specifically, when the reaction was stirred at ambient temperature until 4 was consumed, increasing the reaction temperature to 50° C. for an additional 2 hours promoted any remaining 6' convert to 6 (Table 15). Alternatively, stirring the reaction for a longer period of time (24 hours) at ambient temperature eventually led to complete conversion to 6. Therefore, these data suggest that once the reaction of 4 to 6' is complete, the overall purity of the reaction mixture is unaffected by heat if applied to drive the reaction to completing to 6.

TABLE 15

Effect of Reaction Temperature (50° C.) in Later Stages of the Reaction

| Total Time (h) | Temp ° C. | 4 (%) | 6' (%) | 6 (%) | 7 (%)* | Vol.* |
|---|---|---|---|---|---|---|
| 1 | ambient | 2.68 | 83.24 | 10.09 | 0.15 | 10 |
| 4 | ambient | 1.81 | 66.28 | 30.78 | 0.43 | 10 |
| 21 | ambient | 0.29 | 3.78 | 92.86 | 1.29 | 10 |
| 23 | 50 | 0.27 | 0.09 | 95.53 | 1.08 | 10 |

*HOAc/MeOH (9:1) was used as the solvent mixture

Further investigations to evaluate the effect increasing the charge of 5 (1.2 equiv. vs. 1.05) were explored. It was shown that increasing the equivalents of 5 had a detrimental effect on the reaction. There was no observed increase in the rate of reaction and a significant amount of impurity 7 formed.

Further investigations to evaluate the effect of altering the solvent ratio of HOAc/MeOH as well as the effect of the temperature (50° C. vs. 20° C.) on the reaction were completed. As seen in Table 16, the rate of consumption of 4 to either 6' or 6 is similar at 6 hours at both temperatures regardless of solvent ratio but the rate of oxidation from 6' to 6 is more dependent on temperature than amounts of acetic acid. The impurity profile was more favorable when the reaction was run at 20° C. with <1% unknown impurities by HPLC analysis (AUC).

TABLE 16

Optimization of MeOH/HOAc Conditions for the Conversion of 4 to 6

| | | Temp | 1 h | | | | 6 h | | | | 22 h | | | |
|---|---|---|---|---|---|---|---|---|---|---|---|---|---|---|
| Entry | MeOH:HOAc* | (° C.) | %4 | %6 | %6' | %7 | %4 | %6 | %6' | %7 | %4 | %6 | %6' | %7 |
| 31A | 1:5 | 50 | 3 | 25 | 72 | 0.4 | 2.6 | 69 | 22 | 2.2 | 2.7 | 76.5 | 11.9 | 3.7 |
| 31B | 1:2 | 50 | 5 | 22 | 69 | 0.6 | 2.8 | 70 | 21.5 | 1.8 | 1.3 | 91.2 | 0.2 | 2.6 |

TABLE 16-continued

Optimization of MeOH/HOAc Conditions for the Conversion of 4 to 6

| Entry | MeOH:HOAc* | Temp (° C.) | 1 h %4 | 1 h %6 | 1 h %6' | 1 h %7 | 6 h %4 | 6 h %6 | 6 h %6' | 6 h %7 | 22 h %4 | 22 h %6 | 22 h %6' | 22 h %7 |
|---|---|---|---|---|---|---|---|---|---|---|---|---|---|---|
| 31C | 1:1 | 50 | 4 | 19 | 74 | 0.8 | 3.2 | 62 | 26 | 2.8 | 3.7 | 71.0 | 14.7 | 3.9 |
| 31D | 1:1 | 20 | 11 | 4 | 84 | 0 | 3.3 | 32 | 63.5 | 0.4 | 1.7 | 71.4 | 25.6 | 0.6 |

*reactions were all run with 10 volumes of solvent with 1.1 equivalents of 5

The focus of the development of this step then shifted to the work-up. A test reaction was run with 1:9 MeOH/HOAc (10 vol.) at 50° C. with 1.05 equivalents of aldehyde 5 on 5.0 g scale (4). The end point of the reaction afforded a crude reaction mixture which was analyzed by HPLC to have 1.0% 4, 93% 6, 0.2% 6' and 0.9% 7. After concentration to remove the bulk of acetic acid, the residue was dissolved in EtOAc and a basic aqueous wash was employed to remove residual HOAc. The EtOAc solution was then concentrated to 5 volumes and crystallization had occurred. After stirring for the slurry for 4 hours at ambient temperature, the solids were isolated by filtration and dried under vacuum. This approach afforded 6 as an off-white solid in 67% yield (98.4% AUC).

While this initial trial was very promising, in subsequent experiments on larger scale, complications were encountered. One issue was that during the neutralization of acetic acid, emulsions were often obtained. Multiple solvent systems were investigated and the solubility of 6 was evaluated to estimate the efficiency of the extraction (Table 17).

TABLE 17

Solubility of 6

| | Solvent | | | | | | |
|---|---|---|---|---|---|---|---|
| | EtOAc | IPAc | DCM | Toluene | MTBE | THF | 2-MeTHF |
| Solubility (mg/mL) | 6.6 | 2.9 | 126 | 4.5 | 0.69 | 110 | 25 |

When IPAc and water were added to the reaction mixture a suitable phase split was observed. However, once the IPAc layer was separated and treated with base to neutralize the residual acetic acid, an emulsion would form. Due to the low solubility of 6 in EtOAc and IPAc, there was also an issue with 6 crystallizing out of the solution before the workup was complete.

A DCM/water system was also explored and, although there were no issues with premature crystallization of 6, emulsion problems persisted during the neutralization of HOAc. Attempts were made to neutralize the reaction to a pH of ~5-6 to avoid a basic aqueous layer. This procedure did avoid emulsions but was not completely sufficient at neutralizing AcOH. Adding additional water washes also led to emulsion problems. It was hypothesized that the base used to quench the AcOH might also make a difference due to the solubility of the salts formed in water. Aqueous NaOH was used in the initial experiments. The use of KOH did not have any substantial effect when DCM was used as the organic solvent.

The third solvent system investigated was 2-MeTHF/water. Initially, favorable phase splits were realized although more organic solvent (15 vol.) was needed than when DCM (10 vol.) were used. This system suffered from the same emulsion issues when basified. Different bases were also screened with this system including KOH and NH$_4$OH.

When NH$_4$OH was used, a significant amount of off-gassing occurred. When KOH was used, the emulsion formation was improved. As a result, KOH was selected as the base of choice in the work-up. The premature crystallization issue was also a risk in 2-MeTHF. However, it was determined that this was only a risk if the mixture was cooled during the work-up. If the mixture was warmed during the quench (~40-50° C.) all solids remain in solution. Once neutralization of HOAc was complete, a simple solvent swap from 2-MeTHF into IPAc afforded 6 in good yield and purity [>80%, ~99% (AUC)].

To reduce the amount of AcOH which required neutralization, distillation of a portion of the AcOH before the aqueous work-up was evaluated. A stability study showed that the reaction mixture was stable to concentration (15 vol. down to 4 vol.) as well as to extended hold times (>1 day). Based on this information, a series of experiments were carried out in which the AcOH was partially removed (to 4 vol.) before neutralization. A summary of the experiments can be found in Table 18 below. It was determined that distillation of AcOH significantly reduced the work up volume and was implemented in future experiments.

TABLE 18

Solvent and Base Optimization for the Isolation of 6

| Exp | Extraction Solvent (vol.) | AcOH Content (vol.) | Base used | 1$^{st}$ wash (pH) | 2$^{nd}$ wash (pH) | 3$^{rd}$ wash | Yields (AUC) |
|---|---|---|---|---|---|---|---|
| 1 | MeTHF (10) | 4 | NaOH | 6 | 14 | N/A | 85% (97.5%) |
| 2 | DCM(10) | 4 | NaOH | 6 | 14 | N/A | N/A |
| 3 | DCM(10) | 4 | NaOH | 10 | Water | N/A | 75% (97.5%) |
| 4 | DCM(10) | 4 | KOH | 12 | N/A | N/A | N/A |
| 5 | MeTHF (15) | 9 | KOH | 5 | 7 | 13.5 | 85% (98.8%) |
| 6 | MeTHF (15) | 9 | NH$_4$OH | 5 | 11 | 11 | 85% (99.0%) |
| 7 | DCM(10) | 9 | KOH | 5 | 5 | N/A | N/A |
| 8 | MeTHF (15) | 9 | KOH | 5 | 7 | 14 | 82% (98.9%) |
| 9 | MeTHF (15) | 4 | KOH | 8.6 | Water | Water | 84% (99.1%) |

Although an isolation procedure for 6 had been established, an impurity with a mass of M+16 was occasionally detected by LCMS analysis in the some batches of 6 synthesized and isolated using this procedure (<4% AUC). It is still not understood why and where this impurity was formed. Once this impurity is formed it is difficult to be purged by recrystallization. Carrying the impurity into the deprotection step and purging it during the isolation of 7 was also not successful. It was discovered that employing a silica gel filtration of 6 eluting with EtOAc successfully removed the impurity.

Example 8: Optimization for the Synthesis of 7

Initial attempts to synthesize 7 from 6 involved adding TFA (10 equiv.) to a DCM solution (10 vol.) of 6. The overall conversion was complete at ambient temperature after 15 hours. Increasing the temperature to 40° C. lowered the conversion time to 4 hours. Other solvents which were evaluated were DCE, anisole and IPA. In the later two cases, a mixture of compound 6 and 7 precipitated out of solution (presumably as the TFA salt). DCE afforded complete conversion after one hour at 80° C. Although the conversion to 7 was relatively facile, the workup was problematic resulting in sticky solids precipitating out solution using multiple conditions.

Once the reaction quench conditions were established, several experiments were conducted for the isolation of 7. Extraction with aqueous HCl resulted in solid precipitation in the aqueous layer. Other experiments were investigated with different acids to avoid precipitation including citric acid and methanesulfonic acid (MSA). It was found that MSA did not lead to precipitation of solids during the work up. This allowed the aqueous layer to be washed with DCM to remove impurities including residual 6.

Isolation of 7 from the MSA aqueous layer was completed by addition of DCM followed by basification with aqueous NaOH to extract the 7 free base into the DCM layer. This procedure did not precipitate solids during the extractive process, minimizing the previously encountered issues. Isolation from the DCM solution was developed by concentrating the volume of the DCM to induce crystallization followed by the addition of heptane as an anti-solvent. Subsequent experiments showed that by solvent swapping from DCM into 2-PrOH afforded a well filtered slurry. Possible solvents candidates which could be used to efficiently extract 7 were limited to DCM due to the poor solubility of 7 in a variety of common solvents (Table 19).

TABLE 19

Solubility of 7 in a Selection of Solvents

| Solvent | | | | | | | |
|---|---|---|---|---|---|---|---|
| | EtOAc | IPAc | DCM | Toluene | MTBE | THF | 2-MeTHF |
| Solubility (mg/mL) | 5.6 | 2.9 | 73 | 9.3 | 0.76 | 24 | 4.8 |

Based on the success of using MSA during the workup and isolation of 7, an attempt was made to perform the deprotection of 6 using MSA (5 equiv.) instead of TFA. The MSA-mediated reaction was more facile (one hour) than TFA at ambient temperature. The work-up was employed as described above through the DCM extractive process.

Example 9: Studies on the Synthesis of Compounds 1, 1', 2 and 2'

9a). Studies on the Synthesis of Compounds 1 and 1'

One of the approaches (Scheme 6) relies on a Suzuki reaction between commercially available 6-chloro-2-amino-3-nitropyridine and phenyl boronic acid to afford 1. Fortunately, 1 is not only a desired starting material for the synthesis of 3 but it is also an intermediate for the synthesis of 1'.

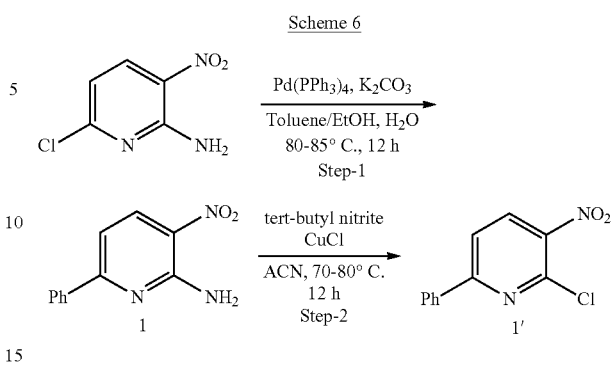

Scheme 6

The Suzuki reaction contains two major problems for scaling the reaction and maximizing the throughput. The procedure required large volumes of solvent (85 vol.) and also employed about 2 mole percent of Pd(PPh$_3$)$_4$ catalyst.

In order to reduce the amount of solvent and lower the catalytic loading of Pd(PPh$_3$)$_4$, a brief optimization series was performed. It was discovered that the amount of solvent could be lowered to 36 total volumes and the catalytic loading of Pd(PPh$_3$)$_4$ could be reduced to 1 mol % with no decrease in the yield or purity of 1. The results are summarized in Table 20 and a representative procedure of the optimized conditions can be found in the Examples section.

TABLE 20

Investigation of Reaction Volume and Catalytic Loading for the Synthesis of 1

| entry | Scale (g) | Output (yield) | Purity (AUC) | Conditions |
|---|---|---|---|---|
| 1 | 10 | 5.4 g (43.5%) | 98.4%. | Toluene (75 vol.), EtOH (10 vol.), Pd(PPh$_3$)$_4$ (2 mol %) Purified by column chromatography |
| 2 | 5 | 3.8 g (61.3%) | 98.1% | Toluene (75 vol.), EtOH (10 vol.), Pd(PPh$_3$)$_4$ (1 mol %) Purified by column chromatography |
| 3 | 500 | 420.1 g (67.8%) | 96.6% | Toluene (36 vol.), EtOH (6 vol.), Pd(PPh$_3$)$_4$ (1 mol %) Purified by trituration in heptanes |
| 4 | 950 | 810 g (68.7%) | 89.4% | Toluene (30 vol.), EtOH (6 vol.), Pd(PPh$_3$)$_4$ (1 mol %) Purified by trituration in heptanes |
| 5 | 1000 | 980.0 g (79.0%) | 89.4% | Toluene (30 vol.), EtOH (6 vol.), Pd(PPh$_3$)$_4$ (1 mol %) Purified by trituration in heptanes |

Compound 1' could be synthesized via the procedures of the Sandmeyer reaction (Step 2 of Scheme 6). Although 1' could be synthesized, the reaction was low yielding (30-40% isolated yield). The two main side products were identified as dehalogenation and hydrolysis of 1. A brief screen of alternate conditions was performed and the results are summarized in Table 21. As shown in Table 21, anhydrous acetonitrile (MeCN) did not impact the isolated yield as well as use of an alternate chloride source (TMSCl), fresh CuCl or dioxane in place of MeCN.

TABLE 21

Conditions used to try and improve the conversion of 1 to 1' (Sandmeyer chemistry)

| entry | Input (g) | Output (Yield) | Purity (% AUC) | Conditions | Remarks |
|---|---|---|---|---|---|
| 1 | 200 | 61.5 g (28.2%) | 97.9% | MeCN, t-butyl nitrite, CuCl, 40° C.-50° C. | Starting materials added at 50° C. |
| 2 | 3 | 11.5 g (35.9%) | 93.1% | MeCN, t-butyl nitrite, CuCl, 40° C.-50° C. | Extracted with EtOAc, instead of MTBE |
| 3 | 5 | — | IPC: 14.1% | Dioxane, t-butyl nitrite, CuCl, 60° C. | Starting materials added at ambient temperature then heated to 60° C. |
| 4 | 30 | 24.01 g (crude, 59.2%) | IPC: 47.7% Isolated: 54.8% | MeCN, t-butyl nitrite, CuCl, 55° C.-60° C. | Fresh Cu(I)Cl |
| 5 | 5 | N.R. | — | ACN, NaNO$_2$, TMSCl rt-60° C. (5 h) | Starting materials recovered |
| 6 | 5 | N.R. | — | CCl$_4$, NaNO$_2$, TMSCl 25-60° C. (6 h) | Starting material was recovered |
| 7 | 10 | 8.5 g (Crude) | IPC: 19.2%, Isolated: 43.1% | MeCN, CuCl, t-butylnitrite added at 50° C. | 45° C.-50° C. BF$_3$•Et$_2$O was used |
| 8 | 15 | 5.7 g (34.7%) | 93.7% | MeCN (KF-0.04%), t-butyl nitrite, CuCl, 55° C.-60° C. | Fresh Cu(I)Cl used |
| 9 | 10 | 3.5 g (32.2%) | 91.4% | MeCN (KF-0.04%), t-butyl nitrite, CuCl, 55° C.-60° C. | t-butyl nitrite added at 55° C.-60° C. |

IPC (in-process check analysis);
NR (no reaction)

The difficulty encountered improving the yields of the Sandmeyer reaction resulted in a search of alternate conditions to obtain 1'. It was observed that one of the major impurities in the Sandmeyer reaction was hydroxy derivative 1a. When 1a was treated with POCl$_3$, 1' was obtained in good yield (80%). Initially, a process was developed to convert 1 to 1a before performing the POCl$_3$ reaction to obtain 1' (Scheme 7). By performing the Sandmeyer reaction in aqueous THF, 1a was obtained in moderate yield and purity (Table 22). Initially, the POCl$_3$ reaction was performed neat (5 vol.) but it was found that the use of acetonitrile as the solvent also worked well and the charge of POCl$_3$ could be reduced to 1 volume (Table 23).

Scheme 7

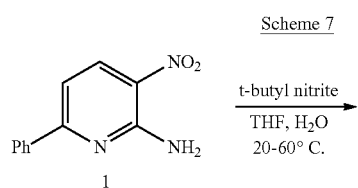

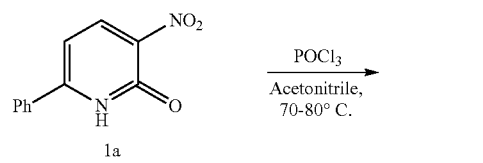

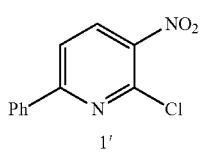

TABLE 22

Preparation of 1a Utilizing Sandmeyer Chemistry with 1 in Aqueous THF

| entry | Input (g) | Output (yield) | Purity (% AUC) | Conditions |
|---|---|---|---|---|
| 1 | 50 | 32.0 g (66.1%) | 92.3% | THF (10 vol.), water (2 vol.), t-butyl nitrite (2.0 equiv.), 55-60° C., 14 h |
| 2 | 200 | 148.1 g (73.8%) | 95.07% | THF (8 vol.), water (2 vol.), t-butyl nitrite (2.1 equiv.) added in portions (1 equiv. + 1 equiv. + 0.1 equiv.), 55-60° C. |

TABLE 23

Comparison of Neat POCl$_3$ vs. MeCN/POCl$_3$ for the Conversion of 1a to 1'

| entry | Input (g) | Output (Yield) | Purity by HPLC (% AUC) | Conditions |
|---|---|---|---|---|
| 1 | 8 | 8.5 g (97.2%) | 94.0% | Neat POCl$_3$ (5 vol.), 70-80° C., 8 hours |
| 2 | 30 | 27.1 (81.6%) | 97.7% | Acetonitrile (5 vol.), and POCl$_3$ (1 vol.), 70-80° C., 12 hours |

The ability to convert 1a to 1' using POCl$_3$ not only increased the isolated yield of 1' but the fact that 1b is available commercially possibly allowed for the preparation of 1a without the need for diazonium chemistry. Employing a Suzuki reaction with phenyl boronic acid and 1b provided 1a in one step (Scheme 8). The initial attempts made to familiarize the Suzuki reaction on 6-Chloro-3-nitropyridin-2(1H)-one with phenyl boronic acid and Pd(PPh$_3$)$_4$ to prepare 1a are given in Table 24. In general, the Suzuki reaction was successful, but an unidentified impurity was observed in all instances. This impurity was a challenge to purge but it was later discovered that the impurity could be purged during the isolation of 1' after the POCl$_3$ reaction.

Scheme 8

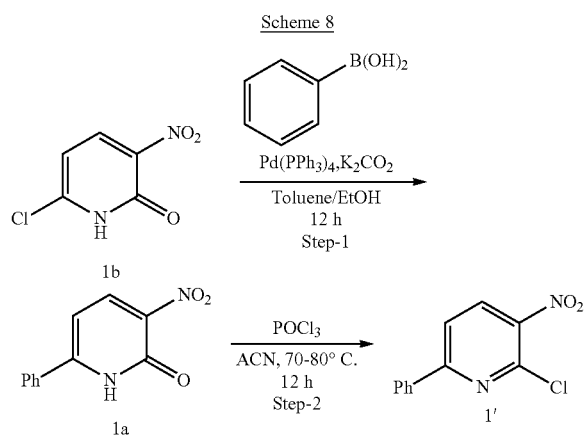

TABLE 24

Optimization and Execution of the Suzuki Reaction of 1b and Phenylboronic acid

| entry | Input (g) | Output (Yield) | Purity (% AUC) | Conditions |
|---|---|---|---|---|
| 1 | 400 | 316.2 g (63.8%) | 83.3% | a) (Pd-catalyst) 5 mol %<br>b) Phenyl boronic acid 1.1 equiv |

TABLE 24-continued

Optimization and Execution of the Suzuki Reaction of 1b and Phenylboronic acid

| entry | Input (g) | Output (Yield) | Purity (% AUC) | Conditions |
|---|---|---|---|---|
|   |      |                |        | c) 9.8% Impurity is present (at 1.17 RRT)<br>d) 60 vol. EtOAc used for washing<br>e) Reaction complete in 6 hours |
| 2 | 900 | 761.1 g (68.9%)<br>140.0 g 2$^{nd}$ crop (12.7%) | 78.0%<br>93% (2$^{nd}$ crop) | a) (Pd-catalyst) 3 mol %.<br>b) Phenyl boronic acid (1.02 equiv.)<br>c) After 6 hours, additional 5.0 g of Pd catalyst added.<br>d) Reaction complete in 7 hours<br>e) 35 vol. EtOAc used<br>f)) 16.3% impurity at 1.17 RRT |
| 3 | 1200 | 1.12 Kg (77.5%)<br>180.0 g 2$^{nd}$ crop (12.6%) | 71.0%<br>86.3% (2$^{nd}$ crop) | a) (Pd-catalyst) 3 mol %<br>b) Phenyl boronic acid (1.02 equiv.)<br>c) Reaction complete in 7 hours<br>d)) 19.1% impurity at 1.17 RRT |
| 4 | 1150 | 1.05 Kg (72.7%)<br>203.9 g 2$^{nd}$ crop (14.3%) | 81.8%<br>83.8% (2$^{nd}$ crop) | a) (Pd-catalyst) 3 mol %<br>b) Phenyl boronic acid (1.02 equiv.)<br>c) Reaction complete in 5 hours<br>d) 16.1% impurity at 1.17 RRT |

9b). Development of Compounds 2 and 2'

Schemes 9 and 10 illustrate the synthetic steps to generate compounds 2 and 2'.

Scheme 9

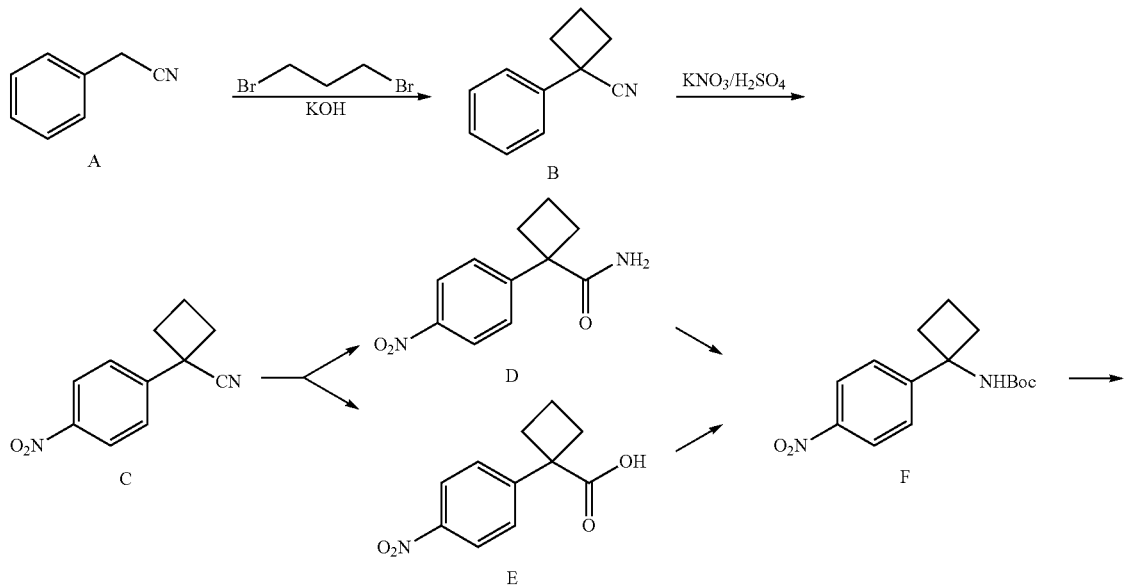

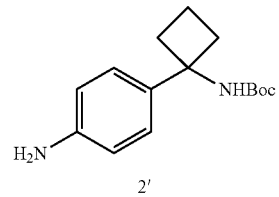

Scheme 10

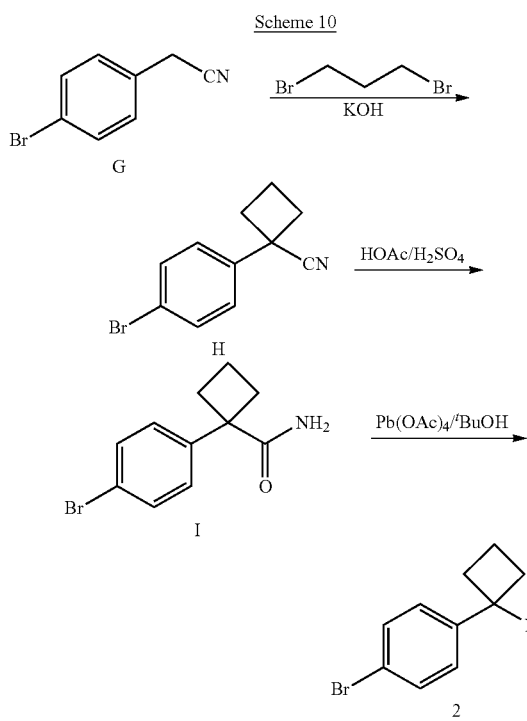

9bi). Synthesis of B

The synthesis of B was evaluated as follows. A mixture of powdered KOH (5.6 equiv.), water (0.77 vol.), toluene (7.7 vol.), and a catalytic amount of tetrabutylammonium bromide (0.05 equiv.) were heated to 45° C. 1,3-Dibromopropane (1.10 equiv) was then added in a single portion followed by the slow addition of a solution of phenylacetonitrile A (1.0 equiv.) in toluene (5.0 vol.). This solution was added over 45 minutes while maintaining the reaction temperature at 55-85° C. During the addition of compound A, a significant amount of white solids precipitated. The mixture was then heated to reflux (98-102° C.) for one hour and analyzed by HPLC. After one hour, compound A had been consumed and the reaction was deemed complete. At this stage, the reaction mixture was cooled to 70° C. and then diluted with n-heptane (10.4 vol.) to precipitate additional inorganic salts. After cooling the mixture to 20-30° C., the solids were removed by filtration and the filtrate was washed with water and brine. After drying over $MgSO_4$, the filtrate was concentrated to provide crude B as a yellow oil (typically >90% crude mass recovery). This crude oil was then purified by vacuum distillation (750 millitorr, bp=105-110° C.) to provide B (typically 50-60% yield). Distilled B typically contained a single impurity B2 in levels ranging from 2-4% (HPLC, AUC). Four batches of compound B were prepared on scales ranging from 50 g to 500 g without encountering any scale-up difficulties.

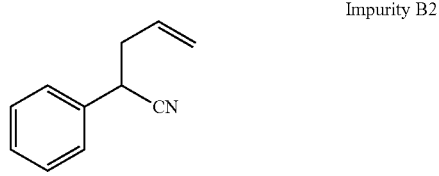

Impurity B2

As an alternative route to C, the above approach was investigated using 4-nitrophenylacetonitrile. In multiple experiments the reaction mixtures turned into black tar following the addition of 4-nitrophenylacetonitrile to KOH in toluene and water.

9bii). Synthesis of C and D

The conversion of B to C was achieved by slowly adding a solution of B to a mixture of $KNO_3$ in $H_2SO_4$ while maintaining the temperature below 15° C. On small-scale (25 g) the reaction was complete in less than one hour and quenched by pouring the solution onto ice. After extractive work-up, this approach provided C [99% yield, 95% (AUC)] as a free flowing tan solid. However, upon scale-up (500 g) it was difficult to stop the reaction at C. Instead, C further hydrolyzed fortuitously to D. After two hours, there was no detectable B remaining in the reaction mixture, however, 70% C and 30% D were observed HPLC (AUC). After stirring the reaction mixture overnight, the conversion of C to D was complete. The mixture was poured onto ice and extracted with DCM. After concentration of the DCM solution, the residue was dissolved in hot EtOAc (500 mL) and heptane (1.5 L) and cooled slowly to ambient temperature to induce crystallization. This provided pure D [55% yield over two steps from B, 99% (HPLC, AUC)] as a light yellow solid. It is likely with further optimization the yield from this crystallization can be improved since analysis of the mother liquor showed reasonably pure D still present (92% AUC). However, cursory attempts to isolate a second crop from this mother liquor were unsuccessful, leading to oiling out and no crystallization.

9biii). Synthesis of D from C

Since B could be easily converted to D in one pot, the conversion of C to D was only briefly examined. There are two possible routes for the conversion of H to I. One method used aqueous 30% $H_2O_2$ and $K_2CO_3$ in DMSO. In order to avoid the potential for peroxide concerns on larger scale, these conditions were not tested. Instead, the conditions using HOAc (or TFA) in $H_2SO_4$ were pursued. Since these conditions were found to perform well for H, it seemed reasonable to expect similar success when applied to the conversion of C to D. Upon heating C to 90° C. in the presence of HOAc (13.0 vol.) and $H_2SO_4$ (7.0 vol.) for 19 hours, the conversion to D was complete by HPLC. The mixture was then poured onto ice and after extractive workup D was purified by precipitation from DCM and heptane. This provided D [69% yield, 99% (AUC) by HPLC)] as a tan solid. The TFA conditions were also explored. Although the reaction can be carried out at room temperature instead of 90° C., the reaction did not proceed to completion in 19 hours. After workup the isolated yield was good (82%) but the overall purity was lower (92% AUC by HPLC).

9biv). Synthesis of E

The synthesis of E was investigated generate the carboxylic acid derivative of D. It was speculated that the Curtius rearrangement conditions using E and DPPA in t-butanol might be a suitable alternative to using $Pb(OAc)_4$ for the synthesis of F. It was found that D could easily be converted to E in the presence of EtOH and 6 M NaOH at 60° C. After aqueous workup, E was isolated quantitatively as a tan solid (99% AUC). This material can be used directly without further purification.

9bv). Synthesis of F Via Pb(OAc)

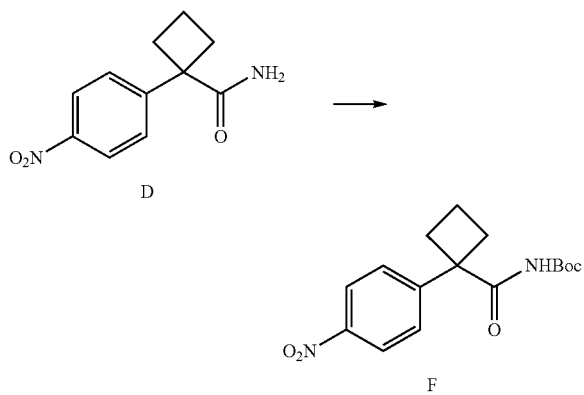

The synthesis of F was completed by adapting the procedure for the preparation of 2 from I. The process for preparing 2 involves portion-wise addition of Pb(OAc)$_4$ to a solution of I in t-butanol (5.0 vol.) at 75° C. However, D was not as soluble in t-butanol (5.0-6.0 vol.) at 75° C. as I is soluble in t-butanol. When the conversion of D to F was performed on small-scale (30 g), the addition of Pb(OAc)$_4$ was uneventful and the reaction was deemed complete after an hour at 75° C. (the lower solubility of D did not alter the outcome of the reaction). After work-up and isolation, F was obtained in 85% yield, however, the purity was poor (92.5%) with two significant impurities. One impurity was identified as the isopropylcarbamate derivative F2 (5%) which was hypothesized to be the result of trace isopropanol in t-butanol. The other impurity (2.5%) was not identified. This material was then converted directly to 2' and the resultant product was purified by silica gel chromatography to purge the two impurities present in F.

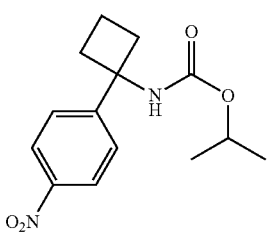

Isopropylcarbamate Impurity Compound F2

The conversion of D to F was then scaled to 200 g and no complications were encountered. The 200 g reaction provided compound F [178 g, 67%, 92.0% (AUC)] as a white solid after purification by re-slurry in MTBE (1.5 vol.) and heptane (3.0 vol.). The single largest impurity was the isopropylcarbamate derivative F2 [6.5% (AUC)]. The filtrate was then concentrated to dryness to provide additional F as a brown solid [48 g, 18%, 72% (AUC)].

In an attempt to minimize the formation of the impurity F2, HPLC grade t-butanol (99.8% purity) was used in place of reagent grade t-butanol. D (50 g) was converted to F [38 g, 57%, 96% (AUC)] and found to contain only 3.1% of impurity F2. Another reaction was then evaluated at lower temperature (45° C. vs. 75° C.) in an attempt to suppress impurity formation; however no conversion of D to F was observed at 45° C.

Attempts were made in parallel to develop a method for removing the isopropyl carbamate impurity F2. Recrystallization from MeOH or EtOH and water provided moderate purity upgrades (impurity decreased from 2% down to 1%). Subjecting the material to a second recrystallization was also attempted, but this strategy did not remove the residual F2 (~0.6% remained). A short term solution to remove this troublesome impurity was then identified by exploiting the reactivity differences of the Boc- and isopropyl-carbamate groups. When treated with HCl, the Boc group of F readily cleaves and forms a water soluble HCl salt. The isopropylcarbamate derivative F2 does not react with the HCl and thus could then be washed away during aqueous workup and compound F-Free Base could be recovered by extractive workup at pH=11. On 5 g scale, compound F-Free Base was isolated in quantitative yield, free of the compound F2 impurity.

The re-protection of F-Free Base was then examined using standard conditions (DCM, Boc$_2$O, and Et$_3$N) and found to be quite problematic. During the course of the reaction, the undesired symmetrical urea derivative formed in appreciable amounts (20%, Figure 3) along with the desired F (80%). Another reaction was then conducted by adding compound F-Free Base slowly to excess Boc$_2$O and Et$_3$N in DCM; however this unexpectedly gave even more of the symmetrical urea byproduct (45%). Ultimately conditions were identified that completely suppressed the formation of the symmetrical urea. Under biphasic conditions, aqueous 1 M NaOH, THF, and Boc$_2$O (1.5 equiv.) gave the desired product F in good yield and high purity [81%, >99% (AUC)].

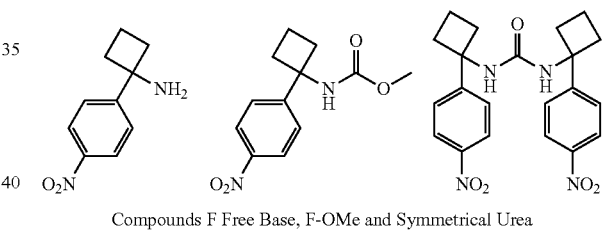

Compounds F Free Base, F-OMe and Symmetrical Urea

9bvi). Synthesis of F Via NaOH/Bromine

The synthesis of F was also explored using Hofmann rearrangement conditions. D was dissolved in MeOH, treated with 25 wt % NaOMe in MeOH (4.3 equiv.), and then cooled to 5° C. Drop wise addition of Br$_2$ (1.0 equiv) to the reaction mixture induced a mild exotherm. The reaction mixture was then warmed to ambient temperature and stirred for one hour. After that time the reaction was complete by HPLC analysis and then quenched by slow addition of saturated aqueous NH$_4$Cl solution (40 vol.). During the quench, the product (F-OMe) crystallized from the reaction mixture as large flaky white solids. These solids were isolated and dried to provide the methylcarbamate derivative compound F-OMe [81%, >99% (AUC)] as a white solid.

A second set of conditions were also explored where iodosobenzene was generated in-situ by the action of Oxone® on iodobenzene in either water and acetonitrile (generates compound F-Free Base) or in MeOH (generates compound F-OMe). While somewhat effective, these two reactions required lengthy reaction times (>41 hours) to achieve moderate conversions. In water and acetonitrile there was 31% conversion (HPLC) to compound F-Free Base after 41 hours. In MeOH there was 73% conversion (HPLC) to compound F-OMe after 46 hours. These two reactions were deemed too slow to be useful at this point and no further work was conducted with this reagent system.

Although there was an excellent route for preparing compound F-OMe, the method for the conversion of F-OMe back to compound F was not previously established. Multiple conditions were explored (Table 25), however only one set of conditions (HBr in HOAc) was effective. The main drawback to using HBr in HOAc was the formation of multiple byproducts during the deprotection. After these experiments, the methylcarbamate route was abandoned for more promising leads.

TABLE 25

Deprotection of F-Methyl Carbamate (F-OMe)

| Run | Solvent | Additive | Temp | Time | F-OMe (AUC) | F (AUC) |
|---|---|---|---|---|---|---|
| A | HOAc | 33% HBr | Ambient | 28 h | 6.7% | 53.7% |
| B | MeOH | 1M NaOH | Ambient | 22 h | 94.0% | 0% |
| C | Glycol | 6M NaOH | 55° C. | 19 h | 91.3% | 3.6% |
| D | MeOH | 6M NaOH | 55° C. | 19 h | 77.8% | 4.8% |
| E | MeOH | 6M HCl | Ambient | 19 h | 97.6% | 0.3% |
| F | MeOH | 6M HCl | 55° C. | 19 h | 96.8% | 0.3% |

9bvii). Synthesis of F Via DPPA

The synthesis of F from E and diphenylphosphorylazide (DPPA) in t-butanol was evaluated. The use of DPPA would potentially avoid two major drawbacks associated with using Pb(OAc)$_4$. The first is that Pb(OAc)$_4$ is difficult to handle and charge portion wise to the reaction. This sticky solid gradually deliquesces and turns black when exposed to air and/or humidity. The second reason for avoiding Pb(OAc)$_4$ is the large amount of PbCO$_3$ waste that is generated that then needs disposal. Using DPPA would eliminate both of these concerns since it is a liquid that is easily handled and produces diphenylphosphate as a byproduct. Initial attempts to convert E to F were conducted by adding DPPA (1.1 equiv.) slowly to a solution of E (1.0 equiv.) and Et$_3$N (1.1 equiv.) in t-butanol (20.0 vol.) at 75° C. After 16 hours at 75° C., the reaction was complete by HPLC analysis. However, during an attempt to purify F by column chromatography (5-20% EtOAc in heptane on silica gel), only a minor amount of F was isolated [26% yield, 99% (AUC)]. The low yield was attributed to the possible crystallization of F during column chromatography. This explanation is plausible since it was later determined that F has low solubility in EtOAc and n-heptane.

Therefore, the reaction was repeated and upon completion the mixture was quenched with aqueous 1 M NaOH and stirred at ambient temperature for 3 hours. Following work up, the product was isolated by crystallization from EtOH (8.0 vol.) and water (6.0 vol.). This method provided F [55%, 88.3% (AUC)] as a tan solid containing only a single impurity [isopropylcarbamate derivative F2, 11.7% (AUC)]. Interestingly, the DPPA byproducts were completely removed by the crystallization. A final experiment was then conducted to quantify the amount of F present in the crude reaction mixture. After aqueous workup, quantitative NMR (CDCl$_3$ using dimethyl fumarate) showed a potency of 78% F present in the crude mixture. The isopropylcarbamate impurity F2 was also present [6.8% (AUC)]. Although this reaction performed well, the formation of the troublesome isopropylcarbamate byproduct F2 could not be avoided.

Several additional experiments were then conducted using different nucleophiles to trap the intermediate isocyanate generated by DPPA. The primary goal of these experiments was to prevent formation of the isopropylcarbamate impurity F2 by avoiding the use of commercial t-butanol. Each reaction (Table 26) was performed by subjecting E (5 g, 1.0 equiv.) to DPPA (1.1 equiv.) in toluene or THF (20 vol.) in the presence of Et$_3$N (1.1 equiv.).

TABLE 26

Isocyanate Quench Experiments for the Preparation of F via DPPA

| Entry | Solvent | Nucleophile | Quench | Potency (NMR) |
|---|---|---|---|---|
| 1 | Toluene | 20 wt % KO$^t$Bu in THF | 0.1M NaOH | 33% |
| 2 | THF | 20 wt % KO$^t$Bu in THF | 0.1M NaOH | 35% |
| 3 | Toluene | 1.0M NaOTMS in THF | Citric acid | 39% |
| 4 | Toluene | 6M HCl | 6M HCl * | 70% |

* Reaction was heated to 75° C. for 14 hours following the HCl quench

Based upon the success of the aqueous 6 M HCl quench experiment (Table 26), this reaction was repeated on larger-scale. E (11.9 g) was converted to the isocyanate using DPPA in toluene with Et$_3$N and quenched with aqueous 6 M HCl. This time however, the conversion of the isocyanate intermediate to F-HCl salt was monitored periodically by HPLC analysis instead of stirring overnight at elevated temperatures. After heating in the presence of aqueous 6 M HCl at 75° C. for 2.5 hours, HPLC analysis showed no isocyanate intermediate remained and the reaction was deemed complete. A problem then arose during the aqueous workup and a severe emulsion formed. In retrospect the emulsion may have been due to not stirring the 6 M HCl quenched reaction mixture overnight at 75° C. (as was done in the small-scale experiment). It is possible that by only stirring for 2.5 hours, the DPPA byproduct (diphenylphosphate) did not hydrolyze fully to the extent of the reaction which was heated overnight at 75° C. The decision to monitor the consumption of the isocyanate intermediate by HPLC analysis may have led to the inadvertent partial hydrolysis of the DPPA byproduct. In the future the reaction should be monitored for the consumption of the DPPA by-products as well. The emulsion issue then led to lower than normal purity of F-Free Base being carried forward to F. This then resulted in a low yield and purity for the isolated F from this route [80%, 79% (AUC)]. This process is worthy of reinvestigation to address these hypotheses.

9bviii) Synthesis of 2'

The conversion of F to 2' was initially performed by subjecting F (5 g) in MeOH (10 vol.) to 5% palladium on carbon (50 wt % water wet catalyst) under 45 psi of hydrogen. After stirring for 17 hours, the reaction was complete by HPLC analysis and the mixture was filtered through a pad of Celite®. The filtrate was then concentrated to provide 2' in about quantitative yield (4.6 g) as a yellow oil. The reaction was then scaled to 29 g of F. Attempts were made to run the reaction in EtOH instead of MeOH due flammability concerns on larger scale; however the solubility of F in EtOH was poor. As a compromise, a mixed solvent system of 20% MeOH in EtOH (10 vol.) was investigated. After stirring for 16 hours, the reaction was complete. The filtrate was concentrated to a yellow oil (34 g) and then combined with the 5 g experiment for chromatographic purification (40/60 EtOAc/heptane, silica gel). 2' [30.4 g, 99% yield, 97.7% (AUC)] was obtained as a yellow oil. A final 170 g scale reaction was conducted using MeOH (10 vol.) and the reaction performed similar to the previous two experiments. After filtration through Celite®, the filtrate was concentrated to a yellow oil that solidified upon standing overnight at ambient temperature. This provided 2' [154 g, 100%, 98.3% (AUC)] containing only a single impurity [isopropylcarbamate derivative of 2' (1.7%)].

9bix). Synthesis of H

The procedure involved slow addition of a solution of G (1 equiv.) in toluene (3 vol.) to a biphasic mixture of KOH (5.6 equiv.), water (0.77 vol.), toluene (7.2 vol.), 1,3-dibromopropane (1.1 equiv.), and tetrabutylammonium bromide (0.1 equiv.) at 50-85° C. During the addition, the reaction mixture became quite thick and a significant amount of white solids were present (presumably KBr). After the reaction was complete, the mixture was cooled to room temperature and diluted with heptane (10.4 vol.) to precipitate additional solids. The batch was then filtered and the filtrate was washed with water (3 vol., twice), dried over MgSO$_4$, filtered, and concentrated. This provided crude H [>90% yield, 82-91% (AUC) typical purity] as a purple oil. This material was then routinely used without further purification in the next step. The major impurities present are likely oligomeric byproducts and the corresponding olefin from the un-cyclized intermediate that underwent elimination of HBr (H2).

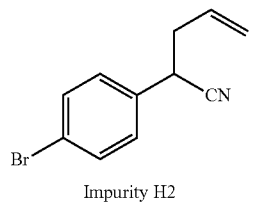

Impurity H2

The first modification introduced was to replace the powdered KOH with 50% aqueous NaOH. This avoided the exothermic dissolution of KOH and is operationally simpler on larger scale. Unfortunately, 50% NaOH was not effective and only a 16% conversion to H was achieved along with the formation of numerous new impurities. The second modification investigated was to increase the dilution of the reaction in an attempt to thin the thick slurry. When the volumes of toluene and water were doubled, only a marginal difference in the thickness of the slurry was observed. An unintended result of doubling the amount of water also caused the reflux temperature to be suppressed to 95° C. (normally 100-105° C.) and no conversion of G to H occurred. In order to reach 100° C., the water was distilled out at atmospheric pressure (Dean-Stark trap) until the reflux temperature reached 100° C. At 100° C., the reaction went to completion in one hour and provided H in average yield and purity. Based on this result, the procedural conditions were used for scale-up. The results of the three larger scale batches are summarized in Table 27

TABLE 27

Larger-Scale Conversion of G to H

| Entry | Input | Crude H (Crude Yield) | Purity (AUC) |
|---|---|---|---|
| 1 | 200 g | 201 g (83%) | 91% |
| 2 | 225 g | 264 g (97%) | 87% |
| 3 | 500 g | 519 g (86%) | 86% |

9bx). Synthesis of I

The conditions used to prepare I were identical to those used to prepare D. Although the HOAc and H$_2$SO$_4$ conditions worked well, these conditions contain safety concerns on heating the mixture to 90° C. larger scale. In an attempt to avoid heating to 90° C., complimentary conditions using TFA and H$_2$SO$_4$ at ambient temperature were evaluated. Treatment of H (10 g scale) with TFA (4 vol.) and H$_2$SO$_4$ (1 vol.) at ambient temperature resulted in a 95% conversion (by HPLC) to I after 26 hours. The reaction mixture was then poured into ice water and extracted with DCM. The organic layer was washed with saturated NaHCO$_3$, dried, and concentrated to give crude I containing a significant amount of residual TFA. Since the aqueous workup did not remove TFA effectively; these conditions were not pursued further.

Four intermediate-scale batches were completed using the HOAc and H$_2$SO$_4$ conditions. Following the general procedure, H was heated to 90° C. in the presence of HOAc (4 vol.) and H$_2$SO$_4$ (2 vol.) until H was consumed (<1% AUC by HPLC). The reaction was then cooled to ambient temperature and slowly quenched by pouring onto ice and water. After extractive workup with DCM, crude I was by purified silica gel chromatography. The results are summarized in Table 28.

TABLE 28

Large Scale Production of I

| Entry | Input (H) | Yield | Purity (AUC) | Method |
|---|---|---|---|---|
| 1 | 200 g | 74% | >99.9% | 80/20 EtOAc/heptane SiO$_2$ column |
| 2 | 142 g | 62% | >99.9% | EtOAc recrystallization |
| 3 | 200 g | 51% | 99.4% | MTBE SiO$_2$ plug column |
| 4 | 604 g | 80% | >99.9% | 80/20 EtOAc/heptane SiO$_2$ column |

In one instance (2$^{nd}$ entry Table 28), crude I solidified upon standing at ambient temperature. This material was then recrystallized from EtOAc. This recrystallization strategy was also attempted with crude I isolated as an oil, but was unsuccessful. I also partially crystallized while being loaded onto a silica gel column with EtOAc/heptane. To avoid this issue, it was advantageous to pre-absorb crude I onto silica gel using DCM and then concentrate the silica gel slurry to dryness prior to loading onto a column. As an alternative to EtOAc and heptane chromatography, a MTBE plug column was also evaluated (3$^{rd}$ entry Table 28). Unfortunately, the MTBE plug column was only evaluated once and gave a low recovery (51%). It is likely that I crystallized on the silica gel and then was not easily re-dissolved.

9bxi). Synthesis of 2

The synthesis of 2 was accomplished by using Pb(OAc)$_4$. Typically, reactions were complete after 90 minutes at 80-85° C. When the conversion of I to 2 was complete, the reaction slurries were cooled to ambient temperature and treated with solid Na$_2$CO$_3$ (1 weight equivalent) followed by MTBE (7.5 vol.). After stirring for 30 minutes, the solids (PbCO$_3$) were removed by filtration and the filtrate was washed with aqueous NaHCO$_3$. After aqueous workup, drying, and concentration, crude 2 was purified by re-slurrying in 10/90 MTBE/heptane (5 vol.) at ambient temperature. This method typically provided 2 [64-86% yield, 94-97% (AUC)] as an off-white solid. The only significant impurity present at this stage was the isopropylcarbamate derivative of 2 (2A).

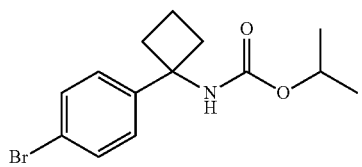

Impurity 2A

This undesired byproduct was analogous to the 2' chemistry and was presumed to be the result of the isocyanate intermediate reacting with trace isopropanol present in commercial t-butanol. Impurity 2A was typically present in 3-4% (AUC) in 2 after the 10/90 MTBE/heptane re-slurry. Table 29 summarizes the results of the larger-scale preparations of compound 2.

TABLE 29

Large Scale Production of 2

| Experiment | Input (I) | % Yield | Purity (AUC) | Impurity 2A (AUC) | Impurity RRT = 0.75 |
|---|---|---|---|---|---|
| 1 | 165 g | 64% | 95% | 4% | — |
| 2 | 118 g | 86% | 97% | 3% | — |
| 3 | 250 g | 84% | 94% | 3% | — |
| 4 | 217 g | 69% | 80% | 5% | 20% |

During the final experiment (Table 29, experiment 4) a new major impurity appeared (RRT=0.75). The source of this new impurity was unclear since the same lots of t-butanol and Pb(OAc)$_4$ were used in each experiment. Examination of previous reactions confirmed that this impurity had been typically present, but not at levels above 3-5%. Fortunately, this new impurity (RRT=0.75) could be removed by column chromatography (1/99 MeOH/DCM on silica gel) to provide 2 containing 2A (2.8% AUC) as the only impurity.

As an alternative to the Pb(OAc)$_4$ conditions, both Hofmann rearrangement and in-situ iodosobenzene conditions were explored. Using standard Hofmann rearrangement conditions, I (1 equiv.) was slurried in aqueous NaOH and treated drop wise with bromine (1 equiv.). Following the bromine addition, the reaction mixture was heated to 60° C. and the initial thin slurry converted to a ball of oily solids that was difficult to stir. After 2 hours, the reaction was assayed by HPLC (after quenching the sample with HCl) and showed a complex mixture of multiple peaks. There was also a significant amount (25%) of unreacted I present and the reaction was abandoned. A second set of conditions using iodosobenzene, generated in-situ by the action of Oxone® on iodobenzene, was also evaluated. The kinetics of this reaction were found to be quite slow and produced multiple species by HPLC. As a result, these conditions were not pursued further.

9bxii). Purification of 2

Several strategies were then investigated for the purification of 2 in order to remove the isopropylcarbamate impurity (2A). The first group of experiments were to re-slurry the crude 2 [95% purity containing 4% of 2A (AUC)] in mixtures of acetonitrile and water at ambient temperature (Table 30). Based on the results in Table 13, a mixture of 25-50% water in acetonitrile gives the best balance between recovery and purity.

TABLE 30

Compound 2 Re-slurry Results

| Solvent | % Recovery | HPLC Purity | Impurity 2A |
|---|---|---|---|
| 5% Water in Acetonitrile | Solids dissolved | — | — |
| 10% Water in Acetonitrile | 35% | 99.2% | 0.8% |
| 15% Water in Acetonitrile | 50% | 98.8% | 1.2% |
| 25% Water in Acetonitrile | 75% | 98.6% | 1.4% |
| 50% Water in Acetonitrile | 99% | 97.7% | 2.3% |

The next experiment was to evaluate recrystallization of 2 from acetonitrile and water (Table 30). In this study, 2 (97.3% purity, 2.7% impurity 2A) was used. There was no significant purity upgrade from these recrystallizations compared to the re-slurry results in Table 31.

TABLE 31

Compound 2 Recrystallization Results

| Solvent | % Recovery | HPLC Purity | Impurity 2A |
|---|---|---|---|
| 100% Acetonitrile | 52% | 98.8% | 1.2% |
| 33% Water in Acetonitrile | 71% | 98.1% | 1.9% |
| 40% Water in Acetonitrile | 86% | 97.9% | 2.1% |

A second re-slurry solvent system was then evaluated using 2-PrOH and heptane. Although a moderate purity upgrade (Table 31) was observed, the recoveries were lower than the corresponding water and acetonitrile experiments in Tables 30 and 31.

TABLE 32

Additional Re-slurry Attempts on Compound 2

| Solvent | % Recovery | HPLC Purity | Impurity 2A |
|---|---|---|---|
| 10% 2-PrOH in heptane | 50% | 98.1% | 1.9% |
| 25% 2-PrOH in heptane | 63% | 98.4% | 1.6% |
| 50% 2-PrOH in heptane | 38% | 98.9% | 1.1% |

Since many of the impurities (except impurity 2A) are more polar than compound 2, a silica gel plug column could be used as a preliminary purification method. To perform this plug column, crude 2 was dissolved in 1/99 MeOH/DCM and then loaded onto a silica gel column packed with the same solvent system. Compound 2 then eluted quickly ($R_F$=0.9-1.0), leaving the more polar impurities behind. The rich fractions were then concentrated to dryness and blended by a re-slurry in MTBE (2 vol.) and heptane (6 vol.) at ambient temperature to obtain a uniform lot. A 500 g lot of 2 can be prepared using this method. This provided 2 [97.2% (AUC)] containing compound 2A (2.8% AUC) as the only impurity present.

9c). Transfer of 2' Process to Manufacturing

Based on the development of a process to manufacture 2' preparation of a total of 2 kg of 2' was pursued. There was some concern regarding the scalability of preparing B on scale due to the work-up and distillation to obtain pure B. A switch from toluene to DMSO was made and although the reaction was more homogeneous, the formation of B2 was still observed and column chromatography was needed. This procedure was used to prepare 900 g of B which was taken forward to provide material for familiarization and prepare the initial ~500 g of API to supply GLP toxicity studies. The familiarization of the remaining steps went well and surprisingly there was no issue with the isopropyl carbamate impurity (F2) that plagued the development and was observed in the 500 g synthesis of 2. It is possible that the large scale manufacturer obtained their t-butanol from a different source that did not contain any 2-PrOH that could react to form F2. The 900 g of B synthesized delivered 477 g of 2' with 99.5% purity by HPLC.

A commercial source of B was identified and the purchased B was then used to prepare 1.61 kg of 2'. The experimental procedures for the large scale synthesis of 2' can be found in the Examples section.

Example 10: Experiments on Purification of 6 and 7 with High Pd Level

A small amount of 7 free base was prepared from an aliquot of the lot of 6 generated from 3 prepared via the cross-coupling reaction. The palladium level was reduced from 206 ppm from 281 ppm after the free base was isolated.

Five inexpensive, commercially available scavengers and activated charcoal were evaluated. To expedite the screening process, at least 4 times the calculated amount of the selected scavengers was employed to increase the likelihood of success in a short period of time. For comparison, two escalated loading (20 times and 40 times) experiments were tested as well.

TABLE 33

Treatment Result of 6 with Scavengers

| Entry | Scavenger | Scavenger wt (mg) | 6 Recovered (mg) | Pd (ppm) |
|---|---|---|---|---|
| | — | — | — | 281 |
| 1 | QuadraSil TA | 36 | 490.3 | 195 |
| 2 | QuadraSil MTU | 41 | 488.8 | 131 |
| 3 | QuadraSil AP | 29 | 493.5 | 204 |
| 4 | QuadraSil MP | 32 | 500.9 | 207 |
| 5 | Smopex 111 | 30 | 503.1 | 224 |
| 6 | Char coal | 101 | 458.9 | 123 |
| 7 | QuadraSil TA | 146 | 441.5 | 53 |
| 8 | QuadraSil TA | 286 | 369.5 | 32 |
| 9 | QuadraSil MTU | 143 | 451.8 | 19 |
| 10 | QuadraSil MTU | 288 | 411.9 | 26 |

In a typical experiment, a scavenger (>28 mg, >4 times of needs by calculation) was added to a solution of 6 (or 7, 500 mg) in DCM (5 mL). The mixture was stirred at 35° C. for 2.5 hours, cooled to ambient temperature, filtered through a 0.45 uM disk to a pre-weighed vial. The filtrate was then concentrated, recovery was recorded and palladium level was analyzed (Table 33 and 34).

TABLE 34

Treatment Result of 7 (Free Base) with Scavengers

| Entry | Scavenger | Scavenger wt (mg) | Compound 7 Recovered (mg) | Pd (ppm) |
|---|---|---|---|---|
| | — | — | — | 206 |
| 1 | QuadraSil TA | 36 | 513 | 76 |
| 2 | QuadraSil MTU | 41 | 510.6 | 39 |
| 3 | QuadraSil AP | 29 | 505.4 | 97 |
| 4 | QuadraSil MP | 36 | 502.1 | 19 |
| 5 | Smopex 111 | 30 | 507.7 | 95 |
| 6 | Char coal | 102 | 487.5 | 49 |
| 7 | QuadraSil TA | 142 | 474.8 | 17 |
| 8 | QuadraSil TA | 286 | 463.1 | 8 |
| 9 | QuadraSil MTU | 140 | 491.8 | 11 |
| 10 | QuadraSil MTU | 282 | 457.8 | 4 |

These data suggest that the scavengers are more efficient in the case of 7 free base over 6. As expected, the greater the quantity of scavenger used, the lower the recovery of the substrate. The best scavenger was QuadraSil MP which is also the most inexpensive scavenger for the treatment of 7 free base.

Example 11: Screening Alternate Oxidants for the Preparation of 6

In the original process, air was employed as oxidant for the preparation of 6. While air as oxidant was needed for the aromatization of intermediate 6' to 6, slow over oxidation of the final product 6 to (M+16) N-oxide was also observed because of sluggish aromatization step. In the process of achieving reaction completion, (M+16) N-oxide was noted to form and increase in the reaction. This specific impurity could not be purged either at this step or further downstream and posed a major issue in this process by process friendly crystallization/recrystallization procedures. To gain more control on the oxidation stage of this step, alternatives to air oxidation were considered. The goal was to selectively aromatize the cyclized intermediate 6' to 6 but not over oxidize 6 to (M+16) N-oxide. Different metal and non-metal based oxidants were employed to catalyze/promote the oxidation of 6' to 6, including copper acetate (Cu(OAc)$_2$·H$_2$O), sodium perborate (NaBO$_3$·4H$_2$O), ferric chloride (FeCl$_3$·6H$_2$O), palladium on Carbon (10% Pd/C). Reactions were performed in 4 dram vials with closed caps at room temperature. Magnetic stir bars were used for mixing the reaction. No external air bubbling or nitrogen atmosphere was applied. The reaction scale was chosen at 100 mg relative to 4. The results from this study are detailed in Table 1.

TABLE 35

Preparation of 6 Using External Oxidants

| Entry | Time (h) | 4 (% AUC) | 6 (% AUC) | 6' (% AUC) | (M + 16) (% AUC) |
|---|---|---|---|---|---|
| A-1 | 1.5 | 12.3 | 9.3 | 77.9 | — |
| A-2 | 3.5 | 8 | 36 | 56 | — |
| A-3 | 5.5 | 6.6 | 47 | 46.4 | — |
| A-4 | 22 | 3.4 | 74 | 22.6 | — |
| Experiment B (Cu(OAc)$_2$·H$_2$O) | | | | | |
| B-1 | 1.5 | 17.7 | 8.8 | 73.5 | — |
| B-2 | 3.5 | 11.6 | 17.4 | 71 | — |
| B-3 | 5.5 | 10.3 | 16.3 | 73.4 | — |
| B-4 | 22 | 9 | 15.3 | 75.7 | — |
| Experiment C (NaBO$_3$·4H$_2$O) | | | | | |
| C-1 | 1.5 | 13.4 | 30.1 | 56.5 | — |
| C-2 | 3.5 | 7.4 | 60.9 | 31.7 | — |
| C-3 | 5.5 | 5.3 | 73.3 | 21.4 | — |
| C-4 | 22 | 0.6 | 97.3 | 2.1 | — |

TABLE 35-continued

Preparation of 6 Using External Oxidants

| Entry | Time (h) | 4 (% AUC) | 6 (% AUC) | 6' (% AUC) | (M + 16) (% AUC) |
|---|---|---|---|---|---|
| Experiment D (FeCl$_3$•6H$_2$O) | | | | | |
| D-1 | 1.5 | 24.9 | 71.7 | 3.4 | — |
| D-2 | 3.5 | 15.6 | 83.9 | 0.5 | — |
| D-3 | 5.5 | 11.4 | 88.4 | — | — |
| D-4 | 22 | 4.8 | 95 | 0.2 | — |
| Experiment E (10% Pd/C) | | | | | |
| E-1 | 1.5 | 17 | 26.3 | 56.7 | — |
| E-2 | 22 | 6.4 | 70.2 | 23.4 | — |

Reaction conditions: 1 equiv., of 4, 1.05 equiv., of 5, 10 vol., of AcOH/MeOH (9:1 ratio) solution, stir at room temperature with different oxidants (1 equiv.).

The reactions were generally complete in 12-15 h (compared to 35-40 h under air oxidation conditions). The product 6 (97-98% AUC purity) was precipitated from the reaction mixture by the addition of water (10 vol.). The M+16 N-oxide was observed in 0.1-0.5% AUC in the isolated product. To further streamline the process, Step 2 and Step 3 of the process are now combined (Step 2'). Once the conversion of 3 to 4 is complete, the obtained THF solution of 4 is solvent swapped to MeOH to accommodate the optimized conditions for converting 4 to 6 with sodium perborate as the oxidant. The current detailed process is described below:

Step 1, Synthesis of 3:

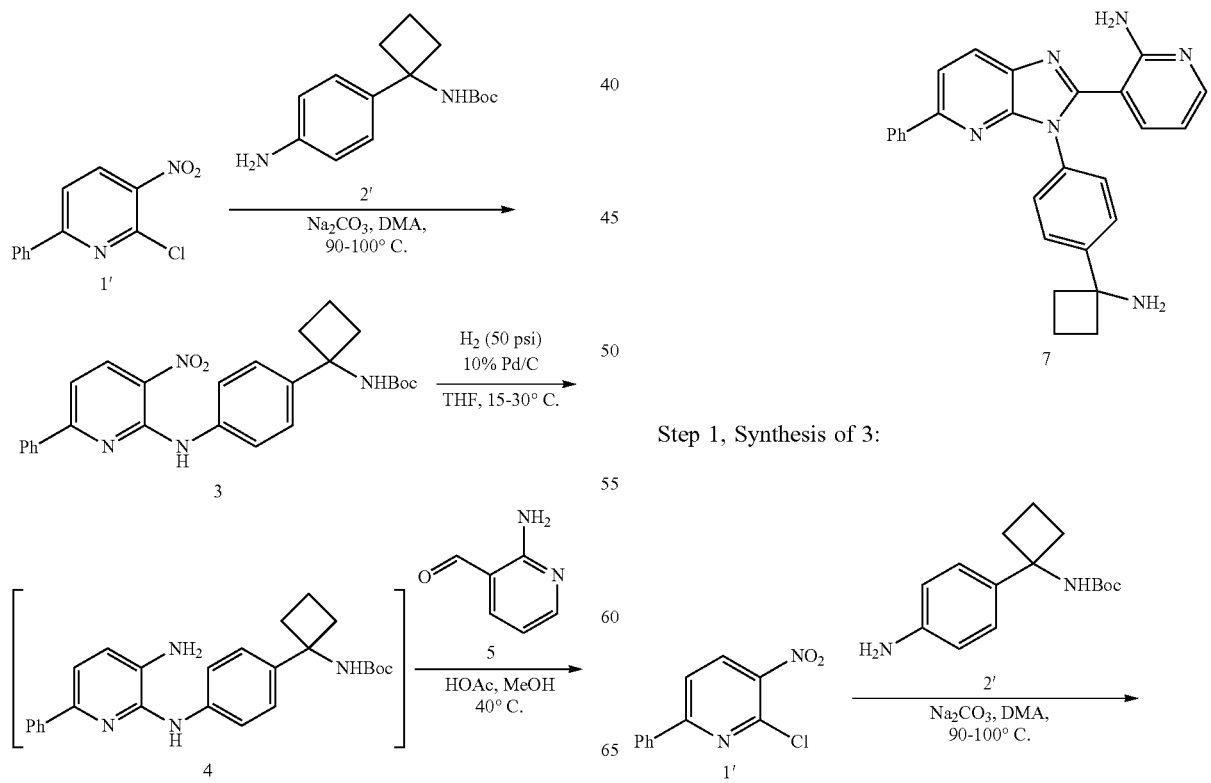

-continued

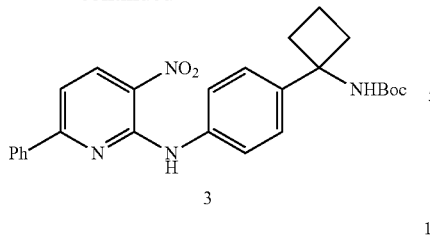

3

A 22 L reaction flask was set up in a heating mantle and purged with nitrogen prior to charging 1' (1.20 kg), 2' (1.48 kg), sodium carbonate (1.09 kg) and dimethylacetamide (7.3 kg). The reaction mixture was warmed to approximately 91° C. and allowed to stir at this temperature under nitrogen. The mixture was sampled for analysis by HPLC after 20 hours with the result showing approximately 2% AUC (relative to product) of 1' remaining. Analysis of a sample after 24 hours indicated approximately 1.5% AUC 1' remaining relative to product. The heating was shut off after approximately 26 hours of heating and the reaction mixture was allowed to cool overnight (HPLC analysis: 1.1% AUC of 1'). After cooling, the reaction mixture was transferred to the 100 L reactor. The reaction flask was rinsed with 20.6 kg of 2-MeTHF into the 100 L reactor and the batch was washed with 5% aqueous sodium chloride (22.1 kg). The layers were separated and the aqueous layer was back-extracted with 14.7 kg of 2-MeTHF. After separating the layers there was a significant amount of salt/sodium carbonate remaining in the reactor. The aqueous layer was charged to the reactor and warmed to 30° C. An additional 5.0 kg of water was charged to dissolve most of the salt (hazy solution) and the aqueous layer was extracted with 15.0 kg of 2-MeTHF. A significant amount of product had crystallized from the first and second organic layers after being stored over the weekend. The organic layers were charged to the reactor and the remaining solid dissolved in 5.0 kg of 2-MeTHF and combined with the organic layer in the reactor. The combined organics were washed twice with 5% aqueous sodium chloride (12.0 kg each wash). Analysis of the organic layer by $^1$H-NMR indicated 0.1 mole percent dimethylacetamide remained. After distillation of the organic layer to 18 L, analysis of a sample indicated that the moisture level was 0.15%. The batch was diluted with 2-MeTHF (25.5 kg) and cooled to 28° C. before polish filtering through a 0.22-micron filter. The 100 L reactor was rinsed with polish filtered 2-MeTHF before re-charging the filtered batch. The batch was then vacuum distilled to 10.8 L and warmed to 72° C. Heptane (7.4 kg) was charged over 75 minutes maintaining the temperature between 66 and 72° C. After stirring at 66° C. for 16 minutes the batch was cooled to 25° C. over 2 hr, 45 min. The batch was stirred at this temperature for 15.5 hr before sampling. The sample was filtered and the filtrate analyzed by HPLC indicating 4 mg/mL of product in the filtrate. The batch was filtered, washed twice with a 1:3 (v/v) mixture of 2-MeTHF in heptane (4.4 kg each wash) and washed once with 4.1 kg of heptane. The product was dried on the filter under nitrogen for 1 hr, 18 min and transferred to drying trays (2.31 kg wet). After drying overnight at 25-30° C. the weight was constant and the product was packaged to give 2.17 kg of 3 (92% yield, 99.8% AUC).

Step 2', Synthesis of 6:

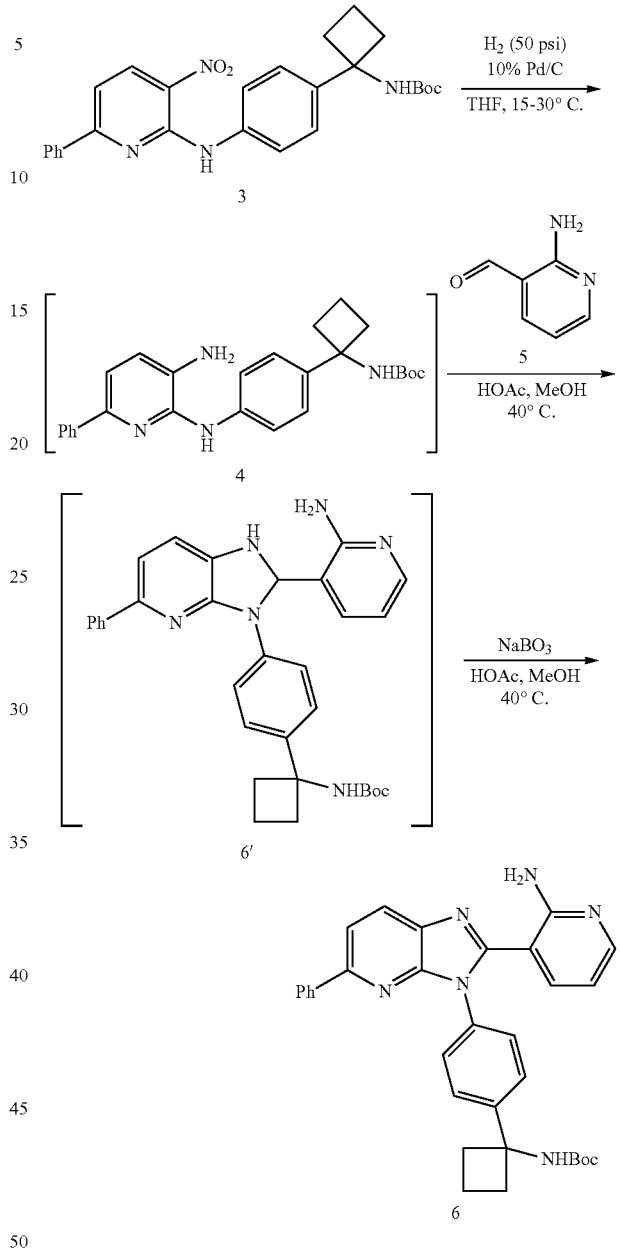

After performing a pressure check and inerting with nitrogen, the 10-gallon reactor was charged with 1.89 kg of 3 followed by 95 g of 10% Pd/C (50% wet). The reactor was then purged three times with nitrogen before charging 10.3 kg of tetrahydrofuran (THF). The reactor was sealed and evacuated to −20 inch-Hg before pressurizing to 30 psi with hydrogen. The initial reaction temperature was 15° C. and the batch self-heated to 30° C. as the reaction progressed. After 3.75 hours reaction time the batch was sampled for HPLC analysis (hydrogenation continued at 30 psi during analysis). The analysis at this time indicated 0.43% AUC starting material (3) remained and after 5 hours total reaction time the reactor was vented and purged with nitrogen. Analysis after filtering the catalyst indicated 0.23% AUC starting material (3) remained. The reactor was rinsed with 8.0 kg of THF and this rinse was also used to rinse the filter into the batch. The batch was charged to a 100 L jacketed reactor and 1.6 kg of THF was used to rinse the carboys into the 100 L jacketed reactor. The batch (~34 L) was vacuum distilled at 25° C. to 9 L before charging 6.4 kg of methanol. Vacuum distillation was continued to 8 L, 6.6 kg of methanol was charged, and the distillation continued to 8 L. Analysis by $^1$H-NMR indicated 4.5 mole % THF remained relative to methanol so two additional chases (6.6 kg and 6.4 kg) with methanol were performed, after which the mole % of THF relative to methanol was 0.1 mole percent. To the batch was charged 527 g of 5 and 632 g of sodium perborate tetrahydrate. The batch was warmed to 40° C. and agitated for 2 hours before sampling for the first IPC. Analysis by HPLC indicated that 5.6% AUC of 4 was unreacted, the stirring was continued at 40° C. overnight. Analysis of samples taken after 19 hours and 22 hours showed no change in a peak (1.6% AUC of 6') with a retention time similar to the intermediate 6'. The reaction was quenched with water (29.8 kg) and stirred at 35-40° C. for 1 hour. The batch was cooled over 2 hours to 24° C. and stirred overnight (17 hours) at 15-25° C. The product was filtered, washed twice with water (13.6 kg each wash) followed by heptane (9.3 kg). Drying of the crude intermediate to constant weight at 45° C. required 47 hours. Analysis of the intermediate indicated the purity was 97.2% AUC. This material (1.84 kg) was charged to the 100 L jacketed reactor with isopropyl acetate (IPAc, 12.8 kg) under nitrogen. The mixture was heated to 70° C. (required 1 hr 12 min), stirred for 1 hour and then cooled over 10 hours to 20° C. The slurry was stirred at 20° C. for 54 hours before filtering. The product was washed with 1.6 kg of IPAc followed by 50% (v/v) of IPAc/heptane (1.8 L). The product was dried at 40-45° C. for 18 hours to give 1.33 kg of 6 (61% yield, 99.3% AUC)

Step 3', Synthesis of 7:

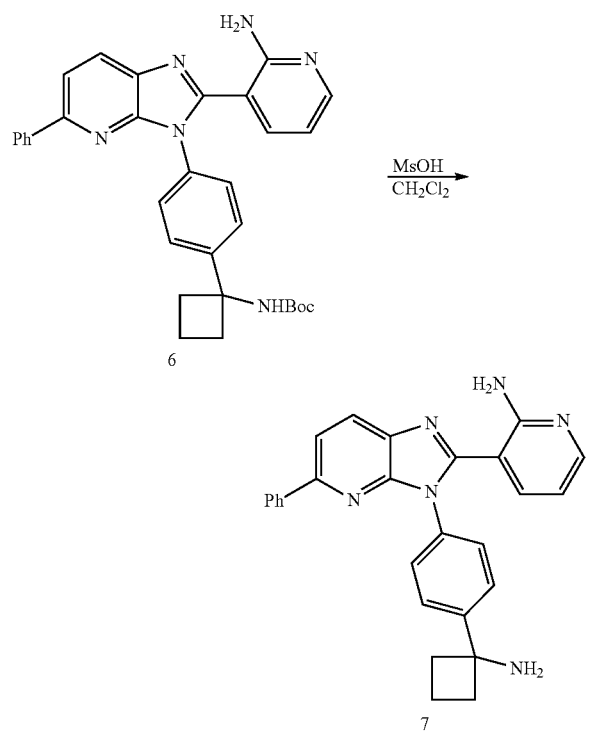

The intermediate from the previous step (6, 1.33 kg) was charged to a 100 L jacketed reactor under nitrogen followed by addition of dichloromethane (18.6 kg). To this solution at 20° C., methanesulfonic acid (1.27 kg) was added over 34 minutes with a resultant temperature rise to 24° C. The mixture was stirred at 20-23° C. and monitored by HPLC. Analysis of a sample after 4.5 hours showed 0.3% AUC starting material. Water (1.4 kg) was charged to the reaction which was stirred at 20° C. overnight. Additional dichloromethane (9.1 kg) was charged due to product precipitation prior to charging 6N sodium hydroxide (3.0 kg) to adjust the pH to 13. After agitating for 15 minutes the mixture was settled and the lower organic layer drained. The aqueous layer was extracted with dichloromethane (15.0 kg). The combined organic layers were washed with water (8.0 kg). Karl Fisher analysis of the organic layer indicated the water content was 0.2% moisture so additional drying with sodium sulfate was not required. Quadrasil MP (191 g) was charged to the organic layer in the 100 L jacketed reactor which was warmed to 30° C. and stirred at this temperature for 15.5 hours. The scavenger was filtered, washed twice with dichloromethane (2×1.9 kg) and returned to the cleaned 100 L reactor. The batch was vacuum distilled to approximately 4 L before charging isopropyl acetate (8.6 kg) and vacuum distillation continued to approximately 5 L. After adjusting the volume to the desired level (~10 L) with isopropyl acetate the mixture was sampled for $^1$H-NMR. The level of dichloromethane as determined by $^1$H-NMR was 2.3 mole percent. Isopropyl acetate (4.7 kg) was charged and the vacuum distillation continued to a final volume of 9 L. Analysis by $^1$H-NMR indicated 0.5 mole percent dichloromethane remained (specification <1%). Isopropyl acetate (1.6 kg) was charged and the mixture stirred at 20-25° C. for 16 hours. The mixture was then filtered and the solid washed on the filter twice with isopropyl acetate (2.3 kg and 2.5 kg). The solid was dried at 42° C. for 1 day to give 805 g of 7 (70% yield, 99.5% AUC).

The invention claimed is:
1. A process of preparing 3-(3-(4-(1-aminocyclobutyl) phenyl)-5-phenyl-3H-imidazo[4,5-b]pyridin-2-yl)pyridin-2-amine, comprising the steps of
    Step 2', treating tert-butyl (1-(4-((3-nitro-6-phenylpyridin-2-yl)amino)phenyl)cyclobutyl)carbamate with a reducing agent in a polar aprotic solvent to form tert-butyl (1-(4-((3-amino-6-phenylpyridin-2-yl)amino)phenyl)cyclobutyl)carbamate, replacing the polar aprotic solvent with a polar protic solvent, and reacting tert-butyl (1-(4-((3-amino-6-phenylpyridin-2-yl)amino)phenyl)cyclobutyl)carbamate with 2-aminonicotinaldehyde in the presence of an oxidant and an acid in a polar protic solvent to form tert-butyl (1-(4-(2-(2-aminopyridin-3-yl)-5-phenyl-3H-imidazo[4,5-b] pyridin-3-yl)phenyl)cyclobutyl)carbamate; and
    Step 3', treating tert-butyl (1-(4-(2-(2-aminopyridin-3-yl)-5-phenyl-3H-imidazo[4,5-b]pyridin-3-yl)phenyl)cyclobutyl)carbamate with an acid in a polar aprotic solvent to form 3-(3-(4-(1-aminocyclobutyl)phenyl)-5-phenyl-3H-imidazo[4,5-b]pyridin-2-yl)pyridin-2-amine.

2. The process according to claim 1, further comprising before Step 2',
    Step 1, reacting 2-chloro-3-nitro-6-phenylpyridine with tert-butyl (1-(4-aminophenyl)cyclobutyl)carbamate in the presence of a base in a polar aprotic solvent to form tert-butyl (1-(4-((3-nitro-6-phenylpyridin-2-yl)amino) phenyl)cyclobutyl)carbamate.

3. The process according to claim 1, further comprising before Step 2',

Step 1a, coupling 3-nitro-6-phenylpyridin-2-amine with tert-butyl (1-(4-bromophenyl)cyclobutyl)carbamate in the presence of a palladium catalyst and a phosphorus ligand in a polar aprotic solvent to form tert-butyl (1-(4-(((3-nitro-6-phenylpyridin-2-yl)amino)phenyl)cyclobutyl)carbamate.

4. The process according to claim 1, wherein the oxidant is air.

5. The process according to claim 1, wherein the oxidant is a metal or non-metal based salt or catalyst.

6. The process according to claim 5, wherein the oxidant is selected from the group consisting of metal acetate, metal perborate, metal chloride, palladium based catalyst, and hydrates thereof.

7. The process according to claim 6, wherein the oxidant is selected from the group consisting of $Cu(OAc)_2 \cdot H_2O$, $NaBO_3 \cdot 4H_2O$, $FeCl_3 \cdot 6H_2O$, and 10% Pd/C, and hydrates thereof.

8. The process according to claim 7, wherein the oxidant is $NaBO_3 \cdot 4H_2O$.

* * * * *